(12) United States Patent
Klemke et al.

(10) Patent No.: US 12,049,644 B2
(45) Date of Patent: Jul. 30, 2024

(54) PLATFORM FOR GENERATING SAFE CELL THERAPEUTICS

(71) Applicant: The Regents of the University of California, La Jolla, CA (US)

(72) Inventors: Richard Klemke, La Jolla, CA (US); Huawei Wang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 597 days.

(21) Appl. No.: 17/145,848

(22) Filed: Jan. 11, 2021

(65) Prior Publication Data

US 2021/0189345 A1 Jun. 24, 2021

Related U.S. Application Data

(63) Continuation of application No. 16/715,859, filed on Dec. 16, 2019, now Pat. No. 10,927,349, which is a continuation of application No. PCT/US2018/045686, filed on Aug. 7, 2018.

(60) Provisional application No. 62/542,133, filed on Aug. 7, 2017.

(51) Int. Cl.
| | |
|---|---|
| C12N 5/0775 | (2010.01) |
| A61K 9/00 | (2006.01) |
| A61K 35/12 | (2015.01) |
| A61K 35/17 | (2015.01) |
| A61K 35/28 | (2015.01) |
| A61K 38/20 | (2006.01) |
| A61K 39/00 | (2006.01) |
| A61K 39/215 | (2006.01) |
| A61P 35/00 | (2006.01) |
| C12N 5/0783 | (2010.01) |
| C12N 5/10 | (2006.01) |
| C12N 15/85 | (2006.01) |
| C12N 15/88 | (2006.01) |

(52) U.S. Cl.
CPC .......... *C12N 5/0662* (2013.01); *A61K 9/0019* (2013.01); *A61K 35/12* (2013.01); *A61K 35/17* (2013.01); *A61K 35/28* (2013.01); *A61K 38/2066* (2013.01); *A61K 38/208* (2013.01); *A61K 39/001102* (2018.08); *A61K 39/215* (2013.01); *A61P 35/00* (2018.01); *C12N 5/0646* (2013.01); *C12N 5/0667* (2013.01); *C12N 5/10* (2013.01); *C12N 15/85* (2013.01); *C12N 15/88* (2013.01); *A61K 2039/515* (2013.01); *A61K 2039/545* (2013.01); *C12N 2501/999* (2013.01); *C12N 2510/00* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 6,054,281 | A | 4/2000 | Russel et al. |
| 6,511,967 | B1 | 1/2003 | Weissleder et al. |
| 6,538,121 | B1 | 3/2003 | He et al. |
| 6,583,121 | B1 | 6/2003 | Johnston et al. |
| 6,951,756 | B2 | 10/2005 | Lubitz et al. |
| 9,364,504 | B2 | 6/2016 | Godfrin et al. |
| 9,546,371 | B2 | 1/2017 | Mamoun et al. |
| 9,950,049 | B2 | 4/2018 | Godfrin et al. |
| 10,105,436 | B2 | 10/2018 | Szalay et al. |
| 10,329,531 | B2 | 6/2019 | Kahvejian et al. |
| 10,456,421 | B2 | 10/2019 | Kahvejian et al. |
| 10,471,099 | B2 | 11/2019 | Lodish et al. |
| 10,927,349 | B2 | 2/2021 | Klemke et al. |
| 10,947,507 | B2 | 3/2021 | Klemke et al. |
| 10,960,071 | B2 | 3/2021 | Klemke et al. |
| 2002/0142397 | A1 | 10/2002 | Collas et al. |
| 2003/0113910 | A1 | 6/2003 | Levanduski |
| 2004/0156858 | A1 | 8/2004 | Franzusoff et al. |
| 2004/0214783 | A1 | 10/2004 | Terman |
| 2004/0259249 | A1 | 12/2004 | Strelchenko et al. |
| 2007/0092968 | A1 | 4/2007 | Ji et al. |
| 2008/0182292 | A1 | 7/2008 | Gerdes et al. |
| 2009/0004744 | A1 | 1/2009 | Surber et al. |
| 2011/0070153 | A1 | 3/2011 | Hyde et al. |
| 2011/0286978 | A1 | 11/2011 | Klimanskaya et al. |
| 2012/0107347 | A1 | 5/2012 | Hodge et al. |
| 2012/0164161 | A1 | 6/2012 | Hagemann et al. |
| 2013/0302407 | A1 | 11/2013 | Rao et al. |
| 2015/0104428 | A1 | 4/2015 | Shi et al. |
| 2016/0075712 | A1 | 3/2016 | Shi et al. |
| 2016/0082046 | A1 | 3/2016 | Lodish et al. |
| 2016/0108429 | A1 | 4/2016 | Fisher et al. |
| 2016/0137716 | A1 | 5/2016 | El Andaloussi |

(Continued)

FOREIGN PATENT DOCUMENTS

| | | |
|---|---|---|
| CN | 104877965 | 9/2015 |
| JP | 2013144707 | 7/2013 |

(Continued)

OTHER PUBLICATIONS

Chernega, et al. (2022) "Mitochondrion-targeted RNA therapies as a potential treatment strategy for mitochondrial diseases", Molecular Therapy Nucleic Acids, 30: 359-377. (Year: 2022).*
Wang, et al. (2022) "Enucleated human mesenchymal stromal cells for the homing and delivery of therapeutic cargos in vivo", Nature Biomedical Engineering, 6(7): 882-97 (provided as HHS Public Access Author Manuscript, 35 pages long). (Year: 2022).*
International Search Report and Written Opinion in International Appln. No. PCT/US2021/016919, dated Apr. 28, 2021, 9 pages.
St. Clair, "Interleukin 10 treatment for rheumatoid arthritis," Annals of the Rheumatic Diseases, 1999, 58(1):I99-I102.

(Continued)

*Primary Examiner* — Robert M Kelly
(74) *Attorney, Agent, or Firm* — Fish & Richardson P.C.

(57) ABSTRACT

Provided are cytoplasts (enucleated cells), methods for making cytoplasts, compositions comprising cytoplasts, and methods for using cytoplasts.

15 Claims, 37 Drawing Sheets

Specification includes a Sequence Listing.

(56) References Cited

U.S. PATENT DOCUMENTS

| | | |
|---|---|---|
| 2016/0145332 A1 | 5/2016 | Mackay et al. |
| 2016/0166613 A1 | 6/2016 | Spencer et al. |
| 2016/0199413 A1 | 6/2016 | Simonson et al. |
| 2016/0257932 A1 | 9/2016 | Kahvejian et al. |
| 2016/0272707 A1 | 9/2016 | Levine et al. |
| 2016/0289645 A1 | 10/2016 | Tufaro et al. |
| 2017/0020926 A1 | 1/2017 | Mata-Fink et al. |
| 2017/0051307 A1 | 2/2017 | Rose et al. |
| 2017/0081326 A1 | 3/2017 | Ibrahim et al. |
| 2017/0166877 A1 | 6/2017 | Bayle et al. |
| 2017/0174762 A1 | 6/2017 | Zinzalla et al. |
| 2017/0239338 A1 | 8/2017 | Szalay et al. |
| 2017/0240637 A1 | 8/2017 | Cheung et al. |
| 2017/0258898 A1 | 9/2017 | Asimakopoulos et al. |
| 2018/0044391 A1 | 2/2018 | Gundram et al. |
| 2018/0092951 A1 | 4/2018 | Szalay et al. |
| 2018/0153989 A1 | 6/2018 | Kahvejian et al. |
| 2018/0271910 A1 | 9/2018 | Mata-Fink et al. |
| 2018/0344822 A1 | 12/2018 | Godfrin et al. |
| 2018/0344868 A1 | 12/2018 | Zinzalla et al. |
| 2019/0055314 A1 | 2/2019 | Luo et al. |
| 2019/0083540 A1 | 3/2019 | Kahvejian et al. |
| 2019/0093105 A1 | 3/2019 | Gibbings et al. |
| 2019/0153039 A1 | 3/2019 | Ebert et al. |
| 2019/0153409 A1 | 5/2019 | Arber et al. |
| 2019/0160102 A1 | 5/2019 | Hoffman et al. |
| 2019/0167810 A1 | 6/2019 | Hean et al. |
| 2019/0201462 A1 | 6/2019 | Tufaro et al. |
| 2019/0209525 A1 | 6/2019 | Bachovchin et al. |
| 2019/0276533 A1 | 9/2019 | Zhang et al. |
| 2019/0298769 A1 | 10/2019 | Wickham et al. |
| 2019/0367880 A1 | 12/2019 | Draganov et al. |
| 2020/0009201 A1 | 1/2020 | Jewett |
| 2020/0038453 A1 | 2/2020 | Annala et al. |
| 2020/0040064 A1 | 2/2020 | Caligiuri et al. |
| 2020/0054675 A1 | 2/2020 | DiPersio et al. |
| 2020/0055912 A1 | 2/2020 | Kley et al. |
| 2020/0060979 A1 | 2/2020 | Chung |
| 2020/0095320 A1 | 3/2020 | Pan et al. |
| 2020/0095553 A1 | 3/2020 | Yang et al. |
| 2020/0108066 A1 | 4/2020 | Goel et al. |
| 2020/0109183 A1 | 4/2020 | Wiklander et al. |
| 2020/0140562 A1 | 5/2020 | Tsun et al. |
| 2020/0140824 A1 | 5/2020 | Fernandez Santidrian et al. |
| 2020/0148742 A1 | 5/2020 | Grandi et al. |
| 2020/0164020 A1 | 5/2020 | Zhou et al. |
| 2020/0181251 A1 | 6/2020 | Buckler et al. |
| 2020/0197534 A1 | 6/2020 | Mei et al. |
| 2020/0215114 A1 | 7/2020 | Rodriguez-Araujo et al. |
| 2020/0216814 A1 | 7/2020 | Klemke et al. |
| 2020/0216918 A1 | 7/2020 | Langlois et al. |
| 2020/0255863 A1 | 8/2020 | Micol et al. |
| 2020/0276318 A1 | 9/2020 | Patrick et al. |
| 2020/0300857 A1 | 9/2020 | Haining et al. |
| 2020/0306366 A1 | 10/2020 | Klemke et al. |
| 2020/0318073 A9 | 10/2020 | Draganov et al. |
| 2020/0323862 A1 | 10/2020 | Estok et al. |
| 2020/0332009 A1 | 10/2020 | Miao et al. |
| 2020/0345845 A1 | 11/2020 | Kahvejian et al. |
| 2020/0362052 A1 | 11/2020 | Tachado |
| 2020/0368285 A1 | 11/2020 | Klemke et al. |
| 2020/0368287 A1 | 11/2020 | Klemke et al. |
| 2020/0390876 A1 | 12/2020 | Manting et al. |
| 2020/0407419 A1 | 12/2020 | Lewis et al. |
| 2020/0407421 A1 | 12/2020 | Hermiston et al. |
| 2021/0000750 A1 | 1/2021 | Gu et al. |
| 2021/0032662 A1 | 2/2021 | Ilkow et al. |
| 2021/0040205 A1 | 2/2021 | Jang et al. |
| 2021/0060052 A1 | 3/2021 | Quay |
| 2021/0060126 A1 | 3/2021 | Youssef et al. |
| 2021/0106632 A1 | 4/2021 | Kim et al. |
| 2021/0139846 A1 | 5/2021 | Bazan |
| 2021/0145876 A1 | 5/2021 | Parks et al. |
| 2021/0162038 A1 | 6/2021 | Klemke et al. |
| 2021/0180059 A1 | 6/2021 | Maresca et al. |
| 2023/0015661 A1 | 1/2023 | Klemke et al. |
| 2023/0103075 A1 | 3/2023 | Klemke et al. |

FOREIGN PATENT DOCUMENTS

| | | |
|---|---|---|
| WO | WO200224897 | 3/2002 |
| WO | WO2007095747 | 8/2007 |
| WO | WO2013038066 | 3/2013 |
| WO | WO2015128492 | 9/2015 |
| WO | WO2015153102 | 10/2015 |
| WO | WO2016141357 | 9/2016 |
| WO | WO 2016183482 | 11/2016 |
| WO | WO2016186482 | 11/2016 |
| WO | WO2017165245 | 9/2017 |
| WO | WO2017173034 | 10/2017 |
| WO | WO2018006880 | 1/2018 |
| WO | WO2018064513 | 4/2018 |
| WO | WO2018081738 | 5/2018 |
| WO | WO2018112032 | 6/2018 |
| WO | WO2018148378 | 8/2018 |
| WO | WO2018208728 | 11/2018 |
| WO | WO2019017940 | 1/2019 |
| WO | WO 2019032628 | 2/2019 |
| WO | WO2019055851 | 3/2019 |
| WO | WO2019090355 | 5/2019 |
| WO | WO2019113512 | 6/2019 |
| WO | WO2019113711 | 6/2019 |
| WO | WO2019169141 | 9/2019 |
| WO | WO2019195819 | 10/2019 |
| WO | WO2019213706 | 11/2019 |
| WO | WO2019217646 | 11/2019 |
| WO | WO2019236633 | 12/2019 |
| WO | WO2019246111 | 12/2019 |
| WO | WO2019246528 | 12/2019 |
| WO | WO2020016900 | 1/2020 |
| WO | WO2020023350 | 1/2020 |
| WO | WO2020028533 | 2/2020 |
| WO | WO2020037434 | 2/2020 |
| WO | WO2020049158 | 3/2020 |
| WO | WO2020069452 | 4/2020 |
| WO | WO2020069454 | 4/2020 |
| WO | WO2020072126 | 4/2020 |
| WO | WO2020205579 | 10/2020 |
| WO | WO2021041473 | 3/2021 |

OTHER PUBLICATIONS

Alarcón et al., "Enucleated Cells As Delivery Vehicles To Treat Cancer," In Molecular Biology Of The Cell, Dec. 15, 2018, 29(26): 1 page.

Page et al., "Two may be better than one: PD-1/PD-L1 blockade combination approaches in metastatic breast cancer," NPJ breast cancer, Oct. 8, 2019, 5(34): 1- 9.

Ruella et al., "Next-generation chimeric antigen receptor T-cell therapy: going off the shelf," BioDrugs, Dec. 2017, 31(6): 15 pages.

Schlake et al., "mRNA: a novel avenue to antibody therapy?," Molecular Therapy, Apr. 10, 2019, 27(4):773-784.

International Preliminary Report on Patentability in International Appln. No. PCT/US2021/016919, dated Jul. 28, 2022, 7 pages.

Bhat et al., "Rab35 and its effectors promote formation of tunneling nanotubes in neuronal cells," Scientific reports, Oct. 8, 2020, 10(1):1-14.

Buszczak et al., "Signaling by cellular protrusions: keeping the conversation private," Trends in cell biology, Jul. 1, 2016, 26(7):526-534.

Hekmatshoar et al., "The role of metabolism and tunneling nanotube-mediated intercellular mitochondria exchange in cancer drug resistance," Biochemical Journal, Jul. 31, 2018, 475(14):2305- 2328.

Yadav et al., "Golgi proteins in circulating human platelets are distributed across non-stacked, scattered structures," Platelets May 19, 2017, 28(4):400-408.

Neve et al., "A collection of breast cancer cell lines for the study of functionally distinct cancer subtypes," Cancer cell, Dec. 1, 2006, 10(6):515-527.

Wang et al., "Potential of CXCR4/CXCL12 chemokine axis in cancer drug delivery," Current pharmacology reports, Feb. 2016, 2(1):1-10.

(56) References Cited

OTHER PUBLICATIONS

Zakhartsev et al. "Cell size and morphological properties of yeast *Saccharomyces cerevisiae* in relation to growth temperature," FEMS yeast research, Sep. 2018, 18(6): 26 pages.
Guo, "Enucleation technology of in vitro cultured cells and the use thereof in virology (review)," Acta Academiae Medicinae Sinicae, Mar. 1980, 2(1):73-76, Machine translation.
Philips et al., "Therapeutic uses of anti-PD-1 and anti-PD-L1 antibodies," International immunology, Jan. 1, 2015, 27(1):39-46.
Serwer et al., [online], "Systemic and Local Drug Delivery for Treating Diseases of the Central Nervous System in Rodent Models," J Vis Exp., 2010 retrieved on Nov. 10, 2022, 6 pages.
Yeo et al., "Cellular dynamics of mammalian red blood cell production in the erythroblastic island niche," Biophysical reviews, Dec. 2019, 11(6):873-894.
Yoo et al., "Bio-inspired, bioengineered and biomimetic drug delivery carriers," Nature reviews Drug discovery, Jul. 2011, 10(7): 16 pages.
Bahadoran et al., "Immune responses to influenza virus and its correlation to age and inherited factors," Frontiers in microbiology, Nov. 22, 2016, 7: 11 Pages.
Chen et al., "Alteration of T cell immunity by lentiviral transduction of human monocyte-derived dendritic cells," Retrovirology, Dec. 1, 2004, 1(1): 12 Pages.
Cheng-Jun et al., "Preparation and activity of cytoplasts from bone marrow mesenchymal stem cells," Journal of Clinical and Rehabilitative Tissue Engieering Research, 2008, 12(43):8449-53.
Cook, "Evidence based route of administration of vaccines," Human vaccines, Jan. 1, 2008, 4(1): 8 Pages.
Du et al., "Cytoplast containing reprogramming-related factors from human embryonic stem cells arrested at metaphase," Development, Growth, & Differentiation, 2010, 53(1):18-25.
Extended European Search Report in EP Appln. No. 18845202, dated May 19, 2020, 9 pages.
Huang, "Vaccinia Virus-mediated Therapy of Solid Tumor Xenografts: Intra-tumoral Delivery of Therapeutic Antibodies," 2013, 172 pages.
Ishikawa et al., "The protective effects of intranasal administration of IL-12 given before influenza virus infection and the negative effects of IL-12 treatment given after viral infection," Journal of Medical Virology, Sep. 2016, 88(9): 10 Pages.
Iyer et al., "Role of Interleukin 10 Transcriptional Regulation in Inflammation and Autoimmune Disease," Crit Rev Immunol, 2012, 32(1): 23-63.
Jones et al., "Viral persistence: IL-10 is the key," Nature Reviews Microbiology, Dec. 2006, 4(12):879.
Kagawa et al., "Gene therapy of mitochondrial diseases using human cytoplasts," Gene Therapy, 1997, 4:6-10.
Mo et al., "ATP-triggered anticancer drug therapy," Nature Communications, 2014, 5:3364.
Patil et al., "Virotherapy of Canine Tumors with Oncolytic Vaccinia Virus GLV-1h109 Expressing an Anti-VEGF Single-Chain Antibody," PLoS One, 2021, 7(10): e47472.
PCT International Preliminary Report on Patentability in Appln. No. PCT/US2018/045686, dated Feb. 11, 2020, 7 pages.
PCT International Search Report and Written Opinion in International Appln. No. PCT/US2018/045686, dated Oct. 19, 2018, 8 pages.
Shi et al., "Engineered red blood cells as carriers for systemic delivery of a wide array of functional probes," Proceedings of the National Academy of Science, 2014, 111(28):10131-10136.
Tena et al., "Transgenic expression of human CD47 markedly increases engraftment in a murine model of pig-to-human hematopoietic cell transplantation," American Journal of Transplantation, 2014, 14(12):2713-2722.
United Kingdom Office Action in UK Appln. No. 2000541.9, dated Jan. 30, 2020, 3 pages.
Ardolino et al., "Cytokine treatment in cancer immunotherapy," Oncotarget, Aug. 14, 2015, 6(23):19346-19347.
Carpi et al., "Cytokines in the management of high risk or advanced breast cancer: an update and expectation," Current Cancer Drug Targets, Dec. 1, 2009, 9(8):888-903.
Dias et al., "IL-12 regulates VEGF and MMPs in a murine breast cancer model," International journal of cancer, Oct. 29, 1998, 78(3):361-365.
Eliopoulos et al., "Neo-organoid of marrow mesenchymal stromal cells secreting interleukin-12 for breast cancer therapy," Cancer research, Jun. 15, 2008, 68(12):4810-4818.
Rakhmilevich et al., "Treatment of experimental breast cancer using interleukin-12 gene therapy combined with anti-vascular endothelial growth factor receptor-2 antibody," Molecular cancer therapeutics, Aug. 1, 2004, 3(8):969-976.
Sabel et al., "Intratumoral delivery of encapsulated IL-12, IL-18 and TNF-α in a model of metastatic breast cancer," Breast cancer research and treatment, Jul. 2010, 122(2): 12 pages.
Yang et al., "Interleukin-12 activated CD8+ T cells induces apoptosis in breast cancer cells and reduces tumor growth," Biomedicine & Pharmacotherapy, Dec. 1, 2016, 84:1466-1471.

\* cited by examiner

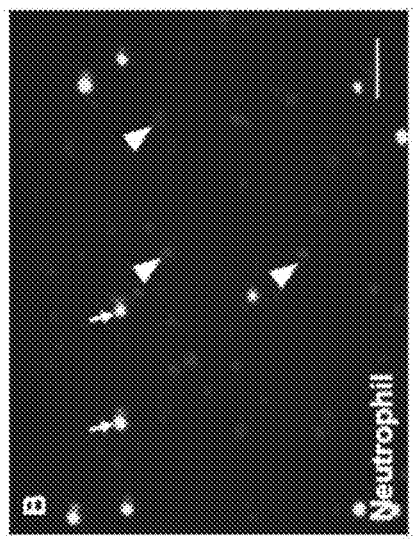
Figure 2A
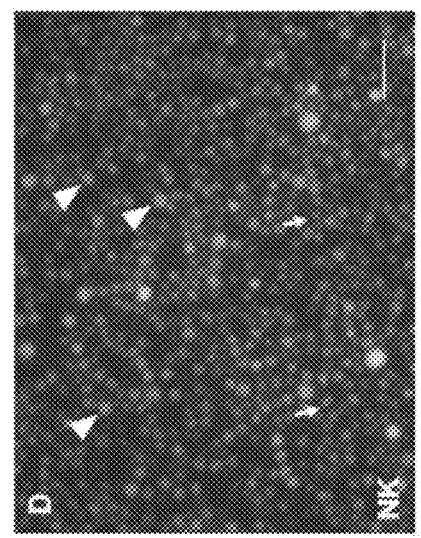
Figure 2B
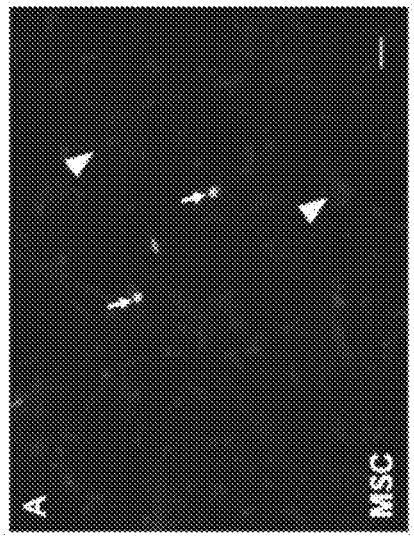
Figure 2C
Figure 2D

MSC | MSC Cytoplast

PLATFORM FOR GENERATING SAFE CELL THERAPEUTICS

CLAIM OF PRIORITY

This application is a continuation of U.S. application Ser. No. 16/715,859, filed on Dec. 16, 2019, which is a continuation of International Application No. PCT/US2018/045686, filed on Aug. 7, 2018, which claims benefit to U.S. Provisional Patent Application Ser. No. 62/542,133, filed Aug. 7, 2017. The entire contents of the foregoing are hereby incorporated by reference.

FEDERALLY SPONSORED RESEARCH OR DEVELOPMENT

This invention was made with Government support under Grant No. CA097022 awarded by the National Institutes of Health. The Government has certain rights in the invention.

TECHNICAL FIELD

The present disclosure relates, at least in part, to the field of biotechnology, and more specifically, to methods and compositions using cytoplasts (e.g., enucleated cells) for treatment, prevention of disease, prophylactic treatment, adjuvant therapy, or immunomodulation in healthy or diseased subjects.

SEQUENCE LISTING

The instant application contains a Sequence Listing which has been submitted electronically in ASCII format and is hereby incorporated by reference in its entirety. Said ASCII copy, created on Aug. 1, 2018, is named Sequence Listing.txt and is 17.1 MB in size.

BACKGROUND

Current techniques and tools for cell-based therapies are often prone to unwanted and dangerous side effects, such as uncontrolled proliferation, increased mutation rate, and anti-DNA immune responses.

SUMMARY

The present disclosure is based, at least in part, on the generation of cytoplasts for use as a safe and controllable therapeutic and/or delivery vehicle. The methods and compositions described herein provide several advantages. Methods for enucleating cells to generate cytoplasts, cytoplasts, compositions, and methods of using cytoplasts described can offer several benefits over previous cell-based therapeutics. First, the cytoplasts, compositions, and methods described herein can be safer than previous cell-based therapies. There can, in some embodiments, be a reduced risk of transferring genetic material, including, e.g., nuclear-encoded DNA gene transfer to host. Further potential safety advantages can include one or more of: not responding to the microenvironment(s) of a subject, not proliferating, and not contributing to disease progression (e.g., compared to nucleated mesenchymal stem cells).

Second, the cytoplasts described herein can have a limited or defined (e.g., known, or programmable) life span. Third, the cytoplasts described herein can have a reduced size compared to cells in some other cell-based therapies.

Fourth, the cytoplasts described herein can maintain potency following cryohibernation or cryopreservation. Cryopreservation includes cooling or freezing, and storing, in the short-term or long-term, biological material (e.g., cells, cytoplasts) at very low temperatures (e.g., $-80°$ C. in solid $CO_2$, $-196°$ C. in liquid nitrogen, etc.). Cryohibernation includes short-term cooling and storing of biological material (e.g., cells, cytoplasts) in suspended animation, at non-freezing temperatures, such as, e.g., at $4°$ C. Cryohibernation of cytoplasts can be advantageous for one or more of the following reasons: cryohibernation is less labor-intensive than cryopreservation, and cytoplasts that have undergone cryohibernation can be transported (e.g., shipped).

Fifth, the cytoplasts described herein can be extensively engineered. For example, the cytoplasts can be engineered to produce or express a therapeutic entity, or home to specific sites. Other advantages of the presently claimed invention are described herein.

Accordingly, provided herein are cytoplasts, compositions comprising cytoplasts, methods of using cytoplasts, and methods of treating a subject, such as providing benefits to a healthy or unhealthy subject, or treating or diagnosing a disease or condition (e.g., a cancer or a neoplasm, an infection, an inflammatory condition, a neurological disease (e.g., a neurodegenerative disease), a degenerative disease, an autoimmune disease, a cardiovascular disease, an ischemic disease, a genetic or inherited disorder, a developmental disorder, an ophthalmologic disease, a skeletal disease, a metabolic disease, a toxicosis, an idiopathic condition, or two or more thereof, or any disease disclosed herein) in a subject. In some embodiments, methods of treating a subject include: administering to the subject a therapeutically effective amount of a composition comprising a cytoplast (e.g., a recombinant cytoplast, any cytoplast described herein). In some embodiments, a cytoplast administered to a subject can produce a therapeutic. In some embodiments, a cytoplast administered to a subject can produce one or more of: a therapeutic DNA molecule, a therapeutic RNA molecule, a therapeutic protein (e.g., an enzyme, an antibody, an antigen, a toxin, cytokine, a protein hormone, a growth factor, a cell surface receptor, or a vaccine), a therapeutic peptide (e.g., a peptide hormone or an antigen), a small molecule therapeutic (e.g., a steroid, a polyketide, an alkaloid, a toxin, an antibiotic, an antiviral, a colchicine, a taxol, a mitomycin, or emtansine), or a therapeutic gene editing factor. In some embodiments, a cytoplast can be engineered to produce one or more of: a therapeutic DNA molecule, a therapeutic RNA molecule, a therapeutic protein, a therapeutic peptide, a therapeutic small molecule, or a therapeutic gene editing factor. In some embodiments, a cytoplast does not need to be engineered to produce one or more of: a therapeutic DNA molecule, a therapeutic RNA molecule, a therapeutic protein, a therapeutic peptide, a therapeutic small molecule, or a therapeutic gene editing factor. For example, in some embodiments, one or more of: a therapeutic DNA molecule, a therapeutic RNA molecule, a therapeutic protein, a therapeutic peptide, a small molecule therapeutic, or a therapeutic gene editing factor can be produced by the cell from which the cytoplast was obtained.

In some embodiments, a therapeutic DNA molecule, a therapeutic RNA molecule, a therapeutic protein, a therapeutic peptide, a small molecule therapeutic, or a therapeutic gene editing factor can include a targeting moiety. Non-limiting exemplary targeting moieties that can be produced by or contained in a cytoplast include chemokine receptors, adhesion molecules, and antigens.

In some embodiments, a cytoplast administered to a subject can contain a therapeutic DNA molecule, a therapeutic RNA molecule, a therapeutic protein (e.g., an enzyme, an antibody, an antigen, a toxin, cytokine, a protein hormone, a growth factor, a cell surface receptor, or a vaccine, or any therapeutic protein that is currently available or in development), a therapeutic peptide (e.g., a peptide hormone or an antigen, or any therapeutic peptide that is currently available or in development), a small molecule therapeutic (e.g., a steroid, a polyketide, an alkaloid, a toxin, an antibiotic, an antiviral, an analgesic, an anticoagulant, an antidepressant, an anticancer drug, an antiepileptic, an antipsychotic, a sedative, a colchicine, a taxol, a mitomycin, emtansine, or any small molecule therapeutic that is currently available or in development), a therapeutic gene editing factor, a therapeutic nanoparticle, or another therapeutic agent (e.g., bacteria, bacterial spores, bacteriophages, bacterial components, viruses (e.g., oncolytic viruses), exosomes, lipids, or ions). Non-limiting examples of oncolytic viruses include Talimogene laherparepvec, Onyx-015, GL-ONC1, CV706, Voyager-V1, and HSV-1716. Some wild-type viruses also show oncolytic behavior, such as Vaccinia virus, Vesicular stomatitis virus, Poliovirus, Reovirus, Senecavirus, ECHO-7, and Semliki Forest virus.

In some embodiments, a therapeutic DNA molecule, a therapeutic RNA molecule, a therapeutic, a therapeutic peptide, a small molecule therapeutic, or a therapeutic gene editing factor is not produced by the cytoplast. In some embodiments, a therapeutic DNA molecule, a therapeutic RNA molecule, a therapeutic, a therapeutic peptide, a small molecule therapeutic, or a therapeutic gene editing factor is packaged inside the cytoplast.

In some embodiments, the DNA molecule, the RNA molecule, the protein, the peptide, the small molecule therapeutic, and/or the gene-editing factor are recombinantly expressed. In some embodiments, the cell from which the cytoplast is derived or obtained is engineered to produce one or more of the DNA molecule, the RNA molecule, the protein, the peptide, the small molecule therapeutic, and/or the gene-editing factor. In some embodiments, the cell from which the cytoplast is derived or obtained is engineered to stably (e.g., permanently) express one or more of the DNA molecule, the RNA molecule, the protein, the peptide, the small molecule therapeutic, and/or the gene-editing factor. In some embodiments, the cell from which the cytoplast is derived or obtained is engineered to transiently express one or more of the DNA molecule, the RNA molecule, the protein, the peptide, the small molecule therapeutic, and/or the gene-editing factor. In some embodiments, the cell from which the cytoplast is derived or obtained is engineered prior to enucleation. In some embodiments, the cytoplast is engineered to transiently express one or more of the DNA molecule, the RNA molecule, the protein, the peptide, the small molecule therapeutic, and/or the gene-editing factor (e.g., engineered following enucleation).

In some embodiments, DNA molecule, the RNA molecule, the protein, the peptide, the small molecule therapeutic, and/or the gene-editing factor are not naturally expressed (i.e., in the absence of engineering) in the cell from which the cytoplast was derived or obtained (i.e., the DNA molecule, the RNA molecule, the protein, the peptide, the small molecule therapeutic, and/or the gene-editing factor are exogenous to the cytoplast). In some embodiments, the DNA molecule, the RNA molecule, the protein, the peptide, the small molecule therapeutic, and/or the gene-editing factor are not naturally expressed in the subject (i.e., the DNA molecule, the RNA molecule, the protein, the peptide, the small molecule therapeutic, and/or the gene-editing factor are exogenous to the subject). In some embodiments, the DNA molecule, the RNA molecule, the protein, the peptide, the small molecule therapeutic, and/or the gene-editing factor are not naturally expressed in the subject at the intended site of therapy (e.g., a tumor, or a particular tissue, such as the brain, the intestine, the lungs, the heart, the liver, the spleen, the pancreas, muscles, eyes, and the like) (i.e., the DNA molecule, the RNA molecule, the protein, the peptide, the small molecule therapeutic, and/or the gene-editing factor are exogenous to the intended site of therapy).

In some embodiments, the DNA molecule, the RNA molecule, the protein, the peptide, the small molecule therapeutic, and/or the gene-editing factor are naturally expressed (i.e., in the absence of engineering) in the cell from which the cytoplast was derived or obtained (i.e., the DNA molecule, the RNA molecule, the protein, the peptide, the small molecule therapeutic, and/or the gene-editing factor are innately endogenous to the cytoplast) (e.g., in the absence of engineering of the cell from which the cytoplast was derived or obtained). In some embodiments, the DNA molecule, the RNA molecule, the protein, the peptide, the small molecule therapeutic, and/or the gene-editing factor are naturally expressed in the subject (i.e., the DNA molecule, the RNA molecule, the protein, the peptide, the small molecule therapeutic, and/or the gene-editing factor are endogenous to the subject). In some embodiments, the DNA molecule, the RNA molecule, the protein, the peptide, the small molecule therapeutic, and/or the gene-editing factor are naturally expressed in the subject at the intended site of therapy (e.g., a tumor, or a particular tissue, such as the brain, the intestine, the lungs, the heart, the liver, the spleen, the pancreas, muscles, eyes, and the like) (i.e., the DNA molecule, the RNA molecule, the protein, the peptide, the small molecule therapeutic, and/or the gene-editing factor are endogenous to the intended site of therapy).

In some embodiments, therapeutic, e.g., the DNA molecule, the RNA molecule, the protein, the peptide, the small molecule therapeutic, and/or the gene-editing factor, is derived from a synthetic cell and loaded into the cytoplast.

In some embodiments, the cytoplast expresses a corrected, a truncated, or a non-mutated version and/or copy of the DNA molecule, the RNA molecule, the protein, the peptide, the small molecule therapeutic, and/or the gene-editing factor as compared to the cell from which the cytoplast was derived or obtained. In some embodiments, the cytoplast is obtained from any nucleated cell (e.g., a eukaryotic cell, a mammalian cell (e.g., a human cell, or any mammalian cell described herein), a protozoal cell (e.g., an amoeba cell), an algal cell, a plant cell, a fungal cell, an invertebrate cell, a fish cell, an amphibian cell, a reptile cell, or a bird cell).

In some embodiments, a cytoplast can produce or contain at least 2 (e.g., at least 2, 3, 4, 5, or more) different therapeutic DNA molecules, therapeutic RNA molecules, therapeutic proteins, therapeutic peptides, small molecule therapeutics, or therapeutic gene-editing factors, in any combination. For example, in some embodiments, a cytoplast can produce or contain a therapeutic DNA molecule and a small molecule therapeutic. For example, in some embodiments, a cytoplast can produce or contain two different small molecule therapeutics. For example, in some embodiments, a cytoplast can produce or contain a chemokine receptor (e.g., for targeting) and a small molecule therapeutic.

In some embodiments, the cytoplast is obtained from an immortalized cell, a cancer cell (e.g., any cancer cell) a primary (e.g., host-derived) cell, or a cell line. Any non-immortal cell can be immortalized using methods known in the art. In some embodiments, the cytoplast can be obtained from a cell autologous to the subject. In some embodiments, the cytoplast can be obtained from a cell allogenic to the subject. In some embodiments, the cytoplast is obtained from an immune cell. In some embodiments, the cytoplast is obtained from a natural killer (NK) cell, a neutrophil, a macrophage, a lymphocyte, a fibroblast, an adult stem cell (e.g., hematopoietic stem cell, a mammary stem cell, an intestinal stem cell, mesenchymal stem cell, an endothelial stem cell, a neural stem cell, an olfactory adult stem cell, a neural crest stem cell, a skin stem cell, or a testicular cell), a mast cell, a basophil, an eosinophil, or an inducible pluripotent stem cell.

In some embodiments, prior to enucleation, two or more cells (e.g., any of the cells disclosed herein) are fused by any method disclosed herein or known in the art. Enucleation of the fusion product can result in a cytoplast.

In some embodiments, a first cytoplast is fused to a cell or second cytoplast. In some embodiments, the cell is any nucleated (e.g., a mammalian cell (e.g., a human cell, or any mammalian cell described herein), a protozoal cell (e.g., an amoeba cell), an algal cell, a plant cell, a fungal cell, an invertebrate cell, a fish cell, an amphibian cell, a reptile cell, or a bird cell). In some embodiments, the second cell is a synthetic cell. Accordingly, provided are methods of altering the behavior of a cell comprising fusing the cell with any of the cytoplasts described herein. Also provided herein are methods comprising administering to a subject a therapeutically effective amount of a cell to which a cytoplast has been fused.

In some embodiments, the second cytoplast is derived from the same type of cell as the first cytoplast. In some embodiments, the second cytoplast is derived from a different type of cell as the first cytoplast. In some embodiments, the second cytoplast contains or expresses at least one therapeutic DNA molecule, therapeutic RNA molecule, therapeutic protein, therapeutic peptide, small molecule therapeutic, therapeutic gene editing factor, a therapeutic nanoparticle, or another therapeutic agent that is the same as a therapeutic DNA molecule, therapeutic RNA molecule, therapeutic protein, therapeutic peptide, small molecule therapeutic, therapeutic gene editing factor, a therapeutic nanoparticle contained in or expressed by the first cytoplast. In some embodiments, the second cytoplast contains or expresses at least one therapeutic DNA molecule, therapeutic RNA molecule, therapeutic protein, therapeutic peptide, small molecule therapeutic, therapeutic gene editing factor, a therapeutic nanoparticle, or another therapeutic agent that is different from a therapeutic DNA molecule, therapeutic RNA molecule, therapeutic protein, therapeutic peptide, small molecule therapeutic, therapeutic gene editing factor, a therapeutic nanoparticle contained in or expressed by the first cytoplast. In some embodiments, a first cytoplast can be fused to a cell or to a second cytoplast using any method known in the art, for example, electrofusion or viral fusion using viral-based cell surface peptides.

In some embodiments, the therapeutic RNA molecule is messenger RNA (mRNA), short hairpin RNA (shRNA), small interfering RNA (siRNA), microRNA, long non-coding RNA (lncRNA) or a RNA virus. In some embodiments, the therapeutic DNA molecule is single-stranded DNA, double-stranded DNA, an oligonucleotide, a plasmid, a bacterial DNA molecule or a DNA virus. In some embodiments, the therapeutic protein is a cytokine, a growth factor, a hormone, an antibody, a small-peptide based drug, or an enzyme. In some embodiments, the cytoplast transiently expresses the therapeutic DNA molecule, the therapeutic RNA molecule, the therapeutic protein, the therapeutic peptide, the small molecule therapeutic, and/or the therapeutic gene editing factor. In some embodiments, the expression of the therapeutic DNA molecule, the therapeutic RNA molecule, the therapeutic protein, the therapeutic peptide, the small molecule therapeutic, and/or the therapeutic gene editing factor is inducible. In some embodiments, a nucleated cell is permanently engineered to express the therapeutic DNA molecule, the therapeutic RNA molecule, the therapeutic protein, the therapeutic peptide, the small molecule therapeutic, and/or the therapeutic gene editing factor. In some embodiments, the expression of the therapeutic DNA molecule, the therapeutic RNA molecule, the therapeutic protein, the therapeutic peptide, the small molecule therapeutic, and/or the therapeutic gene editing factor. In some embodiments of any of the methods described herein, the cytoplast comprises a therapeutic agent or a nanoparticle. In some embodiments, the therapeutic agent is a small molecule or a bacteria or an exosome.

In some embodiments, the method further includes administering to the subject one or more additional therapies. In some embodiments, the one or more additional therapies is selected from the group consisting of: cell-based therapy, a small molecule, immuno-therapy, chemotherapy, radiation therapy, gene therapy, and surgery.

Provided herein are isolated cytoplasts (e.g., recombinant cytoplasts, or any cytoplasts described herein) comprising a therapeutic DNA molecule, a therapeutic RNA molecule, a therapeutic protein, a therapeutic peptide, a small molecule therapeutic, a therapeutic gene-editing factor a therapeutic nanoparticle and/or another therapeutic agent. In some embodiments, the therapeutic agent is a drug or chemotherapeutic or a gene editing agent.

Also provided herein are methods of making a recombinant cytoplast (e.g., any cytoplast described herein), the method comprising: enucleating a nucleated cell; and introducing into the enucleated cell an therapeutic DNA molecule, an therapeutic RNA molecule, an therapeutic protein, an therapeutic peptide, a small molecule therapeutic, a therapeutic gene-editing factor, a therapeutic nanoparticle and/or another therapeutic agent. In some embodiments, the introducing step precedes the enucleating step. In some embodiments, the enucleating step precedes the introducing step. In some embodiments, the introducing step results in a transient expression of the therapeutic DNA molecule, the therapeutic RNA molecule, the therapeutic protein, the therapeutic peptide, the small molecule therapeutic, the therapeutic gene editing factor, or the other therapeutic agent. In some embodiments, (e.g., when the introducing step precedes the enucleation step), the introducing step results in a permanent expression of the therapeutic DNA molecule, the therapeutic RNA molecule, the therapeutic protein, the therapeutic peptide, the small molecule therapeutic, the therapeutic gene editing factor, or the other therapeutic agent In some embodiments, the therapeutic RNA molecule is messenger RNA (mRNA), short hairpin RNA (shRNA), small interfering RNA (siRNA), microRNA, long non-coding RNA (lncRNA) or a RNA virus. In some embodiments, the therapeutic DNA molecule is single-stranded DNA, double-stranded DNA, an oligonucleotide, a plasmid, a bacterial DNA molecule or a DNA virus. In some embodiments, the therapeutic DNA or the therapeutic RNA is a gene therapy. In some embodiments, the therapeutic protein is an enzyme, an antibody, a toxin, cytokine, a protein hormone, a growth factor, or a vaccine. In some embodiments, a nucleated cell can be cultured (e.g., in a suspension, as adherent cells, as adherent cells in 3D (e.g., in semi-suspension or other nonadherent methods)) under various conditions (e.g., in a cytokine bath, or under hypoxic conditions) before enucleation.

Also provided herein are methods of making a recombinant cytoplast that include: transfecting a nucleated cell with a vector; and enucleating the transfected cell.

In some embodiments, the vector is a viral vector (e.g., a retrovirus vector (e.g., a lentivirus vector), an adeno-associated virus (AAV) vector, a vesicular virus vector (e.g., vesicular stomatitis virus (VSV) vector), or a hybrid virus vector). In some embodiments, a viral vector can be a cytoplasmic-replicating virus. In some embodiments, a viral vector can be a nuclear-replicating virus. In some embodiments, enucleating occurs after the vector integrates into the genome of the nucleated cell. In some embodiments, the vector is transfected after the cell is enucleated. The order of transfection and enucleation can affect the choice of vector. For example, if transfection occurs before enucleation, either a cytoplasmic-replicating virus or a nuclear-replicating virus can be an acceptable vector. For example, if transfection occurs after enucleation, a cytoplasmic-replicating virus can be a better choice of vector than a nuclear-replicating virus; on the other hand, a nuclear-replicating virus can be packaged in an enucleated cytoplast to be released upon death of the cytoplast. In some embodiments, the vector comprises a coding sequence of a therapeutic protein. In some embodiments, the therapeutic protein is an enzyme, an antibody, a toxin, cytokine, a protein hormone, a growth factor, or a vaccine.

Also provided herein are methods of treating a subject that include: administering to the subject a therapeutically effective amount of a composition comprising a cytoplast expressing a therapeutic DNA molecule, a therapeutic RNA molecule, a therapeutic protein, a therapeutic peptide, a small molecule therapeutic, and/or a therapeutic gene-editing factor. In some embodiments, a method can include administering to the subject a therapeutically effective amount of a composition comprising a naturally derived cytoplast or an engineered cytoplast expressing a therapeutic DNA molecule, a therapeutic RNA molecule, a therapeutic protein, a therapeutic peptide, a small molecule therapeutic, and/or a therapeutic gene-editing factor.

Also provided herein are methods of treating a subject that include: administering to the subject a therapeutically effective amount of a composition comprising a cytoplast containing a therapeutic DNA molecule, a therapeutic RNA molecule, a therapeutic protein, a therapeutic peptide, a small molecule therapeutic, a therapeutic gene-editing factor, a therapeutic nanoparticle, and/or another therapeutic agent.

In some embodiments, the cytoplast is obtained from a mammalian cell. In some embodiments, the cytoplast is obtained from an immune cell.

In some embodiments, the composition further includes a targeting moiety. In some embodiments, the targeting moiety is a cell surface protein.

In some embodiments, the targeting moiety is a secreted protein, or a protein that is tethered to the extracellular matrix.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIGS. 2A-D: FIG. 2A is a representative fluorescence microscopy image of cytoplasts produced from human telomerase reverse transcriptase (hTERT) adipose-derived human mesenchymal stem cells (MSC). Cells were stained with red dye (5-(and-6)-(((4-chloromethyl)benzoyl) amino) tetramethylrhodamine) (CMTMR) and nuclei were stained with Vybrant® Dyecycle™ green. Arrows point to normal nucleated cells and arrowheads point to enucleated cytoplasts. Scale bar=50 µm.

FIG. 2B is a representative fluorescence microscopy image of cytoplasts produced from HL-60 human neutrophil cells (neutrophil). Cells were stained with red dye CMTMR and nuclei were stained with Vybrant® Dyecycle™ green. Arrows point to nucleated cells and arrowheads point to enucleated cytoplasts. Scale bar=50 µm.

FIG. 2C is a representative fluorescence microscopy image of cytoplasts produced from NIH3T3 mouse fibroblast cells (fibroblast). Cells were stained with red dye CMTMR and nuclei were stained with Vybrant® Dyecycle™ green. Arrows point to nucleated cells and arrowheads point to enucleated cytoplasts. Scale bar=50 µm.

FIG. 2D is a representative fluorescence microscopy image of cytoplasts produced from human natural killer cell line NKL cells (NK). Cells were stained with green dye 5-chloromethylfluorescein diacetate (CMFDA) and nuclei were stained with 4',6-diamidino-2-phenylindole (DAPI). Arrows point to nucleated cells and arrowheads point to enucleated cytoplasts. Scale bar=50 µm.

FIG. 5A is a representative confocal microscopy image of MSC-derived cytoplasts cultured in two-dimensional (2D) glass bottom chambers, stained with rhodamine phalloidin to visualize F-actin cytoskeleton and DAPI to visualize the nuclei. Arrows point to stained cytoskeleton structures. Scale bar=50 µm.

FIG. 5B is a representative confocal microscopy image of MSCs cultured in 2D glass bottom chambers, stained with rhodamine phalloidin to visualize F-actin cytoskeleton and with DAPI to visualize the nuclei. Arrows point to stained cytoskeleton structures. Arrowheads point to nuclei. Scale bar=50 µm.

FIG. 5C is a representative confocal microscopy image of MSC-derived cytoplasts cultured in 2D glass bottom chambers, stained with anti-α-Tubulin antibody to visualize the microtubule network and DAPI to visualize the nuclei. Arrows point to stained cytoskeleton structures. Scale bar=50 µm.

FIG. 5D is a representative confocal microscopy image of MSCs cultured in 2D glass bottom chambers, stained with anti-α-Tubulin antibody to visualize the microtubule network and with DAPI to visualize the nuclei. Arrows point to stained cytoskeleton structures. Arrowheads point to nuclei. Scale bar=50 µm.

FIG. 5E is a representative confocal microscopy image of MSC-derived cytoplasts cultured in a three-dimensional (3D)-collagen matrix for 24 hours, stained with rhodamine phalloidin to visualize F-actin cytoskeleton and DAPI to visualize the nuclei. Scale bar=50 µm.

FIG. 5E' is a representative confocal microscopy image of 5E, showing the unmerged DAPI stain to visualize nuclei. Scale bar=50 µm.

FIG. 5F is a representative confocal microscopy image of MSCs cultured in 3D-collagen matrix for 24 hours, stained with rhodamine phalloidin to visualize F-actin cytoskeleton and DAPI to visualize the nuclei. Arrowheads point to nuclei. Scale bar=50 µm. µm.

FIG. 5F' is a representative confocal microscopy image of 5F, showing the umerged DAPI stain to visualize nuclei. Scale bar=50 µm.

FIG. 6A is a representative phase contrast microscopy image of MSCs cultured in full media for 16 hours, then fixed and stained with Crystal Violet. Arrowheads point to well-defined nanotubes. Scale bar=50 µm.

FIG. 6B is a representative confocal microscopy image of MSCs cultured in full media for 16 hours, then fixed and stained with the mitochondrial marker anti-apoptosis-inducing factor (AIF) and DAPI to visualize nuclei. Arrowheads point to well-defined nanotubes with prominent mitochondrial staining. Green (light gray) represents AIF-labeled mitochondria; blue (dark gray) represents DAPI-stained nuclei. Scale bar=50 µm.

FIG. 6C is a representative phase contrast microscopy image of MSC-derived cytoplasts cultured in full media for 16 hours, then fixed and stained with Crystal Violet. Arrowheads point to well-defined nanotubes. Scale bar=50 µm.

FIG. 6C' is an enlarged image of FIG. 6C. Arrowheads point to well-defined nanotubes. Scale bar=50 µm.

FIG. 6D is a representative confocal microscopy image of MSC-derived cytoplasts cultured in full media for 16 hours, then fixed and stained with the mitochondrial marker anti-AIF and DAPI to visualize nuclei. Arrowheads point to well-defined nanotubes with prominent mitochondrial staining. Green (light gray) represents AIF-labeled mitochondria; blue (dark gray) represents DAPI-stained nuclei. Scale bar=50 µm.

FIG. 6D' is an enlarged image of FIG. 6D. Scale bar=50 µm.

FIG. 7A is a representative confocal microscopy image of adipose-derived MSCs stained with the mitochondrial marker anti-AIF (light gray) and DAPI (dark gray ovals). Arrows point to mitochondria. Arrowheads point to nuclei. Scale bar=50 µm.

FIG. 7A' is a representative confocal image of MSC-derived cytoplasts stained with the mitochondrial marker anti-AIF (light gray) and DAPI (dark gray ovals). Arrows point to mitochondria. Arrowheads point to nuclei. Scale bar=50 µm.

FIG. 7B is a representative confocal microscopy image of adipose-derived MSCs stained with the lysosomal marker anti-lysosome-associated membrane protein 1 (LAMP1, light gray) and DAPI (dark gray ovals). Arrows point to lysosomes. Arrowheads point to nuclei. Scale bar=50 µm.

FIG. 7B' is a representative confocal microscopy image of MSC-derived cytoplasts stained with LAMP1 (light gray) and DAPI (dark gray ovals). Arrows point to lysosomes. Arrowheads point to nuclei. Scale bar=50 µm.

FIG. 7C is a representative confocal microscopy image of adipose-derived MSCs stained with the Golgi marker anti-receptor binding cancer antigen expressed on SiSo cells (RCAS1, light gray) and DAPI (dark gray ovals). Arrows point to Golgi. Arrowheads point to nuclei. Scale bar=50 µm.

FIG. 7C' is a representative confocal microscopy image of MSC-derived cytoplasts stained with the Golgi marker anti-RCAS1 (light gray) and DAPI (dark gray ovals). Arrows point to Golgi. Arrowheads point to nuclei. Scale bar=50 µm.

FIG. 7D is a representative confocal microscopy image of adipose-derived MSCs stained with the endoplasmic reticulum (ER) marker anti-protein disulfide isomerase (PDI, light gray) and DAPI (dark gray ovals). Arrows point to ER. Arrowheads point to nuclei. Scale bar=50 µm.

FIG. 7D' is a representative confocal microscopy image of MSC-derived cytoplasts stained with the endoplasmic reticulum (ER) marker anti-PDI (light gray) and DAPI (dark gray ovals). Arrows point to ER. Arrowheads point to nuclei. Scale bar=50 µm.

FIG. 7E is a representative confocal microscopy image of adipose-derived MSCs stained with the endosomal marker anti-early endosome antigen 1 (EEA1, light gray) and DAPI (dark gray ovals). Arrows point to lysosomes. Arrowheads point to nuclei. Scale bar=50 µm.

FIG. 7E' is a representative confocal microscopy image of MSC-derived cytoplasts stained with the endosomal marker anti-EEA1(light gray) and DAPI (dark gray ovals). Arrows point to lysosomes. Arrowheads point to nuclei. Scale bar=50 µm.

FIG. 9A-D: FIG. 9A is a representative epifluorescence microscopy image of MSCs incubated with 100 µM of the cell-permeable peptide (Arg)9-FAM (Fluorescein amidite, light gray) and stained with Hoechst 33342 (nuclei, dark gray ovals). Arrows indicate Hoechst-stained nuclei; arrowheads indicate positive (Arg)9-FAM signal.

FIG. 9B is a representative epifluorescence microscopy image of MSC-derived cytoplasts incubated with 100 μM of the cell-permeable fluorescent peptide (Arg)9-FM (light gray) and stained with Hoechst 33342 (nuclei, dark gray ovals). Arrows indicate Hoechst-stained nuclei; arrowheads indicate positive (Arg)9-FAM fluorescence.

FIG. 9C is a representative epifluorescence microscopy image of MSCs incubated with 100 μM of the chemotherapeutic drug doxorubicin (light gray) and stained with Hoechst 33342 (faint dark gray ovals). Arrows indicate Hoechst-stained nuclei.

FIG. 9D is a representative epifluorescence microscopy image of MSC-derived cytoplasts 100 μM of the chemotherapeutic drug doxorubicin (light gray) and stained with Hoechst 33342 (faint dark gray ovals). Arrowheads indicate positive doxorubicin fluorescence.

DETAILED DESCRIPTION

Figure 1:
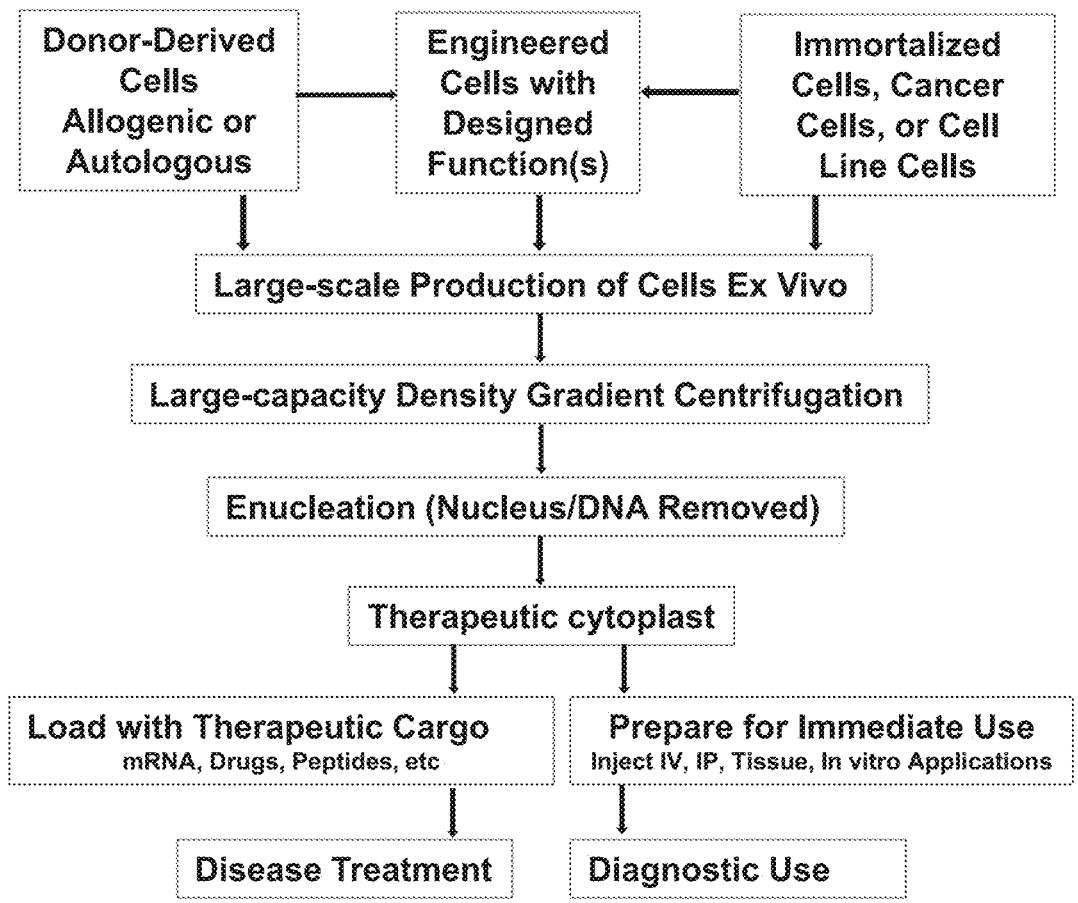
FIG. 1 is a schematic diagram of one embodiment of the disclosure in which the starting material is either donor-derived allogenic or autologous cells, or engineered cells with a designed function(s).

The present disclosure shows for the first time that cells from which the nucleus has been removed (e.g., cytoplasts), as described herein, exhibit therapeutic functions. In some embodiments, cells can be treated with cytochalasin B to soften the cortical actin cytoskeleton. The nucleus can then be physically extracted from the cell body by high-speed centrifugation in gradients of Ficoll to generate a nucleus-free (enucleated) cytoplast. Because cytoplast and intact nucleated cells sediment to different layers in the Ficoll gradient, cytoplasts can, in some embodiments, be easily isolated and prepared for therapeutic purposes or fusion to other cells (nucleated or enucleated). The enucleation process can be clinically scalable to process tens of millions of cells. Proof of concept data indicate that cytoplasts can be used as a homing vehicle to deliver clinically relevant cargos/payloads to treat healthy individuals (e.g., to improve energy, recovery from exercise, or to deliver natural products) or various diseases (e.g., any of the diseases described herein). For example, cytoplasts may be used to deliver supplements, anti-aging factors, preventative treatments, and the like to healthy individuals, e.g., individuals who have not been diagnosed with a specific disorder for which the delivered therapeutic is effective. Cytoplasts possess significant therapeutic value because they can have one or more of the following properties: remain viable for up to 14 days, do not differentiate into other cell types, secrete bioactive proteins, can physically migrate/home, can be extensively engineered ex vivo to perform specific therapeutic functions, and can be fused to the same or other cell types to transfer desirable cell functions, natural or engineered. Therefore, cytoplasts may have wide utility as a new cellular vehicle to deliver therapeutically important biomolecules, gene editing factors, and disease-targeting cargos including chemotherapeutic drugs (e.g., doxorubicin), genes, viruses, bacteria, mRNAs, shRNAs, siRNA, peptides, plasmids and nanoparticles. The present disclosure advantageously enables, in some embodiments, the generation of a safe therapeutic, as it is believed that no unwanted DNA is transferred to the subject using the cytoplasts described herein. In some embodiments, the present disclosure advantageously enables controllable therapeutics, as cell death of the cytoplasts can, in some embodiments, occur in a precise amount of time, e.g., 3-4 days. In some embodiments, the cytoplasts described herein can act as a cell-based carrier that can be genetically engineered to deliver specific gene editing, disease-fighting, and health promoting cargos to humans or animals. Finally, manufacturing significant numbers of therapeutic cells for clinical applications can be limited and expensive, thereby limiting the application of many cell-based therapies, especially in the stem cell field. Therefore, it could be beneficial to use immortalized cells (using hTERT, viruses and oncogenes) to increase manufacturing capabilities, because it can be robust and cost-effective. However, immortalized cells may cause cancer, and thus can be too dangerous for therapeutic applications. The present disclosure allows for the use of type of nucleated cell (an immortalized cell, a cancer cell (e.g., any cancer cell) a primary (e.g., host-derived) cell, or a cell line) for large-scale manufacturing in culture for therapeutic use, because they can be rendered safe by enucleation prior to administration or use.

The present disclosure provides methods to produce cell-based therapeutics that are safe and controllable in a subject, from any nucleated cell type that maintains a nucleus throughout it lifespan or does not naturally enucleate. In some embodiments, the disclosure provides methods for the removal of the cell nucleus (also called enucleation) from any nucleated cell derived (e.g., obtained) from either normal or cancer cell lines or any primary cell removed from the body including, but not limited to, commonly used therapeutic cells derived (e.g., obtained) from the immune system (e.g., natural killer (NK) cells, neutrophils, macrophages, lymphocytes, mast cells, basophils, eosinophils), stem cells (including, for example, iPSC (induced pluripotent stem cells), adult stem cells (e.g., mesenchymal stem cells), and embryonic stem cells), and fibroblasts. Cell enucleation can create a therapeutic cytoplast which is viable for a limited period of time, for example, up to 3-4 days. Therefore, the present disclosure, in some aspects, provides a new use for cytoplasts as a safe therapeutic vehicle that cannot perform one or more of the following actions: proliferate, differentiate, permanently engraft into the subject, become cancerous, or transfer nuclear-encoded DNA/genes to the subject (e.g., transfer of dangerous nuclear-encoded DNA/genes to the subject).

For cell-based therapies, FDA approval has, in some cases, rested on the evidence that cells are stable, meaning that they do not change or become dangerous once inside a subject. However, current cell products, including primary cells, irradiated cells, or "death-switch" controlled cells, still have the potential to respond to or change in the in vivo microenvironment. Importantly, current therapies can still retain the potential to transcribe new genes, which is not a controllable response in vivo. This gene transcription hampers the ability to satisfy regulatory requirements. In contrast, cytoplasts, which lack a nucleus, generally do not have the potential for new gene transcription even in very different in vivo microenvironments, and therefore are a more controlled and safer cell-based therapy.

To date, cell-based therapeutics generally use normal or engineered nucleated cells. Some cell-based therapies irradiate cells prior to subject administration in order to prevent cell proliferation and induced lethal DNA-damage. However, this approach induces mutations and produces significant amounts of reactive oxygen species that can irreversibly damage cellular proteins and DNA, which can release large amounts of damaged/mutated DNA into the body of a subject. Such products can be dangerous if they integrate into other cells and/or induce an unwanted anti-DNA immune response. Irradiated cells can also be dangerous because they can transfer their mutated DNA and genes to host cells by cell-cell fusion. Removing the entire nucleus from a cell is a less damaging and significantly safer method for limiting cellular lifespan that can preclude any introduction of nuclear DNA into a subject. Furthermore, many stem cells, such as mesenchymal stem cells (MSCs), are highly resistant to radiation-induced death, and therefore cannot be rendered safe using this method. In other cases, therapeutic cells have been engineered with a drug-inducible suicide switch to limit cellular lifespan. However, activation of the switch in vivo can require administering a subject with potent and potentially harmful drugs with unwanted side effects. While this method can induce suicide in culture cells (e.g., greater than 95%), it is expected to be inefficient when translated into the clinic. Without being bound by any particular theory, it is believed that a drug-inducible suicide switch could be an insufficient safety measure for clinical practice, since not all cells in the subject may undergo drug-induced death. Therefore, in the case of extensively engineered cells or stem cells or cancer cells, a drug-induced suicide switch could be considered dangerous or insufficient for clinical practice. Moreover, the death of a therapeutic cell can release large amounts of DNA (normal or genetically altered), which can integrate into host cells or induce a dangerous systemic anti-DNA immune response. If the cell mutates and/or loses or inactivates the suicide switch, it can become an uncontrollable mutant cell. In addition, these cells can fuse with host cells in the subject, and therefore transfer DNA (e.g., mutant DNA). Such fused cells can be dangerous because not all host cells inherit the suicide gene, but can inherit some of the therapeutic cell's genes/DNA during chromosomal reorganization and cell hybridization. In addition, for the same reason, therapeutic cells with suicide switches may not be ideal for use as cell fusion partners in vitro. Another method to limit therapeutic cell lifespan is heat-induced death that causes severe damage that terminates biological functions beneficial in therapeutic use (e.g., protein translation). Unlike cytoplasts, nucleated cell therapies and even some cells inactivated by the methods described above can still transfer DNA to the subject since they retain their nucleus and genetic material. Numerous chemicals inhibit cell proliferation and/or cause cell death prior to therapeutic use, including chemotherapeutic drugs and mitomycin C, etc. However, such drugs can have significant off-target effects that significantly damage the cell, which are unwanted for clinical applications due to high toxicities. Many anti-proliferative and death-inducing drugs do not effectively inhibit 100% of the cells due to resistance, and unlike cytoplasts, many drug effects are reversible. Thus, this approach is not suitable to prevent cell growth of immortalized or cancer cells in vivo.

The present disclosure provides methods for producing therapeutic cytoplasts with either natural or inducible expression and/or uptake of biomolecules with therapeutic functions including, but not limited to, DNA/genes (e.g., plasmids) RNA (e.g., mRNA, shRNA, siRNA, miRNA), proteins, peptides, small molecule therapeutics (e.g., small molecule drugs), gene editing components, nanoparticles, and other therapeutic agents (e.g., bacteria, bacterial spores, bacteriophages, bacterial components, viruses (e.g., oncolytic viruses), exosomes, lipids, or ions).

The present disclosure provides methods for the use of cytoplasts as a vehicle to deliver therapeutic cargos to subjects including, but not limited to, DNA/genes (e.g., plasmids), RNA (e.g., mRNA, shRNA, siRNA, miRNA), proteins, peptides, small molecule therapeutics (e.g., small molecule drugs), gene editing components, nanoparticles, and other therapeutic agents (e.g., bacteria, bacterial spores, bacteriophages, bacterial components, viruses (e.g., oncolytic viruses), exosomes, lipids, or ions).

The present disclosure provides methods for the use of cytoplasts to produce ions, molecules, compounds, complexes, or biomolecules (which can be, for example, secreted, intracellular, inducible, or a combination thereof) including, but not limited to, DNA/genes (e.g., plasmids), RNA (e.g., mRNA, shRNA, siRNA, miRNA), proteins, peptides, small molecule therapeutics (e.g., small molecule drugs), gene editing components, nanoparticles, and other therapeutic agents (e.g., bacteria, bacterial spores, bacteriophages, bacterial components, viruses, exosomes, or lipids).

The present disclosure provides methods for the largescale in vitro production of therapeutic cytoplasts derived (e.g., obtained) from any nucleated cell type (e.g., a mammalian cell (e.g., a human cell, or any mammalian cell described herein), a protozoal cell (e.g., an amoeba cell), an algal cell, a plant cell, a fungal cell, an invertebrate cell, a fish cell, an amphibian cell, a reptile cell, or a bird cell). For example, the cell can have been immortalized and/or oncogenically transformed naturally or by genetic engineering.

The present disclosure provides methods for the use of therapeutic cytoplasts (natural or engineered) as fusion partners to other cells or cytoplasts (therapeutic or natural) to enhance and/or transfer organelles and biomolecules (secreted, intracellular, and natural and inducible) including, but not limited to, mitochondria, ribosomes, endosomes, lysosomes, Golgi, DNA/genes (e.g., plasmids), RNA (e.g., mRNA, shRNA, siRNA, miRNA), proteins (e.g., cytokines, growth factors, and protein hormones), peptides, small molecule therapeutics (e.g., small molecule drugs), gene editing components, nanoparticles, and other therapeutic agents (e.g., bacteria, bacterial spores, bacteriophages, bacterial components, viruses (e.g., oncolytic viruses), exosomes, lipids, or ions).

The present disclosure provides methods for the cryopreservation, cryohibernation, storage, and recovery of therapeutic cytoplasts in vitro.

The present disclosure provides methods for the use of cytoplasts as biosensors and signal transduction indicators of biological processes and healthy or disease states.

The present disclosure, in some embodiments, enables the generation of a novel nucleus-free, cell-based product that can be used as a therapeutic and/or can be modified or genetically engineered to deliver specific disease-fighting and health-promoting cargos to human or animal subjects in a safe and controllable manner.

Development of effective cell-based therapeutics often requires genetic engineering and the introduction of new genetic material into the genome of cells ex vivo. However, this process can introduce dangerous mutations into the genome that produce cancer and other life-threatening diseases, especially if the engineered cells permanently engraft into the body or fuse with host cells. The present disclosure allows for removal of the entire nucleus (i.e. all nuclear encoded DNA) from any nucleated cell type for use as a safe therapeutic or as a vehicle to deliver a specific payload, either biological or synthetic in nature. Cytoplasts can be safer than nucleated cells because no nuclear-encoded genes or foreign or mutant DNA are transferred to the subject, thereby creating unwanted disease states and/or inducing anti-DNA immune responses. The present disclosure allows for generation of a new platform of safe, nuclear-free cell therapeutics derived from any nucleated cell type, either normal or engineered, including, but not limited to, iPSC (induced pluripotent stem cells), any immortalized cell, stem cells, primary cells (e.g., host-derived cells), cell lines, any immune cell, or cancerous cells. It is notable that the actual process of enucleation was established in the literature more than three decades ago. However, the use or development of cytoplasts as a therapeutic entity or as a vehicle to deliver any therapeutic cargo either natural or engineered to a subject has not been demonstrated to date.

A significant problem with many existing cell-based therapeutics is that after delivery to the body, the cells proliferate uncontrollably and can permanently engraft into the body, which can be life-threatening.

Also, the lack of cell control after administration to the subject can make the delivery of precise doses of therapeutic cells and their bioactive products difficult (i.e. poor pharmacokinetics). In some embodiments of the present disclosure, cytoplasts can perform many of the same biological/therapeutic functions as their nucleated counterpart, but do not proliferate or engraft permanently in the subject, since they can have a defined life span (e.g., of 1 hour to 14 days). Thus, the pharmacokinetics of cytoplast-based therapies can be definable and significantly safer with controllable and predictable responses in the subject.

In some embodiments of the present disclosure, cytoplasts can be administered to a subject beyond their defined life span (e.g. "dead" cytoplasts). For example, the death process of the administered cytoplasts can have an immunostimulatory effect on the subject.

Prior to patient or subject delivery, traditional cell-based therapeutics are commonly modified or genetically altered ex vivo to generate desirable cellular and therapeutic functions. However, when these cells are introduced into the subject, the new host environment can significantly reprogram and negatively alter, or otherwise render them ineffective. Since cytoplasts are devoid of a nucleus, there is no new gene transcription, meaning that, in some embodiments, cytoplasts cannot respond to reprogramming and detrimental external signals. Therefore, cytoplasts can retain their differentiated phenotype and ex vivo engineered therapeutic functions when introduced into the subject, making them a more controllable and predictable therapeutic vehicle. Likewise, normal donor cells that are immediately enucleated can retain their in vivo programs/attributes when transplanted into the subject. Overall, cytoplasts can be a more controllable and predictable therapeutic vehicle than traditional cell-based therapeutics because they can retain their in vitro and in vivo phenotypes and biological functions. Such properties are critically important for many therapeutic applications that rely on freshly-derived (e.g., freshly-obtained) donor cells or cells engineered ex vivo to perform specific therapeutic functions Unlike nucleated cells, nuclear-free cytoplasts can, in some embodiments, be loaded with high doses of DNA-damaging/gene targeting agents for delivery to subjects as a therapeutic against cancer or other diseases. This includes, but is not limited to, DNA-damaging chemotherapeutic drugs, DNA-integrating viruses, oncolytic viruses, and gene therapy applications/delivery including, but not limited to, cluster regularly interspaced short palindromic repeats (CRISPR), small clusters of cas (CRISPR/Cas system), and plasmids.

In some embodiments, cytoplasts can also innately produce a therapeutic effect upon administration to a subject, without the loading of any cargo into the cytoplasts. In some embodiments, cytoplasts can be therapeutic without being engineered to produce one or more therapeutics. In some embodiments, cytoplasts can be therapeutic with neither the loading of cargo into the cytoplast nor being engineered to produce one or more therapeutics. For example, an unmanipulated cytoplast itself can have therapeutic properties when delivered into a patient or subject. In some emobodiments, an unmanipulated cytoplast can produce one or more of: a therapeutic DNA molecule, a therapeutic RNA molecule, a therapeutic protein, a therapeutic peptide, a small molecule therapeutic, and/or a gene-editing factor. In some embodiments, unmanipulated cytoplasts (e.g., derived from autologous or allogenic sources) can have the ability to perform one or more of the following actions: express therapeutic surface proteins, immune stimulating antigens, or receptors, secrete cytokines, hormones, or proteins, release exosomes, shed membrane particles, be immunostimulatory through death processes or create tunneling nanotubes which can transfer mitochondria and other cell-derived biomolecules. In some embodiments, a dead cytoplast can innately produce a therapeutic effect.

In some embodiments, cytoplasts can be applied to or cultured with cells (e.g, xenocultured cells) to alter their properties. For example, in some embodiments, cytoplasts (e.g., unmanipulated cytoplasts or engineered cytoplasts) can upregulate health-promoting factors in xenocultured cells, and in some cases, the xenocultured cells can be returned to the subject from which they were taken.

Unlike nucleated cells, cytoplasts cannot undergo DNA damage-induced apoptotic death, and therefore can be used in combination with apoptotic-inducing and/or DNA toxic/targeting agents for treatment of cancer and other diseases.

Cytoplasts are smaller than their nucleated counterparts and for this reason can migrate better through small openings in the vasculature and tissue parenchyma. In addition, removing the large dense nucleus alleviates a major physical barrier allowing the cell to move freely through small openings in the vessels and tissue parenchyma. Therefore, cytoplasts can have improved bio-distribution in the body and movement into target tissues.

Unlike nucleated cells, the fusion of cytoplasts to the same or another cell type of similar or different origin generates a unique cell hybrid that lacks problematic nuclear transfer, while maintaining desirable therapeutic attributes including, but not limited to, cell surface proteins, signal transduction molecules, secreted proteins, lipids, and epigenetic changes.

Exosomes and small cellular membrane vesicles derived from therapeutic cells have been shown, in some instances, to possess therapeutic efficacy alone or as delivery vessels, but are markedly different than and can be limited as compared to cytoplasts. Similarly, red blood cells (RBCs, erythrocytes), have been hypothesized to be useful as drug delivery systems. RBCs, too, are different from cytoplasts and can have limitations as compared to cytoplasts. Unlike exosome and membrane vesicles and RBCs, cytoplasts can be viable cell-like entities that can retain many active biological processes and all cellular organelles (e.g., ER/Golgi, mitochondrial, endosome, lysosome, cytoskeleton, etc.). Thus, cytoplasts can function like nucleated cells and exhibit critical biological functions such as adhesion, tunneling nanotube formation, actin-mediated spreading (2D and 3D), migration, chemoattractant gradient sensing, mitochondrial transfer, mRNA translation, protein synthesis, and secretion of exosomes and other bioactive molecules. One or more of these functions may not be exhibited by exosomes, small cellular membrane vesicles, or RBCs. Compared to RBCs, which are derived from erythroblasts, a cytoplast can be derived from any type of nucleated cell, including, but not limited to iPSC (induced pluripotent stem cells), any immortalized cell, stem cells, primary cells (e.g., host-derived cells), cell lines, any immune cell, cancerous cells, or from any eukaryotic cell.

A limitation to development of cell-based therapeutics for clinical use can be the inability and inefficiency of producing large enough quantities of therapeutic cells, especially stem cells. To alleviate this manufacturing "bottleneck", immortalized cells (hTERT, viruses, and oncogenes) have been considered for use to increase cell production capacity in a cost-effective manner. However, immortalized cells pose a high risk for causing cancer, and thus may be too dangerous for in vivo therapeutic purposes, and are not currently approved by the Food and Drug Administration (FDA). Importantly, the present disclosure can allow for the use of immortalized cells, cancer cells (e.g., any cancer cell), primary (e.g., host-derived) cells, or a cell line for large-scale production of therapeutic cells, because such cells are enucleated prior to delivery to render them a safe therapeutic. The present disclosure also allows for generating more cells, cell lines, and/or immortalized cell from individual subjects for large-scale manufacturing and bio-banking for use in autologous or allogenic therapies (see, e.g., FIG. 1). This can greatly increase the consistency and quality control of cell-based therapeutics, which can be offered as an off-the-shelf product.

Furthermore, cytoplasts can be superior therapeutic vehicles compared to manmade synthetic nanoparticles and liposome formulations because they are derived (e.g., obtained) from cells, and thus are fully functioning cell entities (minus the nucleus), therefore exhibiting crucial physiological functions, cellular attributes/organelles, and physiological capabilities to produce bioactive molecules with reduced subject toxicity.

In some embodiments of any of the methods, cytoplasts, and compositions described herein, a nucleated cell (e.g., an eukaryotic cell, a mammalian cell (e.g., a human cell, a canine cell, a feline cell, an equine cell, a porcine cell, a primate cell, a bovine cell, an ovine cell, a rodent cell (e.g., a mouse cell, a guinea pig cell, a hamster cell, or a mouse cell)), an immune cell, or any nucleated cell described herein), is treated with cytochalasin B to soften the cortical actin cytoskeleton. The nucleus is then physically extracted from the cell body by high-speed centrifugation in gradients of Ficoll to generate a nucleus-free cytoplast. As used herein, the term "cytoplast" or "recombinant cytoplast" are used interchangeably and refer to a nucleus-free cell that was obtained from a previously nucleated cell (e.g., any cell described herein) that consists of the inner mass of a cell and the cell organelles. In some embodiments, a cytoplast can express a therapeutic DNA molecule, a therapeutic RNA molecule, a therapeutic protein, a therapeutic peptide, a small molecule therapeutic, and/or a gene-editing factor. In some embodiments, a cytoplast can contain a therapeutic DNA molecule, a therapeutic RNA molecule, a therapeutic protein, a therapeutic peptide, a small molecule therapeutic, and/or a gene-editing factor, a nanoparticle, or another therapeutic agent. In some embodiments, an empty cytoplast (e.g., a cytoplast with no exogenous components) is used as a negative control.

In some embodiments, cytoplasts can be engineered to express, for example, chemokine receptors, adhesion molecules, antigens, or other markers that can improve the homing of the cytoplasts to sites in a subject, or stimulate and/or modulate desired immune reactions. For example, a cytoplast can be engineered to express an anti-PD-L1 antibody.

In some embodiments, a nucleated cell can be cultured (e.g., in a suspension, as adherent cells, as adherent cells in 3D (e.g., in semi-suspension or other nonadherent methods)) or clonally selected/expanded before enucleation.

In some embodiments, a cytoplast has a defined life span of less than 1 hour to 14 days (e.g., less than 1 hour to 1 hour, less than 1 hour to 6 hours, 6 hours to 12 hours, 12 hours to 1 day, 1 day, 2 days, 3 days, 4 days, 5, days, 6 days, 7 days, 8 days, 9 days, 10 days, 11 days, 13 days, 14 days, 1 to 14 days, 1 to 12 days, 1 to 10 days, 1 to 9 days, 1 to 8 days, 1 to 7 days, 1 to 6 days, 1 to 5 days, 1 to 4 days, 1 to 3 days, 1 to 2 days, 2 to 14 days, 2 to 12 days, 2 to 10 days, 2 to 8 days, 2 to 7 days, 2 to 6 days, 2 to 5 days, 2 to 4 days, 2 to 3 days, 3 to 14 days, 3 to 12 days, 3 to 10 days, 3 to 8 days, 3 to 7 days, 3 to 6 days, 3 to 5 days, 3 to 4 days, 4 to 14 days, 4 to 12 days, 4 to 10 days, 4 to 8 days, 4 to 7 days, 4 to 6 days, 4 to 5 days, 4 to 7 days, 5 to 14 days, 5 to 12 days, 5 to 10 days, 5 to 8 days, 5 to 7 days, 5 to 6 days, 6 to 14 days, 6 to 12 days, 6 to 10 days, 6 to 8 days, 6 to 7 days, 7 to 14 days, 7 to 12 days, 7 to 10 days, 7 to 8 days, 8 to 14 days, 8 to 12 days, 8 to 10 days, 10 to 14 days, 10 to 12 days, 12 to 14 days, less than 14 days, less than 12 days, less than 10 days, less than 8 days, less than 7 days, less than 6 days, less than 5 days, less than 4 days, less than 3 days, less than 2 days, less than 1 day, less than 12 hours, or less than 6 hours). In some embodiments, the lifespan of a population of cytoplasts can be evaluated by determining the average time at which a portion of the cytoplast population (e.g., at least 50%, at least 60% at least 70%, at least 75%, at least 80%, at least 85%, at least 90%, at least 95%, or at least 98% of the population) is determined to be dead. Cell death can be determined by any method known in the art. In some embodiments, the viability of cytoplasts, e.g., at one or more time points, can be evaluated by determining whether morphometric or functional parameters are intact (e.g. by trypan-blue dye exclusion, evaluating for intact cell membranes, evaluating adhesion to plastics (e.g., in adherent cytoplasts), evaluating cytoplast migration, negative staining with apoptotic markers, and the like). In some embodiments, the life span of a cytoplast may be related to the life span of the cell from which it was obtained. For example, in some embodiments, a cytoplast obtained from a macrophage may live 12 to 24 hours.

In some embodiments, a cytoplast is not a naturally occurring enucleated cell. In some embodiments, a cytoplast is not obtained from a cell that naturally undergoes enucleation. In some embodiments, a cytoplast is not a cell that has been enucleated by in the body of a subject. In some embodiments, a cytoplast is not obtained from a cell that would be enucleated by in the body of a subject. In some embodiments, a cytoplast is not obtained from an erythroblast. In some embodiments, a cytoplast is obtained from a cell that maintains a nucleus over its lifespan (e.g., in the absence of manipulations such as enucleation as described herein). In some embodiments, a cytoplast is not a cell that is found in a subject as an a nucleate cell (e.g., a red blood cell (erythrocyte), a platelet, a lens cell, or an immediate nucleated precursor thereof). In some embodiments, a cytoplast includes one or more components selected from the group consisting of an endoplasmic reticulum, a Golgi apparatus, mitochondria, ribosomes, proteasomes, or spliceosomes. In some embodiments, a cytoplast is characterized by one or more of the following features: adhesion, tunneling nanotube formation, actin-mediated spreading (2D and/or 3D), migration, chemoattractant gradient sensing, mitochondrial transfer, mRNA translation, protein synthesis, and secretion of exosomes and/or other bioactive molecules. In some embodiments, a cytoplast is characterized by an ability to secrete proteins (e.g., using exosomes). In some embodiments, a cytoplast has been enucleated ex vivo. In some embodiments, a cytoplast has been enucleated in vitro. In some embodiments, a cytoplast has been physically enucleated (e.g., by centrifugation). In some embodiments, a cytoplast is an engineered enucleated cell. In some embodiments, a cytoplast is not a red blood cell. In some embodiments, a cytoplast does not contain hemoglobin. In some embodiments, a cytoplast does not have a bi-concave shape.

In some embodiments, a cytoplast is not obtained from an erythroblast. In some embodiments, a cytoplast is obtained from a cell that would not become a red blood cell (erythrocyte). In some embodiments, a cytoplast is obtained from a lymphoid progenitor cell. In some embodiments, a cytoplast is obtained from a lymphocyte. In some embodiments, a cytoplast is obtained from a mesenchymal stem cell (e.g., from bone marrow). In some embodiments, a cytoplast is obtained from an endothelial stem cell. In some embodiments, a cytoplast is obtained from a neural stem cell. In some embodiments, a cytoplast is obtained from a skin stem cell.

In some embodiments, a cytoplast is at least 1 µm in diameter. In some embodiments, a cytoplast is greater than 1 µm in diameter. In some embodiments, a cytoplast is 1-100 µm in diameter (e.g., 1-90 µm, 1-80 µm, 1-70 µm, 1-60 µm, 1-50 µm, 1-40 µm, 1-30 µm, 1-20 µm, 1-10 µm, 1-5 µm, 5-90 µm, 5-80 µm, 5-70 µm, 5-60 µm, 5-50 µm, 5-40 µm, 5-30 µm, 5-20 µm, 5-10 µm, 10-90 µm, 10-80 µm, 10-70 µm, 10-60 µm, 10-50 µm, 10-40 µm, 10-30 µm, 10-20 µm, 10-15 µm 15-90 µm, 15-80 µm, 15-70 µm, 15-60 µm, 15-50 µm, 15-40 µm, 15-30 µm, 15-20 µm). In some embodiments, a cytoplast is 10-30 µm in diameter. In some embodiments, the diameter of a cytoplast is between 5-25 µm (e.g., 5-20 µm, 5-15 µm. 5-10 µm, 10-25 µm, 10-20 µm, 10-15 µm, 15-25 µm, 15-20 µm, or 20-25 µm). In some embodiments, a cytoplast is not an exosome. Without being bound by any particular theory, it is believed that, in some cases, some cytoplasts can advantageously be small enough to allow for better biodistribution or to be less likely to be trapped in the lungs of a subject.

As used herein, the term "eukaryotic cell" refers to a cell having a distinct, membrane-bound nucleus. Such cells may include, for example, mammalian (e.g., rodent, non-human primate, or human), non-mammalian animal (e.g., fish, bird, reptile, or amphibian), invertebrate, insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. In some embodiments, the nucleated cell is a primary cell. In some embodiments, the nucleated cell is an immune cell (e.g., a lymphocyte (e.g., a T cell, a B cell), a macrophage, a natural killer cell, a neutrophil, a mast cell, a basophil, a dendritic cell, a monocyte, a myeloid-derived suppressor cell, an eosinophil). In some embodiments, the nucleated cell is a phagocyte or a leukocyte. In some embodiments, the nucleated cell is a stem cell (e.g., an adult stem cell (e.g., a hematopoietic stem cell, a mammary stem cell, an intestinal stem cell, mesenchymal stem cell, an endothelial stem cell, a neural stem cell, an olfactory adult stem cell, a neural crest stem cell, a testicular cell), an embryonic stem cell, an inducible pluripotent stem cell (iPS)). In some embodiments, the nucleated cell is a progenitor cell. In some embodiments, the nucleated cell is from a cell line. In some embodiments, the nucleated cell is a suspension cell. In some embodiments, the nucleated cell is an adherent cell. In some embodiments, the nucleated cell is a cell that has been immortalized by expression of an oncogene. In some embodiments, the nucleated cell is immortalized by the expression of human telomerase reverse transcriptase (hTERT) or any oncogene. In some embodiments, the nucleated cell is a patient or subject derived cell (e.g., an autologous patient-derived cell, or an allogenic patient-derived cell). In some embodiments, the nucleated cell is transfected with a vector (e.g., a viral vector (e.g., a retrovirus vector (e.g., a lentivirus vector), an adeno-associated virus (AAV) vector, a vesicular virus vector (e.g., vesicular stomatitis virus (VSV) vector), or a hybrid virus vector), a plasmid) before the nucleated cell is enucleated using any of the enucleation techniques described herein and known in the art.

Methods of culturing a cell (e.g., any of the cells described herein) are well known in the art. Cells can be maintained in vitro under conditions that favor growth, proliferation, viability, differentiation and/or induction of specific biological functions with therapeutic capabilities/benefits including, but not limited to, 3-dimensional culturing, hypoxic environments, culturing on defined extracellular matrix components, treatment with chemical agents, cytokines, growth factors or exposure to any exogenous agent natural or synthetic that induces a specific desirable cell response.

In some embodiments, cell therapies already used or in development can be enucleated (e.g., using any of the methods disclosed herein) to form cytoplasts. Non-limiting examples of cell therapies already used or in development include: treatment of cancer using chimeric antigen receptor engineered T cells (CAR-T), NK or macrophages; treatment of inflammatory diseases including cancer, autoimmune (Crohn's, rheumatoid arthritis, all types of arthritis, and the like), pancreatitis; regenerative medicine applications, wound healing, bone or cartilage repair, and the like; treatment of cognitive diseases such as Alzheimer's, Parkinson's, and the like; treatments of graft-vs-host disease; gene therapy (e.g., for sickle cell anemia, Severe Combined Immunodeficiency (ADA-SCID/X-SCID), cystic fibrosis, hemophilia, Duchenne's muscular dystrophy, Huntington's disease, Parkinson's, hypercholesterolemia, Alpha-1 antitrypsin, chronic granulomatous disease, Fanconi anemia, or Gaucher Disease); and treatment of infectious diseases, such as, e.g., HIV, hepatitis, malaria, and the like.

Without wishing to be bound by any particular theory, it is believed that enucleation of cell therapies already used or in development can positively affect the safety profile and/or therapeutic benefit of the cell therapy, as, for example, the cytoplasts would be less effected by the microenvironment of the subject. Further, in some embodiments, such cytoplasts can be engineered using any of the methods described herein. For example, in some embodiments, such cytoplasts can be engineered to express therapeutic DNA molecule, a therapeutic RNA molecule, a therapeutic protein, a therapeutic peptide, a small molecule therapeutic, and/or a gene-editing factor. In some embodiments, a cytoplast can contain a therapeutic DNA molecule, a therapeutic RNA molecule, a therapeutic protein, a therapeutic peptide, a small molecule therapeutic, and/or a gene-editing factor, a nanoparticle, or another therapeutic agent. In some embodiments, such a cytoplast can be engineered to express, for example, chemokine receptors, adhesion molecules, antigens, or other markers that can improve the homing of the cytoplasts to sites in a subject, or stimulate and/or modulate desired immune reactions. For example, a cytoplast can be engineered to express an anti-PD-L1 antibody.

In some embodiments of any of the compositions and methods provided herein, the cytoplast is cooled or frozen for later use. Various methods of preserving cells are known in the art, including, but not limited to, the use of a serum (e.g., Fetal Bovine Serum) and dimethyl sulfoxide (DMSO) at ultralow temperatures (frozen cryopreservation) or hibernation media for storage at 4 degrees Celsius (cryohibernation). In some embodiments of any of the compositions and methods provided herein, the cytoplast is thawed prior to use.

Various methods are known in the art that can be used to introduce a biomolecule (e.g., a RNA molecule (e.g., mRNA, miRNA, siRNA, shRNA, lncRNA), a DNA molecule (e.g., a plasmid), a protein, a gene-editing factor (e.g., a CRISPR/Cas9 gene-editing factor), a peptide, a plasmid) into a cytoplast (e.g., a cytoplast derived from any cell described herein). Non-limiting examples of methods that can be used to introduce a biomolecule into a cytoplast include: electroporation, microinjection, lipofection, transfection, calcium phosphate transfection, dendrimer-based transfection, cationic polymer transfection, cell squeezing, sonoporation, optical transfection, impalection, hydrodynamic delivery, magnetofection, and nanoparticle transfection.

In some embodiments of any of the methods and compositions described herein, introducing further includes expressing the biomolecule in a cytoplast. Various expression vectors are known in the art and can be used herein. Non-limiting examples of expression vectors are provided herein. In some embodiments, the expression vector is the vector shown in any one of FIG. 16A, FIG. 17A, FIG. 18A or FIG. 23. Various gene-editing factors are known in the art. Non-limiting examples of gene-editing factors include: CRISPR/Cas9 gene-editing, transcription activator-like effector nuclease (TALEN), and zinc finger nucleases.

In some embodiments of any of the compositions and methods provided herein, a therapeutic agent, a virus, an antibody, drug, or a nanoparticle is introduced into the cytoplasts. In some embodiments, a therapeutic DNA, a therapeutic RNA, a therapeutic protein (e.g., an enzyme, an antibody, an antigen, a toxin, cytokine, a protein hormone, a growth factor, a cell surface receptor, or a vaccine, or any therapeutic protein that is currently available or in development), a therapeutic peptide (e.g., a peptide hormone or an antigen, or any therapeutic peptide that is currently available or in development), a small molecule therapeutic (e.g., steroid, a polyketide, an alkaloid, a toxin, an antibiotic, an antiviral, an analgesic, an anticoagulant, an antidepressant, an anticancer drug, an antiepileptic, an antipsychotic, a sedative, a colchicine, a taxol, a mitomycin, emtansine, or any small molecule therapeutic that is currently available or in development), a therapeutic gene editing factor, a therapeutic nanoparticle, or another therapeutic agent (e.g., bacteria, bacterial spores, bacteriophages, bacterial components, viruses (e.g., oncolytic viruses), exosomes, lipids, or ions is introduced into the cytoplasts.

In some embodiments, the cytoplasts can be treated (e.g. stimulated with or loaded) with exosomes. In some embodiments, treatment with exosomes can be used to introduce a biomolecule, a therapeutic, a therapeutic peptide, a small molecule therapeutic, a therapeutic gene editing factor, a therapeutic nanoparticle, or another therapeutic agent (e.g., bacteria, bacterial spores, bacteriophages, bacterial components, viruses (e.g., oncolytic viruses), exosomes, lipids, or ions into the cytoplasts. In some embodiments, treatment with exosomes can be used to alter the behavior, signaling, secreted factors, or other characteristics of the cytoplasts.

The present methods include the use of cytoplasts for treating a disease (e.g., a cancer/neoplasm, an infection, an inflammatory condition, a neurological disease (e.g., a neurodegenerative disease), a degenerative disease, an autoimmune disease, a cardiovascular disease, an ischemic disease, a genetic or inherited disorder, a developmental disorder, an ophthalmologic disease, a skeletal disease, a metabolic disease, a toxicosis, an idiopathic condition, or two or more thereof), in a subject.

Non-limiting examples of cancers include: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, glioblastoma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, a solid cancer, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor. In some embodiments, a cancer may be primary (e.g., a primary tumor) or metastatic (e.g., a metastatic tumor).

Non-limiting types of infections include viral infections, bacterial infections, fungal infections, parasitic infections, and protozoal infections. Non-limiting examples of infections include *Acinetobacter* infections, Actinomycosis, African sleeping sickness (African trypanosomiasis), AIDS (Acquired immunodeficiency syndrome), Amebiasis, Anaplasmosis, Angiostrongyliasis, Anisakiasis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, Bartonellosis, Bavlisascaris infection, BK virus infection, Black *piedra*, Blastocystosis, Blastomycosis, Bolivian hemorrhagic fever, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Capillariasis, Carrion's disease, Cat-scratch disease, Cellulitis, Chagas Disease (American trypanosomiasis), Chancroid, Chickenpox, Chikungunya, *Chlamydia, Chlamydophila pneumoniae* c infection (Taiwan acute respiratory agent or TWAR), Cholera, Chromoblastomycosis, Chytridiomycosis, Clonorchiasis, Clostridum *difficile* colitis, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Desmodesmus infection, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolasis, Fasciolopsiasis, Fatal familial insomnia (FFI), Filariasis, Food poisoning by *Clostridium perfringens*, Free-living amebic infection, *Fusobacterium* infection, Gas gangrene (Clostridial myonecrosis), Geotrichosis, Gerstmann- Straussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human *ewingii* ehrlichiosis, Human granulocytic anaplasmosis (HGA), Human immnunodeficiency virus (HIV) infection, Human metapneumovirus infection, Human monocytic ehrlichiosis, Human papillomavirus (HPV) infection, Human parainfluenza virus infection, Hymenolepiasis, Epstein-Barr virus infectious mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, *Mycoplasma genitalium* infection, Mycetoma (disambiguation), Myiasis, Neonatal conjunctivitis (Ophthalmia neonatorum), Norovirus (children and babies), (New) Variant Creutzfeldt-Jakob disease (vCJD, nvCJD), Nocardiosis, Onchocerciasis (River blindness), Opisthorchiasis, Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Relapsing fever, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, *Salmonellosis*, SARS (Severe Acute Respiratory Syndrome), Scabies, Scarlet fever, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans (OLM)), Toxocariasis (Visceral Larva Migrans (VLM)), Toxoplasmosis, Trachoma, Trichinosis, Trichomoniasis, Trichuriasis (Whipworm infection), Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, Viral pneumonia, West Nile Fever, White *piedra* (Tinea blanca), Yersnia *pseudotuberculosis* infection, Yersiniosis, Yellow fever, Zika fever, and Zygomycosis.

Non-limiting examples of neurological diseases include Amyotrophic lateral sclerosis (ALS), Alzheimer's disease, Bell's palsy, brain aneurysm, brain injury, brain tumor, cerebral palsy, chronic fatigue syndrome, concussion, dementia, epilepsy, Guillain-Barré syndrome, headache, Huntington's disease migraine, multiple sclerosis, muscular dystrophy, Neuralgia, neuropathy, neuromuscular and related diseases, Parkinson's disease, psychiatric conditions (e.g., depression, obsessive-compulsive disorder), scoliosis, seizures, spinal cord injury, spinal deformity, spinal disorder (e.g., subacute combined degeneration), spine tumor, stroke, and vertigo.

Non-limiting examples of autoimmune diseases include Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes (e.g., Type I diabetes, type II diabetes, gestational diabetes), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis *nodosa*, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Ulcerative colitis (UC), Undifferentiated connective tissue disease (UCTD), Uveitis, Vasculitis, Vitiligo, Vogt-Koyanagi-Harada Disease, and Wegener's granulomatosis (or Granulomatosis with Polyangiitis (GPA)).

Non-limiting examples of cardiovascular diseases include acute myocardial infarction, heart failure, refractory angina, coronary artery disease, rheumatic heart disease, congenital heart disease, stroke, aortic aneurism and/or dissection, peripheral arterial disease, deep vein thrombosis, pulmonary embolism, tumors of the heart, vascular tumors of the brain, cardiomyopathy, heart valve diseases, and pericardial disease.

Non-limiting examples of ophthalmologic diseases include glaucoma, cataract, macular degeneration, diabetic retinopathy, strabismus, retinal detachment, uveitis, amblyopia, dry eye syndrome, keratitis, macular edema, corneal ulcer, optic neuropathy, cytomegalovirus retinitis, corneal dystrophy, hyphema, trachoma, central serous retinopathy, retinopathy of prematurity, endophthalmitis, Leber's congenital amaurosis, central retinal artery occlusion, trichiasis, papilledema, Graves' ophthalmopathy, uveal melanoma, branch retinal vein occlusion, choroideremia, and maculopathy.

Non-limiting examples of skeletal diseases include osteochondrodysplasia, achondroplasia, hypophospatasia, achondrogenesis, thanatrophoric dysplasia, osteomalacia, rickets, osteopenia, osteoporosis, Paget's disease, osteomyelitis, osteolysis, Haju-Cheney syndrome, hypertrophic pulmonary osteoarthropathy, nonossifying fibroma, pseudarthrosis, fibrous dysplasia, hyperostosis, osteocsclerosis, and pycnodysostosis.

Non-limiting examples of metabolic diseases include cystinuria, Fabry disease, galactosemia, Gaucher disease (type I), Hartnup disease, homocystinuria, Hunter syndrome, Hurler syndrome, Lesch-Nyhan syndrome, maple syrup urine disease, Maroteaux-Lamy syndrome, Morquio syndrome, Niemann-Pick disease (type A), phenylketonuria, Pompe disease, *porphyria*, Scheie syndrome, Tay-Sachs disease, tyrosinemia(hepatorenal), von Gierke disease (glycogen storage deficiency type 1A), and Wilson's disease.

In some embodiments, the subject is in need of, has been determined to be in need of, or is suspected to be in need of a cytoplast treatment. In some embodiments, the cancer can be, e.g., acute myeloid leukemia, bladder cancer, breast cancer, kidney cancer, melanoma, small cell lung cancer, non-small cell lung cancer, pancreatic cancer, or prostate cancer.

In some embodiments, a cytoplast can be used for diagnosis of a disease or condition (e.g., a cancer or a neoplasm, an infection, an inflammatory condition, a neurological disease (e.g., a neurodegenerative disease), a degenerative disease, an autoimmune disease, a cardiovascular disease, an ischemic disease, a genetic or inherited disorder, a developmental disorder, an ophthalmologic disease, a skeletal disease, a metabolic disease, a toxicosis, an idiopathic condition, or two or more thereof). Accordingly, provided herein are methods of diagnosing a subject, or determining the presence or absence of a disease or condition in a subject, comprising administering to the subject any of the cytoplasts as described herein (e.g., unmanipulated cytoplasts, or cytoplasts genetically engineered or loaded exogenously with bioreporter molecules, or with inducible bioreporter molecules) that can signify a subject's particular health, disease state, condition, or toxin level. In some embodiments, the cytoplasts and/or a molecule expressed or secreted by, or contained within, the cytoplast can operate as a bioreporter. Such bioreporters can be used in subjects or ex vivo. In some embodiments, a sample can be obtained from a subject (e.g., blood, urine, stool, or tissue (e.g., a biopsy)). In some embodiments, the cytoplasts can express or contain, e.g., colorimetric, fluorescent, luminescent, chemiluminescent or electrochemical molecules that report a measurable clinical signal. The signal can be proportional to the concentration of a chemical, physical agent, or a biomolecule (e.g. growth factors, insulin, cancer antigens, immune factors), or proportional to gene transcriptional activity, or protein translational activity in a subject or a sample from a subject.

As used herein, the term "subject" refers to any organism. For example, a subject can be a mammal, amphibian, fish, reptile, invertebrate, bird, plant, archaea, fungus, or bacteria. In some embodiments, the subject is a mammal. In some embodiments, the subject may be a rodent (e.g., a mouse, a rat, a hamster, a guinea pig), a canine (e.g., a dog), a feline (e.g., a cat), an equine (e.g., a horse), an ovine, a bovine, a porcine, a non-human primate, e.g., a simian (e.g., a monkey), an ape (e.g., a gorilla, a chimpanzee, an orangutan, a gibbon), or a human. In some embodiments of any of the methods described herein, the subject is between 0 and 120 years old (e.g., between birth and one month (e.g., a neonate), between one month and two years (e.g., an infant), between 2 years and 12 years (e.g., a child), between twelve years and sixteen years (e.g., an adolescent), between 1 and 120 years old, between 1 and 115 years old, between 1 and 110 years old, between 1 and 105 years old, between 1 and 100 years old, between 1 and 95 years old, between 1 and 90 years old between 1 and 85 years old, between 1 and 80 years old, between 1 and 75 years old, between 1 and 70 years old, between 1 and 65 years old, between 1 and 60 years old, between 1 and 50 years old, between 1 and 40 years old, between 1 and 30 years old, between 1 and 25 years old, between 1 and 20 years old, between 1 and 15 years old, between 1 and 10 years old, between 5 and 120 years old, between 5 and 110 years old, between 5 and 100 years old, between 5 and 90 years old, between 5 and 60 years old, between 5 and 50 years old, between 5 and 40 years old, between 5 and 30 years old, between 5 and 20 years old, between 5 and 10 years old, between 10 and 120 years old, between 10 and 110 years old, between 10 and 100 years old, between 10 and 90 years old, between 10 and 80 years old between 10 and 60 years old, between 10 and 50 years old, between 10 and 40 years old, between 10 and 30 years old, between 10 and 20 years, between 20 and 120 years old, between 20 and 110 years old, between 20 and 100 years old, between 20 and 90 years old, between 20 and 70 years old, between 20 and 60 years old, between 20 and 50 years old, between 20 and 40 years old, between 20 and 30 years old, between 30 and 120 years old, between 30 and 110 years old, between 30 and 100 years old, between 30 and 90 years old, between 30 and 70 years old, between 30 and 60 years, between 30 and 50 years old, between 40 and 120 years old, between 40 and 110 years old, between 40 and 100 years old, between 40 and 90 years old, between 40 and 80 years old, between 40 and 60 years old, between 40 and 50 years old, between 50 and 120 years old, between 50 and 110 years old, between 50 and 100 years old, between 50 and 90 years old, between 50 and 80 years old, between 50 and 70 years old, between 50 and 60 years old, between 60 and 120 years old, between 60 and 110 years old, between 60 and 100 years old, between 60 and 90 years old, between 60 and 80 years old, between 60 and 70 years old, between 70 and 120 years old, between 70 and 110 years old, between 70 and 100 years old, between 70 and 90 years old, between 70 and 80 years old, between 80 and 120 years old, between 80 and 110 years old, between 80 and 100 years old, between 80 and 90 years old, between 90 and 120 years old, between 90 and 110 years old, between 90 and 100 years old, between 100 and 120 years old, or between 110 and 120 years old). In some embodiments of any of the methods described herein, the subject is not yet born, e.g., in utero. In some embodiments of any of the methods described herein, the subject is at least 1 month old (e.g., at least 2 years old, at least 12 years old, at least 16 years old, or at least 18 years old). Any of the methods described herein can be used to treat a subject, e.g., a diseased subject (i.e., a subject with a disease, e.g., who has been diagnosed with a disease), or an asymptomatic subject (i.e., a subject who clinically presents as healthy, or who has not been diagnosed with a disease). As used herein, treating includes "prophylactic treatment" which means reducing the incidence of or preventing (or reducing risk of) a sign or symptom of a disease in a subject at risk for the disease, and "therapeutic treatment", which means reducing signs or symptoms of a disease, reducing progression of a disease, reducing severity of a disease, re-occurrence in a subject diagnosed with the disease. As used herein, the term "treat" means to ameliorate at least one clinical parameter of the disease, and/or to provide benefits (e.g., anti-aging, anti-scarring, wound healing, anti-depressant, anti-inflammatory, weight loss).

As used herein, "disease," "disorder," and "condition" refer to an abnormality in a subject or any deviation from a healthy state in a subject. Non-limiting examples of diseases and/or conditions include a cancer or a neoplasm, an infection, an inflammatory condition, a neurological disease (e.g., a neurodegenerative disease), a degenerative disease, an autoimmune disease, a cardiovascular disease, an ischemic disease, a genetic or inherited disorder, a developmental disorder, an ophthalmologic disease, a skeletal disease, a metabolic disease, a toxicosis, or an idiopathic condition.

In some embodiments of any of the methods provided herein, the composition is administered at least once (e.g., 2, 3, 4, 5, 6, 7, 8, 9, 10, 11, 12, 13, 14, 15, 16, 17, 18, 19, 20, 30, 40, 50, 60, 70, 80, 90, 100 times) during a period of time (e.g., every day, every 2 days, twice a week, once a week, every week, three times per month, two times per month, one time per month, every 2 months, every 3 months, every 4 months, every 5 months, every 6 months, every 7 months, every 8 months, every 9 months, every 10 months, every 11 months, once a year). Also contemplated are monthly treatments, e.g., administering at least once per month for at least 1 month (e.g., at least two, at least three, at least four, at least five, at least six or more months, e.g., 12 or more months), and yearly treatments (e.g., administration once a year for one or more years). Administration can be via any route known in the art, e.g., subcutaneous, intravenous, arterial, ocular, oral, intramuscular, intranasal (e.g., inhalation), intraperitoneal, topical, mucosal, epidural, sublingual, epicutaneous, extra-amniotic, inter-articular, intradermal, intraosseous, intrathecal, intrauterine, intravaginal, intravesical, intravitreal, perivascular, and/or rectal administration, or any combination of known administration methods.

In some embodiments, the death process of cytoplasts can have a therapeutic effect on a subject. For example, in some embodiments, the death process of cytoplasts can be immunostimulatory. Accordingly, provided herein are methods of administering cytoplasts to a subject, wherein the death of the cytoplasts has a therapeutic effect on the subject. In some embodiments, the cytoplasts administered to the subject are dead. In some embodiments, the cytoplasts administered to the subject, when administered, have a remaining life span of less than 5 days (e.g., less than 4 days, less than 3 days, less than 2 days, less than 36 hours, less than 1 day, less than 18 hours, less than 12 hours, less than 6 hours, less than 2 hours, or less than 1 hour).

In some embodiments, cells can be removed from a subject and enucleated. In some embodiments, the cells are engineered (e.g., to produce or contain a therapeutic DNA molecule, a therapeutic RNA molecule, a therapeutic protein, a therapeutic peptide, a small molecule therapeutic, a therapeutic gene-editing factor a therapeutic nanoparticle and/or another therapeutic agent) before being enucleated. In some embodiments, cells from a subject are enucleated, and then engineered (e.g., to produce or contain a therapeutic DNA molecule, a therapeutic RNA molecule, a therapeutic protein, a therapeutic peptide, a small molecule therapeutic, a therapeutic gene-editing factor a therapeutic nanoparticle and/or another therapeutic agent). In some embodiments, the cytoplasts (whether or not they have been engineered) are administered to the subject from which the cells were removed.

In some embodiments, the media in which the cytoplasts were cultured and/or stored (a "conditioned media") can have a therapeutic benefit. In some embodiments, the media in which cytoplasts were co-cultured and/or stored (e.g., after enucleation) with cells (a "conditioned media") can have a therapeutic benefit. In some embodiments, the media in which cytoplasts fused with cells were cultured and/or stored with cells (a "conditioned media") can have a therapeutic benefit.

Accordingly, provided herein are methods of treating, preventing, or prophylactically treating, or promoting health in a subject comprising administering to the subject conditioned media. Without being bound by any particular theory, it is believed that, in some embodiments, the therapeutic benefit of cultured media can be due to the presence in the media of exosomes (e.g., containing therapeutic protein) secreted by the cytoplasts.

In some embodiments of any of the methods provided herein, the composition is administered with one or more additional therapies (e.g., any drug (e.g., antibiotics, antivirals, anti-inflammatory medications) or chemotherapy (e.g., a chemotherapeutic agent (e.g., doxorubicin, paclitaxel, cyclophosphamide), or any of the small molecule therapeutics described herein), cell-based therapy, radiation therapy, immunotherapy, a small molecule, an inhibitory nucleic acid (e.g., antisense RNA, antisense DNA, miRNA, siRNA, lncRNA), an exosome-based therapy, gene therapy or surgery).

In some embodiments provided herein, the composition further includes one or more additional therapies (e.g., any drug (e.g., antibiotics, antivirals) or chemotherapy (e.g., a chemotherapeutic agent (e.g., doxorubicin, paclitaxel, cyclophosphamide)), cell-based therapy, radiation therapy, immunotherapy, a small molecule, an inhibitory nucleic acid (e.g., antisense RNA, antisense DNA, miRNA, siRNA, lncRNA) or surgery).

Also, provided herein are compositions (e.g., pharmaceutical compositions) that include a cytoplast (e.g., a cytoplast obtained from any cell described herein). In some embodiments, the compositions are formulated for different routes of administration (e.g., intravenous, subcutaneous, intramuscular, retro-orbital, intraperitoneal). In some embodiments, the compositions can include a pharmaceutically acceptable carrier (e.g., phosphate buffered saline).

For the systemic administration of therapeutic cells, there are two major problems for their successful homing to the diseased tissues. First, most of the cells may be trapped in the small capillaries in the lung or other tissues, which may also cause serious side effects such as pulmonary embolism. Cytoplasts are, in some embodiments, much smaller than their parental cells (e.g., about 60% of the diameter of parental cells and 1/8 the volume) and do not have the rigid nucleus, therefore, cytoplasts can pass better through small capillaries and vessels than their parental cells. Second, the specific homing of cells to the diseased tissues can depend on the chemokine receptor signaling such as SDF-1α/CXCR4, CCL2/CCR2, and the adhesion molecules such as PSGL-1. As shown herein, cytoplasts can be engineered to specifically express functional CXCR4, CCR2 as well as glycosylated PSGL-1, which can greatly promote the specific homing of the engineered cytoplasts.

In some embodiments, the cytoplasts can further include (e.g. by engineering or from the cell from which they were obtained) a targeting moiety that is expressed on the cell surface of the cytoplast, e.g., CXCR4, CCR2 or PSGL-1. Non-limiting examples of cell surface proteins that may be expressed on the cell surface of the cytoplast include: chemokines such as CXCR4, CCR2, CCR1, CCR5, CXCR7, CXCR2, and CXCR1. In some embodiments, the cytoplasts can further include (e.g. by engineering or from the cell from which they were obtained) a cell targeting moiety that is secreted by the cytoplasts, or is tethered to the extracellular matrix, e.g., SDF1α or CCL2. Non-limiting examples of proteins that may be secreted by the cytoplast for cell homing include: SDF1α, CCL2, CCL3, CCL5, CCL8, CCL1, CXCL9, CXCL10, CCL11 and CXCL12. In some embodiments, the cytoplasts can further include (e.g. by engineering or from the cell from which they were obtained) a surface marker that aids in their evasion of the subject immune system. For example, in some embodiments, the cytoplasts can include a CD47 marker. Without being bound by any particular theory, it is believed that a CD47 marker helps to prevent the cytoplasts from being phagocytosed by macrophages. Non-limiting examples of cell-matrix receptors and cell-cell adhesion molecules include integrins, cadherins, glycoproteins, and heparin sulfate proteoglycans. Non-limiting examples of therapeutic molecules include tumor antigens and immunomodulatory peptides, polyamines, and ATP.

In some embodiments, the cytoplasts can be stored at a temperature between about −80° C. and about 16° C. (e.g., about −80° C. and about 12° C., −80° C. and about 10° C., about −80° C. and about 8° C., about −80° C. and about 6° C., about −80° C. and about 4° C., about −80° C. and about 2° C., about −80° C. and about 0° C., about −80° C. and about −4° C., about −80° C. and about −10° C., about −80° C. and about −16° C., about −80° C. and about −20° C., about −80° C. and about −25° C., about −80° C. and about −30° C., about −80° C. and about −35° C., about −80° C. and about −40° C., about −80° C. and about −45° C., about −80° C. and about −50° C., about −80° C. and about −55° C., about −80° C. and about −60° C., about −80° C. and about −65° C., about −80° C. and about −70° C., about −60° C. and about 16° C., about −60° C. and about 12° C., about −60° C. and about 10° C., about −60° C. and about 8° C., about −60° C. and about 6° C., about −60° C. and about 4° C., about −60° C. and about 2° C., about −60° C. and about 0° C., about −60° C. and about −4° C., about −60° C. and about −10° C., about −60° C. and about −10° C., about −60° C. and about −16° C., about −60° C. and about −20° C., about −60° C. and about −25° C., about −60° C. and about −30° C., about −60° C. and about −35° C., about −60° C. and about −40° C., about −60° C. and about −50° C., about −50° C. and about 16° C., about −50° C. and about 12° C., about −50° C. and about 10° C., about −50° C. and about 8° C., about −50° C. and about 6° C., about −50° C. and about 4° C., about −50° C. and about 2° C., about −50° C. and about 0° C., about −50° C. and about −4° C., about −50° C. and about −10° C., about −50° C. and about −16° C., about −50° C. and about −20° C., about −50° C. and about −30° C., about −50° C. and about −40° C., about −20° C. and about 16° C., about −20° C. and about 12° C., about −20° C. and about 10° C., about −20° C. and about 8° C., about −20° C. and about 6° C., about −20° C. and about 4° C., about −20° C. and about 2° C.,-about 20° C. and about 0° C., about −20° C. and about −4° C., about −20° C. and about −10° C., about −20° C. and about −15° C., about −10° C. and about 16° C., about −10° C. and about 12° C., about −10° C. and about 10° C., about −10° C. and about 8° C., about −10° C. and about 6° C., about −10° C. and about 4° C., about −10° C. and about 2° C., about −10° C. and about 0° C., about −10° C. and about −4° C., about −10° C. and about −6° C., about −4° C. and about 16° C., about −4° C. and about 10° C., about −4° C. and about 6° C., about −4° C. and about 4° C., about −4° C. and about 2° C., about −4° C. and about 0° C., about −2° C. and about 16° C., about −2° C. and about 12° C., about −2° C. and about 10° C., about −2° C. and about 6° C., about −2° C. and about 4° C., about −2° C. and about 2° C., about −2° C. and about 0° C., about 0° C. and about 16° C., about 0° C. and about 14° C., about 0° C. and about 12° C., about 0° C. and about 10° C., about 0° C. and about 8° C., about 0° C. and about 6° C., about 0° C. and about 4° C., about 2° C. and about 16° C., about 2° C. and about 12° C., about 2° C. and about 10° C., about 2° C. and about 8° C., about 2° C. and about 6° C., about 2° C. and about 4° C., about 4° C. and about 16° C., about 4° C. and about 12° C., about 4° C. and about 6° C., about 4° C. and about 10° C., about 4° C. and about 8° C., about 4° C. and about 6° C., about 6° C. and about 16° C., about 6° C. and about 12° C., about 6° C. and about 10° C., about 6° C. and about 8° C., about 8° C. and about 16° C., about 8° C. and about 12° C., about 8° C. and about 10° C., about 10° C. and about 16° C., about 10° C. and about 12° C., or about 12° C. and about 16° C.) for about 1 day to about 7 days (e.g., about 1 day to about 6 days, about 1 day to about 5 days, about 1 day to about 4 days, about 1 day to about 3 days, about 1 day to about 2 days, about 2 days to about 7 days, about 2 days to about 6 days, about 2 days to about 5 days, about 2 days to about 4 days, about 2 days to about 3 days, about 3 days to about 7 days, about 3 days to about 6 days, about 3 days to about 5 days, about 3 days to about 4 days, about 4 days to about 7 days, about 4 days to about 6 days, about 4 days to about 5 days, about 5 days to about 7 days, about 5 days to about 6 days, or about 6 days to about 7 days).

Also, provided herein are kits that include any composition described herein. For example, a kit can include instructions for using any of the compositions or methods described herein. In some embodiments, the kits can include at least one dose of any of the compositions described herein.

A number of embodiments have been described. Nevertheless, it will be understood that various modifications may be made without departing form the spirit and scope of the invention.

EXEMPLARY EMBODIMENTS

Embodiment 1 is a method comprising:
  administering to a subject a therapeutically effective amount of a composition comprising a first cytoplast expressing or containing one or more molecules selected from the group consisting of: a therapeutic DNA molecule, a therapeutic RNA molecule, a therapeutic protein, a therapeutic peptide, a small molecule therapeutic, and a therapeutic gene-editing factor.
Embodiment 2 is the method of embodiment 1, wherein the first cytoplast is obtained from a cell selected from the group consisting of a mammalian cell a protozoal cell, an algal cell, a plant cell, a fungal cell, an invertebrate cell, a fish cell, an amphibian cell, a reptile cell, or a bird cell.
Embodiment 3 is the method of embodiment 2, wherein the cell is or is derived from a cell harvested from the subject.
Embodiment 4 is the method of any one of embodiments 2 to 3, wherein the cell is or is derived from a cell line, an immortalized cell, or a cancer cell.
Embodiment 5 is the method of any one of embodiments 1 to 4, wherein the first cytoplast is obtained from an immune cell.
Embodiment 6 is the method of any one of embodiments 1 to 5, wherein the first cytoplast is obtained from a cell selected from the group consisting of a natural killer (NK) cell, a neutrophil, a macrophage, an eosinophil, a basophil, a dendritic cell, and a lymphocyte.
Embodiment 7 is the method of any one of embodiments 1 to 4, wherein the first cytoplast is obtained from a cell selected from the group consisting of a hematopoietic stem cell, a mammary stem cell, an intestinal stem cell, a mesenchymal stem cell, an endothelial stem cell, a neural stem cell, an olfactory adult stem cell, a neural crest stem cell, a skin stem cell, a testicular cell, an embryonic stem cell, a fibroblast, or an inducible pluripotent stem cell.
Embodiment 8 is the method of any one of embodiments 1 to 7, wherein the first cytoplast is fused to a second cytoplast.
Embodiment 9 is the method of embodiment 8, wherein the second cell is obtained from a cell selected from the group consisting of a mammalian cell a protozoal cell, an algal cell, a plant cell, a fungal cell, an invertebrate cell, a fish cell, an amphibian cell, a reptile cell, or a bird cell.
Embodiment 10 is the method of any one of embodiments 1 to 9, wherein the therapeutic RNA molecule is messenger RNA (mRNA), short hairpin RNA (shRNA), small interfering RNA (siRNA), microRNA, long non-coding RNA (lncRNA) or a RNA virus.
Embodiment 11 is the method of any one of embodiments 1 to 10, wherein the therapeutic DNA molecule is single-stranded DNA, double-stranded DNA, an oligonucleotide, a plasmid, a bacterial DNA molecule or a DNA virus.
Embodiment 12 is the method of any one of embodiments 1 to 11, wherein the therapeutic protein is an enzyme, an antibody, an antigen, a toxin, cytokine, a protein hormone, a growth factor, a cell surface receptor, or a vaccine.
Embodiment 13 is the method of embodiment any one of embodiments 1 to 12, wherein the cytoplast transiently expresses the therapeutic DNA molecule, the therapeutic RNA molecule, the therapeutic protein, the therapeutic peptide, the small molecule therapeutic, and/or the therapeutic gene editing factor.
Embodiment 14 is the method of any one of embodiments 1 to 12, wherein the expression of therapeutic DNA molecule, the therapeutic RNA molecule, the therapeutic protein, the therapeutic peptide, small molecule therapeutic, and/or the therapeutic gene editing factor is inducible.
Embodiment 15 is the method of any one of embodiments 1 to 14, wherein the peptidic therapeutic is selected from the group consisting of a peptide hormone and an antigen.
Embodiment 16 is the method of any one of embodiments 1 to 15, wherein the small molecule therapeutic is selected from the group consisting of steroid, a polyketide, an alkaloid, a toxin, an antibiotic, an antiviral, an analgesic, an anticoagulant, an antidepressant, an anticancer drug, an antiepileptic, an antipsychotic, a sedative, a colchicine, a taxol, a mitomycin, emtansine, or any small molecule therapeutic that is currently available or in development.
Embodiment 17 is the method of any one of embodiments 1 to 16, wherein the cytoplast contains a small molecule therapeutic or a therapeutic nanoparticle.
Embodiment 18 is the method of any one of embodiments 1-16, wherein the cytoplast contains a therapeutic agent selected from the group consisting of bacteria, bacterial spores, bacteriophages, bacterial components, viruses, exosomes, lipids, and ions.
Embodiment 19 is the method of embodiment 18, wherein the viruses are oncolytic viruses.
Embodiment 20 is the method of any one of embodiments 1 to 15 or 17 to 19, wherein the small molecule therapeutic is selected from the group consisting of an anticancer drug, an antibiotic, or an antiviral.
Embodiment 21 is the method of any one of embodiments 1 to 19, further comprising administering to the subject one or more additional therapies.
Embodiment 22 is the method of embodiment 20, wherein the one or more additional therapies is selected from the group consisting of: cell-based therapy, a small molecule, immuno-therapy, chemotherapy, radiation therapy, gene therapy, and surgery.
Embodiment 23 is the method of any one of embodiments 1 to 21, wherein the first cytoplast expresses an immune system-evading moiety.
Embodiment 24 is the method of embodiment 23, wherein the immune-system evading moiety is CD47.
Embodiment 25 is the method of any one of embodiments 1 to 24, wherein the first cytoplast or cell from which the first cytoplast is obtained has been engineered to express the therapeutic DNA molecule, the therapeutic RNA molecule, the therapeutic protein, the therapeutic peptide, the non-peptide therapeutic, and/or the therapeutic gene editing factor.
Embodiment 26 is the method of any one of embodiments 1 to 24, wherein the first cytoplast or cell from which the first cytoplast is obtained has not been engineered to express any of the therapeutic DNA molecule, the therapeutic RNA molecule, the therapeutic protein, the therapeutic peptide, the non-peptide therapeutic, and/or the therapeutic gene editing factor.

Embodiment 27 is the method of any one of embodiments 1 to 26, wherein the composition further includes a targeting moiety.

Embodiment 28 is the method of embodiment 27, wherein the targeting moiety is a cell surface protein.

Embodiment 29 is the method of embodiment 27, wherein the targeting moiety is a secreted protein or a protein that is tethered to the extracellular matrix.

Embodiment 30 is the method of any one of embodiments 1 to 26, wherein the cytoplast further comprise a targeting moiety.

Embodiment 31 is the method of embodiment 30, wherein the targeting moiety is a cell surface protein.

Embodiment 32 is the method of embodiment 30, wherein the targeting moiety is a secreted protein or a protein that is tethered to the extracellular matrix.

Embodiment 33 is a cytoplast comprising at least one therapeutic agent.

Embodiment 34 is the cytoplast of embodiment 33 wherein the therapeutic agent is a therapeutic DNA molecule, a therapeutic RNA molecule, a therapeutic protein, a therapeutic peptide, a small molecule therapeutic, or a therapeutic gene editing factor.

Embodiment 35 is the cytoplast of embodiment 34, wherein the therapeutic RNA molecule is messenger RNA (mRNA), short hairpin RNA (shRNA), small interfering RNA (siRNA), microRNA, long non-coding RNA (lncRNA) or a RNA virus.

Embodiment 36 is the cytoplast of any one of embodiments 34 to 35, wherein the therapeutic DNA molecule is single-stranded DNA, double-stranded DNA, an oligonucleotide, a plasmid, a bacterial DNA molecule or a DNA virus.

Embodiment 37 is the cytoplast of any one of embodiments 34 to 36, wherein the therapeutic protein is an enzyme, an antibody, an antigen, a toxin, cytokine, a protein hormone, a growth factor, a cell surface receptor, or a vaccine.

Embodiment 38 is the cytoplast of any one of embodiments 34 to 37, wherein the peptidic therapeutic is selected from the group consisting of a peptide hormone and an antigen.

Embodiment 39 is the cytoplast of any one of embodiments 34 to 38, wherein the small molecule therapeutic is selected from the group consisting of a steroid, a polyketide, an alkaloid, a toxin, an antibiotic, an antiviral, an analgesic, an anticoagulant, an antidepressant, an anticancer drug, an antiepileptic, an antipsychotic, a sedative, a colchicine, a taxol, a mitomycin, emtansine, or any small molecule therapeutic that is currently available or in development.

Embodiment 40 is the cytoplast of any one of embodiments 33 to 38, wherein the therapeutic agent is selected from the group consisting of a nanoparticle, bacteria, bacterial spores, bacteriophages, bacterial components, viruses, exosomes, lipids, and ions.

Embodiment 41 is the cytoplast of embodiment 40, viruses are oncolytic viruses.

Embodiment 42 is the cytoplast of any one of embodiments 33 to 41, wherein the small molecule therapeutic is selected from the group consisting of an anticancer drug, an antibiotic, or an antiviral.

Embodiment 43 is the cytoplast of any one of embodiments 33 to 43, wherein the cytoplast further comprises an immune system-evading moiety.

Embodiment 44 is the cytoplast of embodiment 43, wherein the immune system-evading moiety is CD47.

Embodiment 45 is a method of making a cytoplast, the method comprising:
introducing into a cell a therapeutic DNA molecule, a therapeutic RNA molecule, a therapeutic protein, a therapeutic peptide, a small molecule therapeutic, a therapeutic gene editing factor, an other therapeutic agent, and/or a therapeutic nanoparticle; and
enucleating the cell.

Embodiment 46 is the method of embodiment 45, wherein the introducing step precedes the enucleating step.

Embodiment 47 is the method of embodiment 46, wherein the introducing step results in a permanent expression of the therapeutic DNA molecule, the therapeutic RNA molecule, the therapeutic protein, the therapeutic peptide, the small molecule therapeutic, and/or the therapeutic gene editing factor.

Embodiment 48 is the method of embodiment 45, wherein the enucleation step precedes the introducing step.

Embodiment 49 is the method of any one of embodiments 45, 46, or 48, wherein the introducing step results in a transient expression of the therapeutic DNA molecule, the therapeutic RNA molecule, the therapeutic protein, the therapeutic peptide, the small molecule therapeutic, and/or the therapeutic gene editing factor.

Embodiment 50 is the method of any one of embodiments 45 to 49, wherein the therapeutic RNA molecule is messenger RNA (mRNA), short hairpin RNA (shRNA), small interfering RNA (siRNA), microRNA, long non-coding RNA (lncRNA) or a RNA virus.

Embodiment 51 is the method of any one of embodiments 45 to 50, wherein the therapeutic DNA molecule is single-stranded DNA, double-stranded DNA, an oligonucleotide, a plasmid, a bacterial DNA molecule or a DNA virus.

Embodiment 52 is the method of any one of embodiments 45 to 51, wherein the therapeutic protein is an enzyme, an antibody, an antigen, a toxin, cytokine, a protein hormone, a growth factor, a cell surface receptor, or a vaccine.

Embodiment 53 is the method of any one of embodiments 45 to 52, wherein the peptidic therapeutic is selected from the group consisting of a peptide hormone and an antigen.

Embodiment 54 is the method of any one of embodiments 45 to 53, wherein the small molecule therapeutic is selected from the group consisting of a steroid, a polyketide, an alkaloid, a toxin, an antibiotic, an antiviral, an analgesic, an anticoagulant, an antidepressant, an anticancer drug, an antiepileptic, an antipsychotic, a sedative, a colchicine, a taxol, a mitomycin, emtansine, or any small molecule therapeutic that is currently available or in development.

Embodiment 55 is the method of any one of embodiments 45 to 54, wherein the cytoplast further comprises a therapeutic nanoparticle.

Embodiment 56 is the method of any one of embodiments 45 to 54, wherein the cytoplast further comprises a therapeutic agent selected from the group consisting of bacteria, bacterial spores, bacteriophages, bacterial components, viruses, exosomes, lipids, and ions.

Embodiment 57 is the method of embodiment 56, wherein the viruses are oncolytic viruses.

Embodiment 58 is the method of any one of embodiments 45 to 57, wherein introducing comprises transfecting.

Embodiment 59 is the method of any one of embodiments 45 to 58, wherein introducing comprises electroporating, microinjecting, cell squeezing, sonoporating, impalecting, or hydrodynamic delivery.

Embodiment 60 is a method of making a cytoplast, the method comprising:
  transfecting a cell with a vector; and
  enucleating the cell.

Embodiment 61 is the method of embodiment 60, wherein the transfecting step precedes the enucleating step.

Embodiment 62 is the method of embodiment 61, wherein the enucleating occurs after the vector integrates into the genome of the cell.

Embodiment 63 is the method of embodiment 60, wherein the enucleating step precedes the transfecting step.

Embodiment 64 is the method of any one of embodiments 60 to 63, wherein the vector is a viral vector.

Embodiment 65 is the method of embodiment 64, wherein the viral vector is a retrovirus vector, an adeno-associated virus (AAV) vector, a vesicular virus vector, or a hybrid virus vector.

Embodiment 66 is the method of any one of embodiments 60 to 65, wherein the vector comprises a coding sequence of a therapeutic protein.

Embodiment 67 is the method of embodiment 66, wherein the therapeutic protein is an enzyme, an antibody, an antigen, a toxin, cytokine, a protein hormone, a growth factor, a cell surface receptor, or a vaccine.

Embodiment 68 is a method of making a cytoplast comprising:
  enucleating a cell.

Embodiment 69 is the method of embodiment 68, wherein the cell is not an erythroblast.

Embodiment 70 is the method of embodiment 68 or embodiment 69, wherein enucleating comprises centrifugation.

Embodiment 71 is a method of treating a subject comprising:
  administering to the subject a therapeutically effective amount of a cytoplast of any one of embodiments 33 to 44.

Embodiment 72 is a method of treating a subject comprising:
  administering to the subject a therapeutically effective amount of a cytoplast.

Embodiment 73 is the method of embodiment 72, wherein the cytoplast is not obtained from an erythroblast.

Embodiment 74 is a method comprising:
  making a cytoplast by the method of any one of embodiments 45 to 70; and
  storing the cytoplast.

Embodiment 75 is the method of embodiment 74, wherein storing comprises cryopreservation.

Embodiment 76 is the method of embodiment 74, wherein storing comprises cryohibernation.

Embodiment 77 is a method comprising:
  culturing cells in a media;
  stimulating the cells; and
  enucleating the cells to form cytoplasts.

Embodiment 78 is the method of embodiment 77, wherein culturing comprises one or more of: 3D culturing, adherent culturing, suspension culturing, and semi-suspension culturing.

Embodiment 79 is the method of any one of embodiments 77 to 78, wherein stimulating the cells comprises one or more of: adding one or more drugs to the media, adding one or more antibodies to the media, adding one or more exosomes to the media, adding one or more chemokines to the media, adding one or more cytoplasts to the media, culturing under 2D or 3D conditions, or culturing under hypoxic conditions.

Embodiment 80 is the method of any one of embodiments 77 to 80, further comprising separating the cells or the cytoplasts from the media.

Embodiment 81 is a method comprising:
  culturing cells in a media; and
  stimulating the cells, wherein stimulating the cells comprises adding one or more cytoplasts to the media.

Embodiment 82 is the method of embodiment 81, wherein culturing comprises one or more of: 3D culturing, adherent culturing, suspension culturing, and semi-suspension culturing.

Embodiment 83 is the method of any one of embodiments 81 to 82, wherein stimulating the cells further comprises one or more of: adding one or more drugs to the media, adding one or more antibodies to the media, adding one or more exosomes to the media, adding one or more chemokines to the media, culturing under 2D or 3D conditions, or culturing under hypoxic conditions.

Embodiment 84 is the method of any one of embodiments 81 to 83, further comprising separating the cells from the media.

Embodiment 85 is the method of any one of embodiments 81 to 84, further comprising enucleating the cells to form cytoplasts.

Embodiment 86 is a method of treating a subject comprising:
  administering a therapeutically effective amount of a media prepared by the method of embodiment 80 or embodiment 84 to the subject.

Embodiment 87 is a method of treating a subject comprising:
  administering a therapeutically effective amount of the cytoplasts prepared by the method of embodiment 80 or embodiment 86 to the subject.

Embodiment 88 is use of the cytoplasts of any one of embodiments 33 to 44 in the manufacture of a medicament for the treatment of a cancer, an infection, a neurological disease, a degenerative disease, an autoimmune disease, a cardiovascular disease, an ophthalmologic disease, a skeletal disease, a metabolic disease, or two or more thereof Embodiment 89 is use of a media prepared by the method of embodiment 80 or embodiment 84 in the manufacture of a medicament for the treatment of a cancer, an infection, a neurological disease, a degenerative disease, an autoimmune disease, a cardiovascular disease, an ophthalmologic disease, a skeletal disease, a metabolic disease, or two or more thereof.

Embodiment 90 is a method of determining the presence or absence of a disease or condition in a subject comprising: administering cytoplasts to the subject.

Embodiment 91 is the method of embodiment 90, wherein the disease or condition is a cancer, an infection, an inflammatory condition, a neurological disease, a degenerative disease, an autoimmune disease, a cardiovascular disease, an ischemic disease, a genetic or inherited condition, a developmental condition, an ophthalmologic disease, a skeletal disease, a metabolic disease, a toxicosis, idiopathic disease, or two or more thereof.

Embodiment 92 is the method of any one of embodiments 90 to 91, wherein the cytoplasts express or contain a reporter molecule or reagent.

Embodiment 93 is the method of embodiment 92, wherein the reporter molecule or reagent is a bioreporter molecule or reagent.

Embodiment 94 is a cell fusion product comprising:
 a first cytoplast, wherein the first cytoplast is the cytoplast of any one of embodiments 33-44; and
 a cell or second cytoplast.

Embodiment 95 is a method of determining the presence or absence of a disease or condition in a subject comprising:
 obtaining a sample from a subject; and
 adding cytoplasts to the sample.

Embodiment 96 is the method of embodiment 95, wherein the disease or condition is a cancer, an infection, an inflammatory condition, a neurological disease, a degenerative disease, an autoimmune disease, a cardiovascular disease, an ischemic disease, a genetic or inherited condition, a developmental condition, an ophthalmologic disease, a skeletal disease, a metabolic disease, a toxicosis, idiopathic disease, or two or more thereof.

Embodiment 97 is the method of any one of embodiments 95 to 96, wherein the cytoplasts express or contain a reporter molecule or reagent.

Embodiment 98 is the method of embodiment 97, wherein the reporter molecule or reagent is a bioreporter molecule or reagent.

EXAMPLES

The disclosure is further described in the following examples, which do not limit the scope of the disclosure described in the claims.

Example 1—Successful Enucleation and Survival of Mammalian Cells

As shown in FIG. 1, therapeutic cytoplasts can be generated from allogenic or autologous donor-derived cells, and can be used for disease treatment as well as for diagnostics. As a proof of concept, the enucleation efficiency and recovery rate of various types of mammalian cells (e.g., mesenchymal stem cells, neutrophils, fibroblast, and natural killer cells) was determined. After removal of the mammalian cells from the cell culture plates, the mammalian cells were enucleated by density gradient centrifugation using discontinuous Ficoll gradients, high-speed centrifugation (FIGS. 2A-D). Table 1 summarizes the results of enucleation using a suspension protocol. Enucleation efficiency and cell viability was the highest in both hTERT transformed and primary mesenchymal stem cells (MSCs), as well as in fibroblasts and neutrophils. Table 2 summarizes the results of enucleation using an adherent protocol. Enucleation efficiency was greater than 70% in both mesenchymal stem cells and macrophages. This experiment showed that various types of mammalian cells could undergo enucleation using any of the methods described herein.

TABLE 1

Enucleation efficiency and viability determinations of mammalian cells using the suspension protocol.

| Cell type | | Enucleation Efficiency | Recovery Rate | Viability after 24 hours | Yield per run |
|---|---|---|---|---|---|
| MSC cells | AD-MSC (hTERT) | 90%-95% | 60%-90% | 80%-95% | 12-15M |
| | UC-MSC (primary) | 85%-90% | 60%-80% | 80%-95% | 10-15M |
| | BM-MSC (primary) | 80%-90% | 40%-50% | 80%-90% | ~8M |
| NK cells | NKL | 50%-85% | 20%-50% | 50%-75% | ~8M |
| | NK-92 | 70%-90% | 20%-40% | 20%-40% | ~5M |
| Macrophages | RAW 264.7 | 85%-95% | 40%-70% | 20%-40% | ~15M |
| Neutrophils | HL-60 | 60%-98% | 20%-40% | 60%-80% | ~15M |
| Fibroblasts | L929 | 70%-90% | 50%-70% | 70%-90% | ~15M |
| | NIH3T3 | 70%-80% | 40%-50% | 70%-80% | ~9M |

Enucleation efficiency = enucleated cells versus total recovered cells;
Recovery rate = recovered cells versus total input cells used for enucleation.
Viability after 24 hours = live cells measured by Trypan blue staining versus total cells;
Yield per run = the number of cytoplasts harvested for each run; M = million cells
AD-MSC (hTERT) = human hTERT immortalized adipose-derived mesenchymal stem cells;
BM-MSC (primary) = human primary bone marrow-derived mesenchymal stem cells;
NK = natural killer cells.

TABLE 2

Enucleation efficiencies and viability determinations of mammalian cells using the adherent protocol

| Cell type | | Enucleation Efficiency | Recovery Rate | Viability after 24 hours | Yield per run |
|---|---|---|---|---|---|
| MSC cells | AD-MSC (hTERT) | 70%-95% | 40%-60% | 80%-95% | 1M |
| Macrophages | RAW 264.7 | 85%-95% | 40%-70% | 10%-30% | ~1M |

Figure 3A:
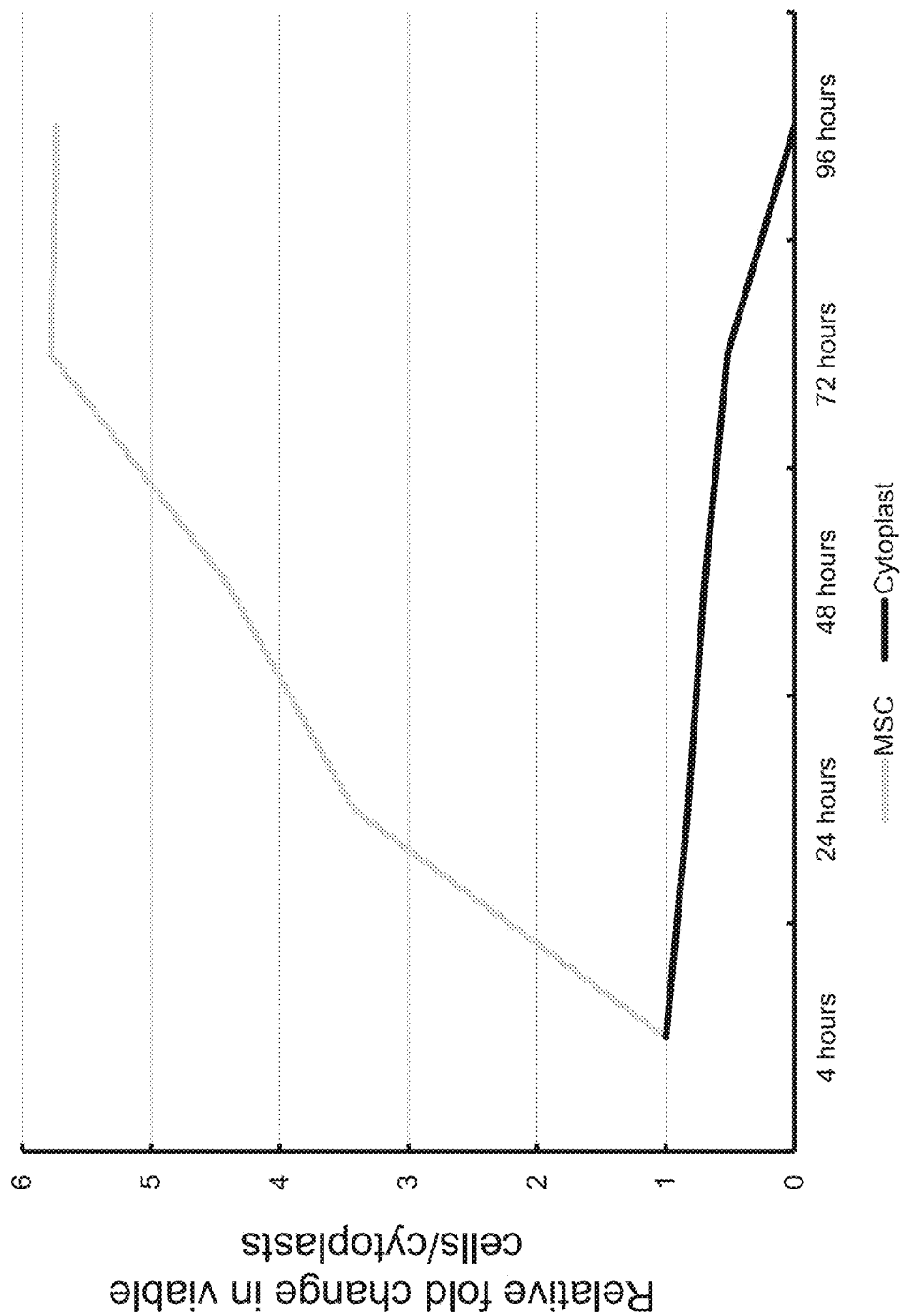
FIG. 3A is a representative graph showing the relative fold change in viable cells or cytoplasts over time.
Figure 3B:
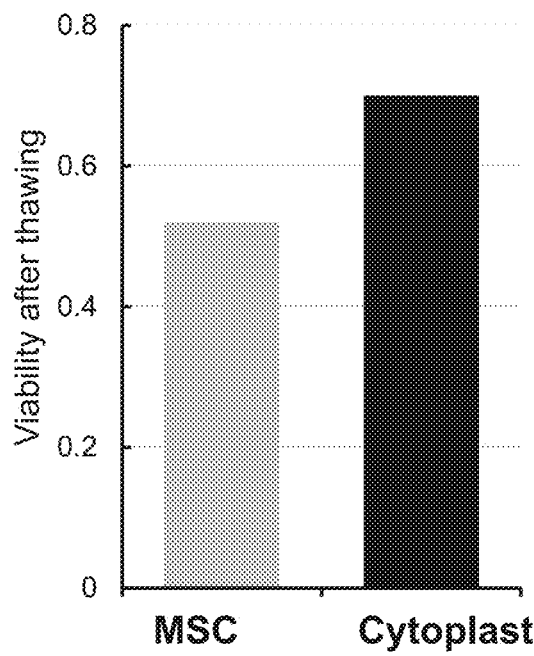
FIG. 3B is a representative graph showing the viable cells and cytoplasts after recovery from frozen storage (cryopreservation).
Figure 3C:
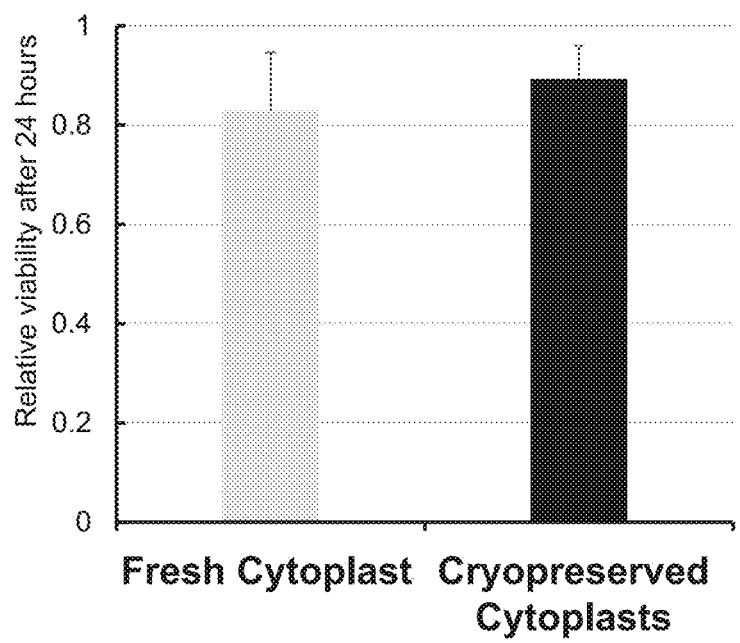
FIG. 3C is a representative graph showing the relative viability of cytoplasts 24 hours after enucleation (fresh cytoplasts) or 24 hours after recovery from frozen storage (cryopreserved) following enucleation, where fresh and cryopreserved cytoplasts are compared to the viability of cytoplasts 4 hours after enucleation. Mean±SEM; n=10.

Enucleation efficiency = enucleated cells versus total recovered cells;
Recovery rate = recovered cells versus total input cells used for enucleation.
Viability after 24 hours = live cells measured by Trypan blue staining versus total cells;
Yield per run = the number of cytoplasts harvested for each run; M = million cells Next, the survival of cytoplasts was determined across 96 hours (FIG. 3A). Whereas MSC proliferated over-time, cytoplasts did not. Instead, the relative fold change in viable cytoplasts remained fairly constant for 72 hours before declining at 96 hours. Thus, cytoplast survival spanned 3-4 days. As most cell-based therapies are not used immediately, the viability of cytoplasts after cryopreservation was determined. Surprisingly, the viability of cytoplast after cryopreservation was greater than the viability of MSC following cryopreservation (FIG. 3B). Cytoplasts plated immediately after enucleation and cytoplasts recovered from cryopreservation displayed similar relative cell viability after 24 hours (FIG. 3C). This experiment showed that cytoplasts survival was not affected by cryopreservation.

Next, a large-scale production of cells was set up ex vivo, followed by large-capacity density gradient centrifugation and enucleation, which lead to the generation of a therapeutic cytoplast. In one embodiment, the therapeutic cytoplast is loaded with therapeutic cargo (e.g., mRNA, drugs, peptides, etc. . . . ) for disease treatment. In another embodiment, the therapeutic cytoplast is prepared for immediate use (e.g., for intravenous injection (IV), intraperitoneal injection (IP), tissue, or in vitro applications) for diagnostic use.

Figure 4:
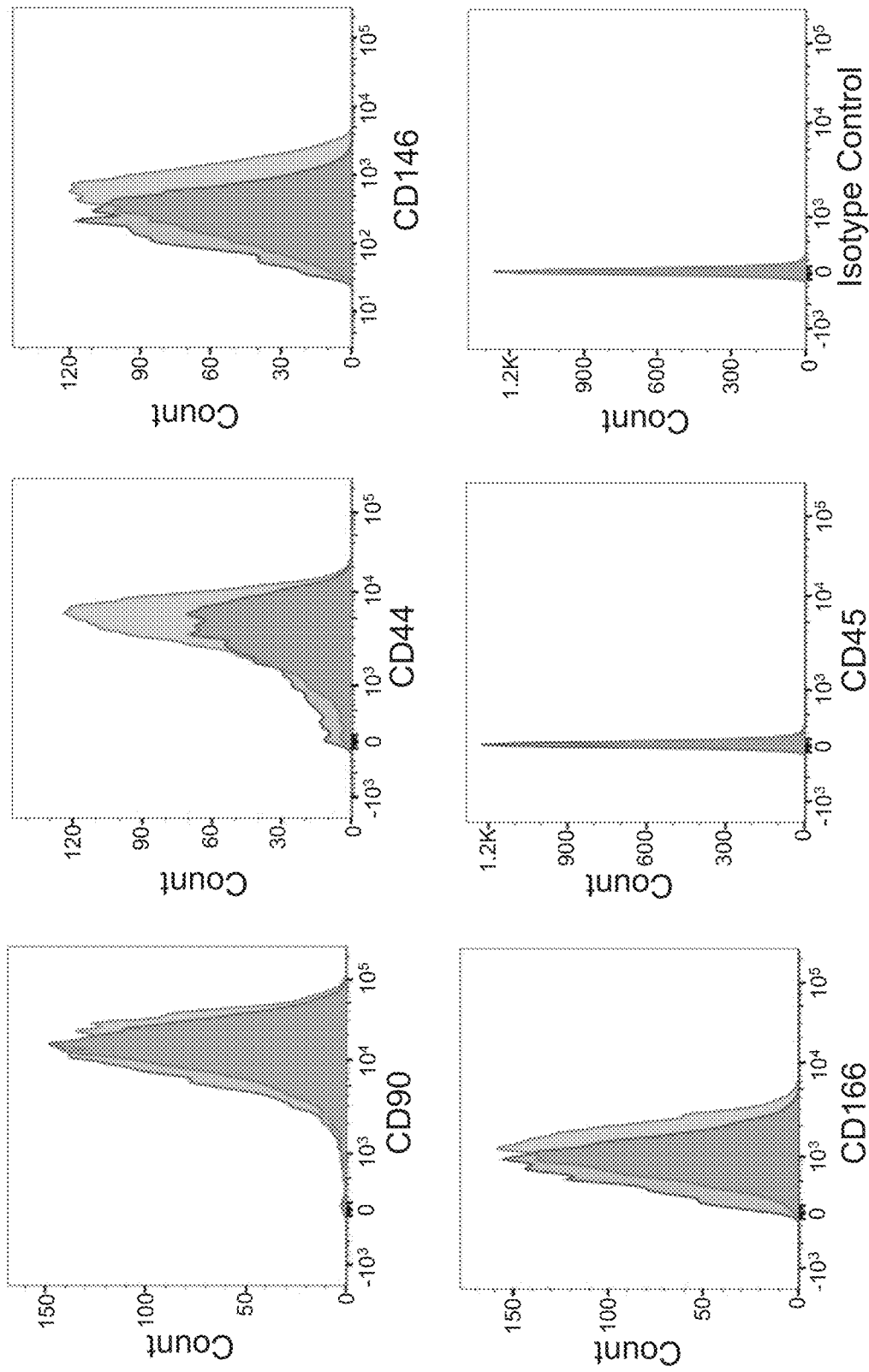
FIG. 4 are representative flow cytometry graphs showing the number of events counted over the signal strength of the indicated fluorescent antibody/marker (CD90, CD44, CD146, CD166, CD45, and isotype control). Bone marrow MSCs or MSC-derived cytoplasts were stained 24 hours after enucleation and then analyzed by flow cytometry with FlowJo software. Green (light gray) represents nucleated MSCs and red (dark gray) represents enucleated cytoplasts.
Figure 5A:
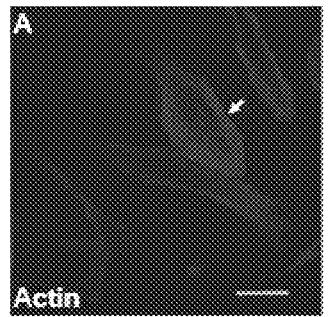
FIGS. 5A-F'.
Figure 5C:
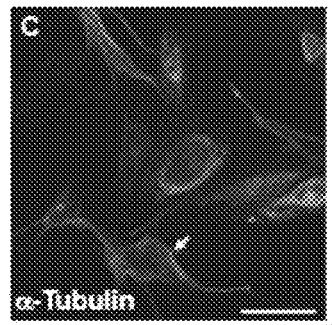
Figure 5B:
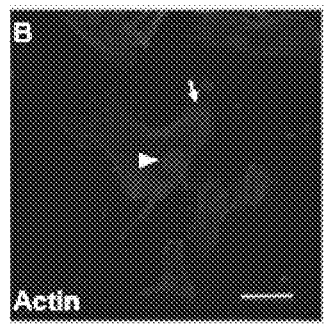
Figure 5D:
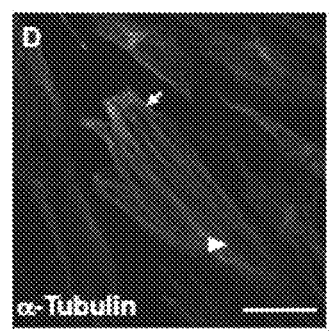
Figure 5E:
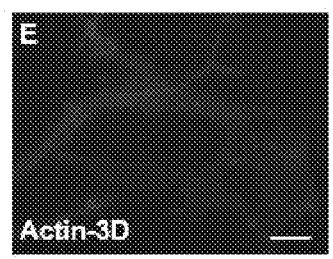
Figure 5E:
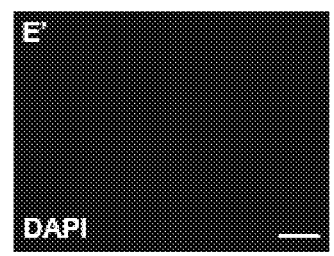
Figure 5F:
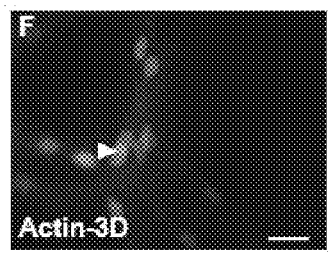
Figure 5F:
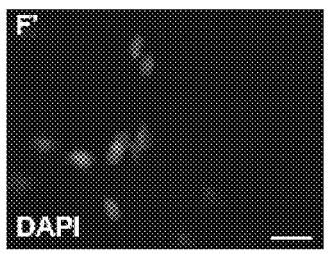
Figure 6A:
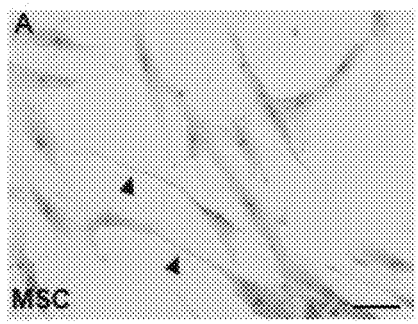
FIGS. 6A-D'.
Figure 6B:
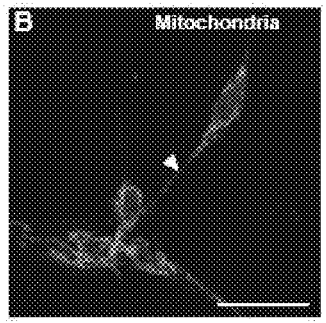
Figure 6C:
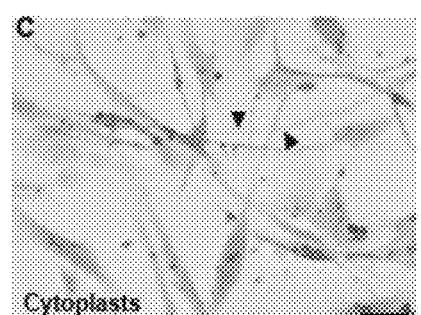
Figure 6D:
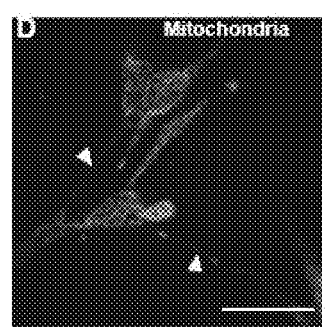
Figure 6C:
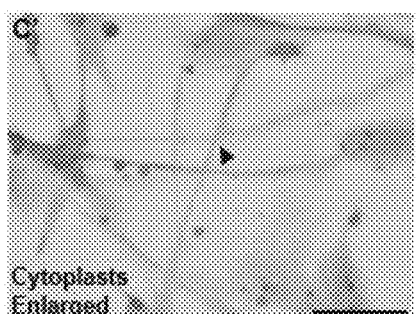
Figure 6D:
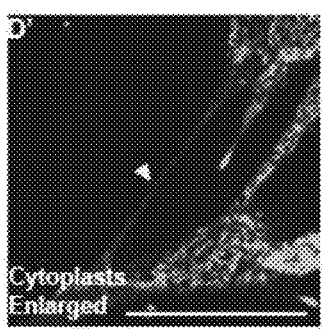
Figure 7A:
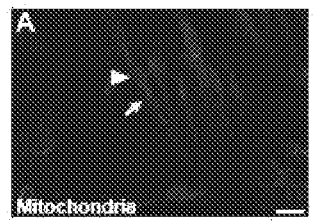
FIG. 7A-E'.
Figure 7A:
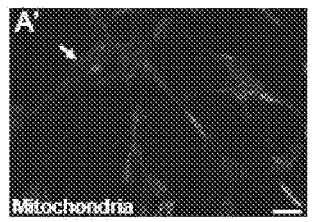
Figure 7B:
Figure 7B:
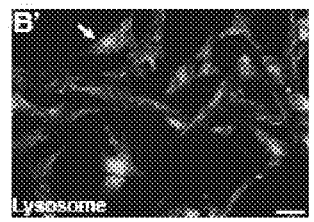
Figure 7C:
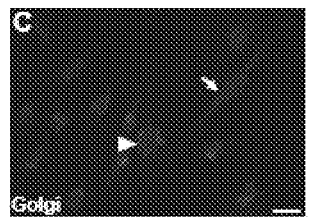
Figure 7C:
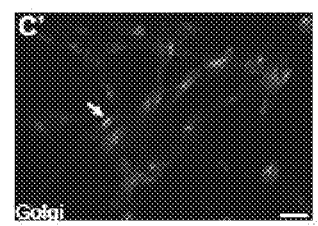
Figure 7D:
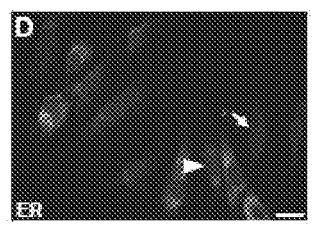
Figure 7D:
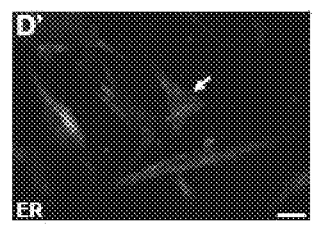
Figure 7E:
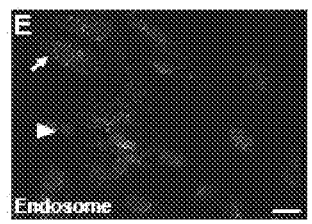
Figure 7E:
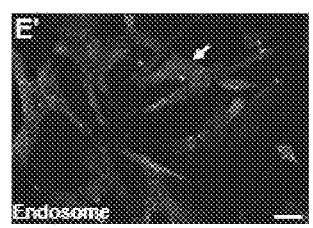
Figure 8A:
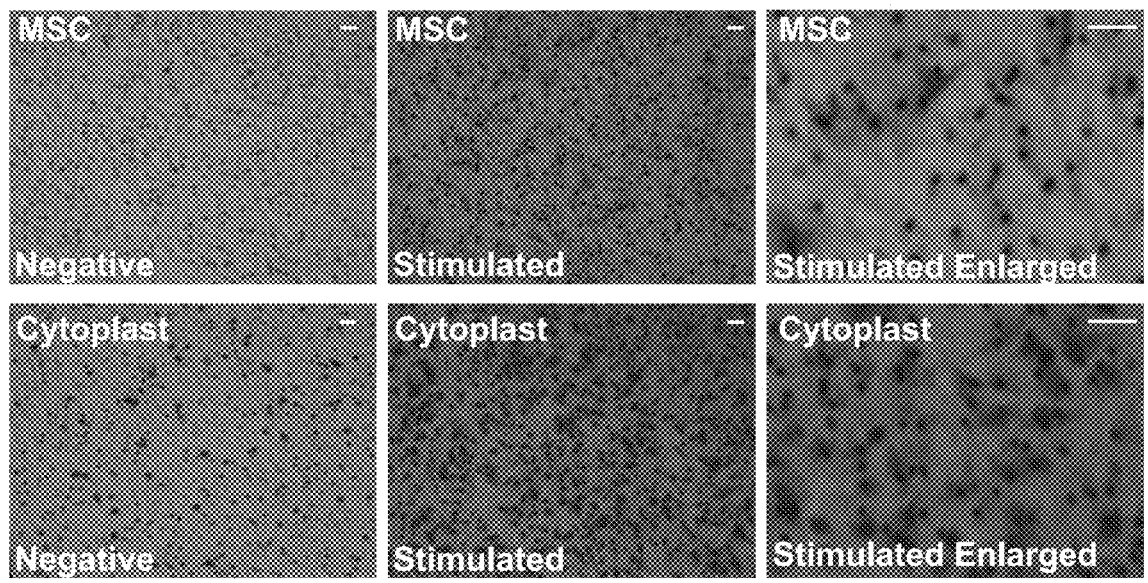
FIG. 8A is a representative bright field microscopy images of MSCs or cytoplasts in Boyden chamber assays that successfully migrated to the undersurface of 8.0 µm porous filters in 3 hours and were then stained with Crystal Violet. In the negative control, cells and cytoplasts migrated in culture media containing 2% FBS in both the upper and lower chambers. In the stimulated group, the bottom surface of the upper chamber was coated with fibronectin, and 100 ng/mL of stromal cell-derived factor 1 alpha (SDF-1a) was added to the lower chamber. Scale bar=50 µm.
Figure 8B:
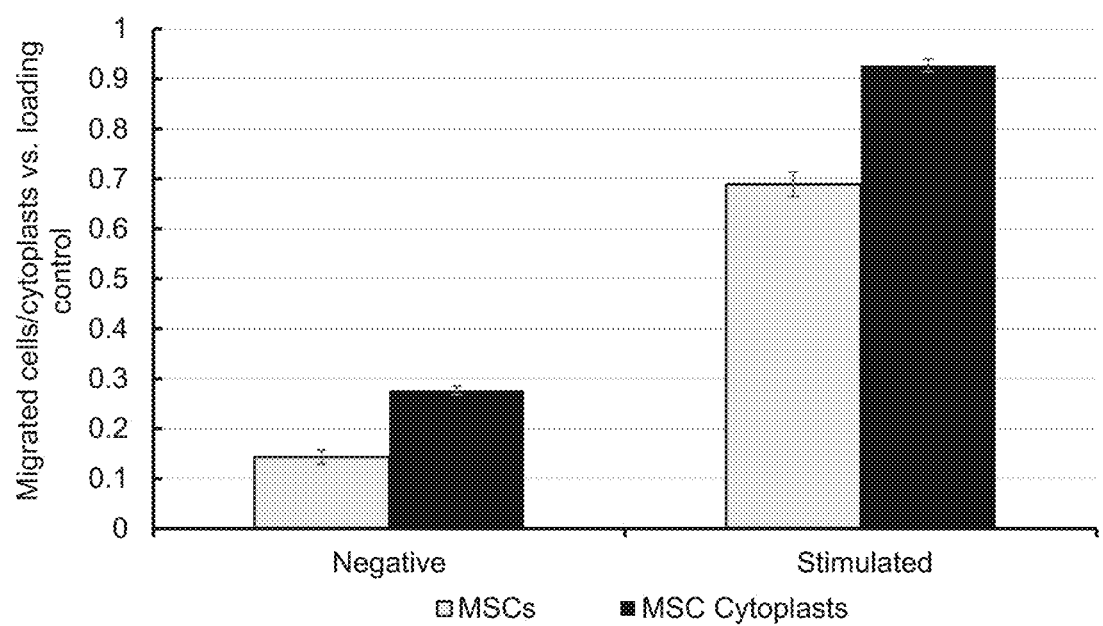
FIG. 8B is a representative bar graph showing the ratio of migrating MSCs or cytoplasts treated as in FIG. 8A (negative or stimulated), where each quantity was normalized to the loading control (MSCs or cytoplasts directly attached to fibronectin-coated plates). Mean±SEM; n=10.

Example 2—Cytoplasts Retain Intact Organelles, the Ability to Interact with the Extracellular Matrix, Perform Cell-Biological Functions, and can Serve as Delivery Vehicles with Therapeutic Value After determining whether cytoplasts could retain viability after cryopreservation, flow cytometry analysis were performed in order to determine whether the cell surface marker profile of MSC-derived cytoplasts differed from bone-marrow derived MSC (FIG. 4). As depicted in FIG. 4, both MSC-derived cytoplasts and bone-marrow derived MSCs maintained cell surface expression of CD45, CD90, CD44, CD146, and CD166. FIGS. 5A-F' and FIG. 6A-D' showed that cytoplasts attached, reorganized the cytoskeleton, spread on matrix proteins in 2D and 3D culture systems, and formed tunneling nanotubes, which can transfer bioproducts between cells of the same or different origin. Organelle-staining indicated that Golgi, ER, F-actin cytoskeleton, lysosomes, endosomes, microtubules, and mitochondria remain intact in cytoplasts (FIGS. 7A-E'). Furthermore, cytoplasts exhibited homing potential in vitro. Cytoplasts readily migrated on extracellular matrix proteins and migrated directionally towards soluble chemokine gradients (i.e. via chemosensing) (FIGS. 8A and 8B). Notably, cytoplasts transfected exogenously with purified mRNAs produced functional intracellular proteins, which could mimic therapeutic mRNA applications being developed for a variety of clinical uses and disease-states. This also demonstrates that the machineries for mRNA translation and protein synthesis operate normally in cytoplasts in the absence of a nucleus, and thus can be used to produce bioactive molecules with therapeutic value.

Figure 9E:
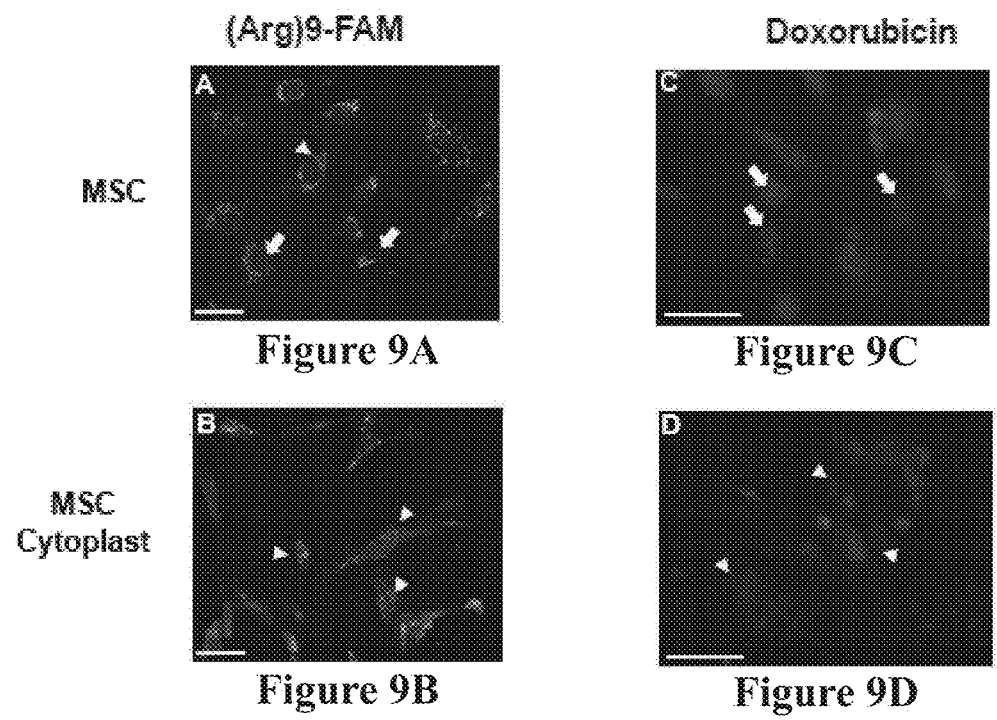
FIG. 9E is a representative bar graph showing the cell and cytoplast average corrected total cell fluorescence per area, which models the relative fluorescence while accounting for the size difference between cells and cytoplasts. Corrected Total Cell Fluorescence=Integrated Density–(Area of selected cell*Mean fluorescence of background readings). Mean±SEM; n=10.
Figure 9E:
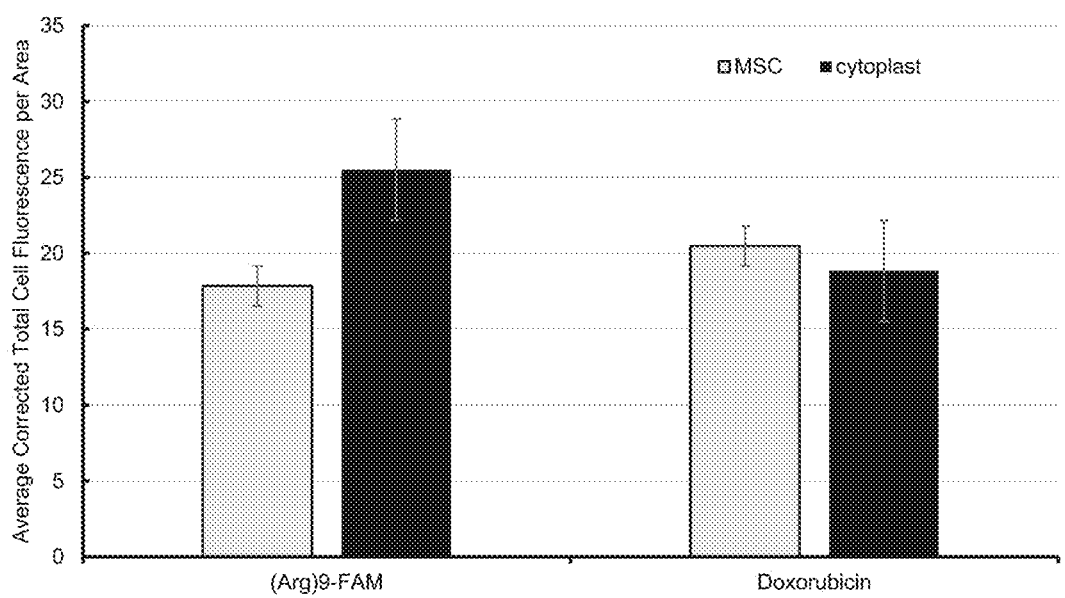
Figure 10A:
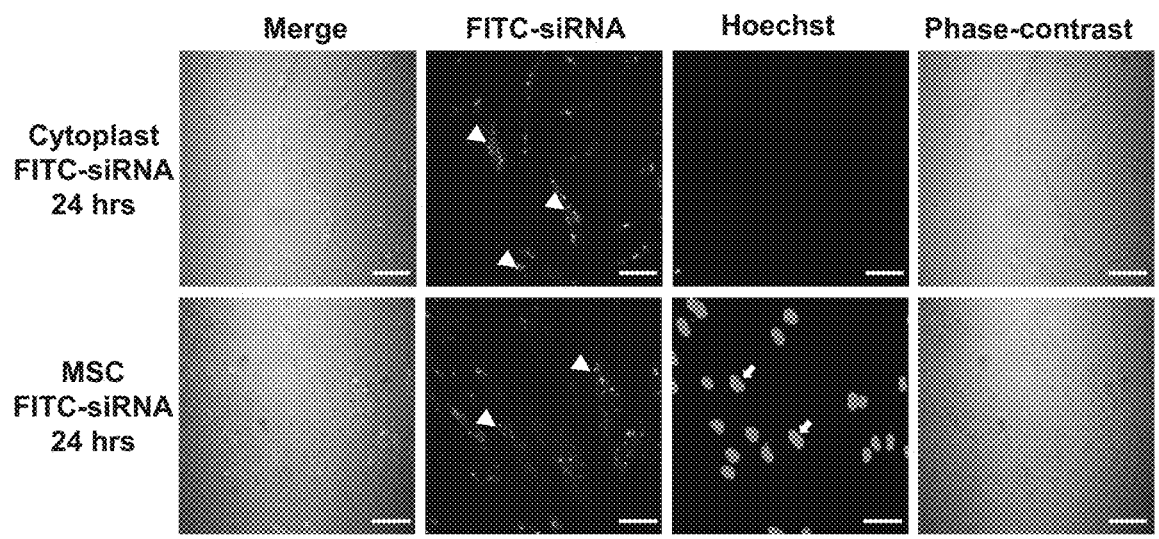
FIG. 10A is a panel of merged and unmerged confocal microscopy and phase contrast images of MSCs and MSC-derived cytoplasts incubated with fluorescein isothiocyanate (FITC, bright gray dots) labeled small interfering RNA (siRNA) for 24 hours and stained with Hoechst 33342 (nuclei, solid gray ovals). Arrowheads indicate positive FITC-labeled siRNA fluorescence. Arrows indicate nuclei. Scale bar=50 μm.
Figure 10B:
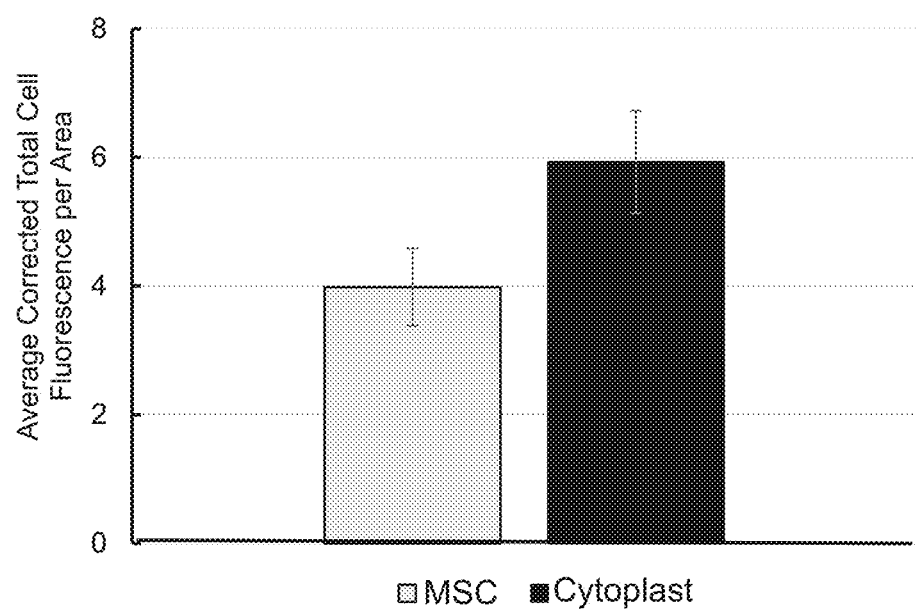
FIG. 10B is a representative bar graph showing the cell and cytoplast average corrected total cell fluorescence per area, which models the relative fluorescence while accounting for the size difference between cells and cytoplasts. Corrected Total Cell Fluorescence=Integrated Density–(Area of selected cell*Mean fluorescence of background readings).
Figure 11A:
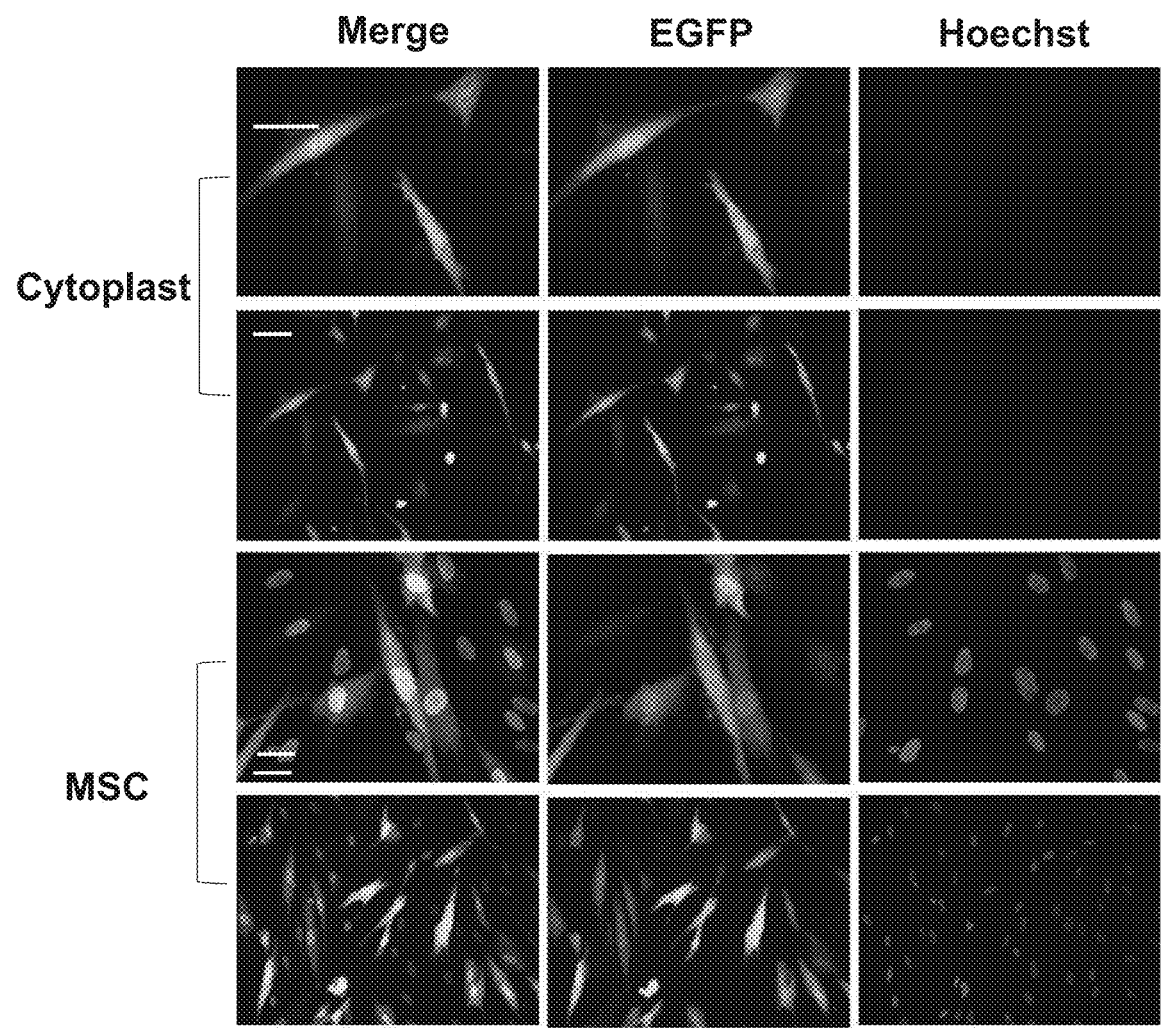
FIG. 11A are representative merged and unmerged epifluorescence microscopy images of MSC and MSC-derived cytoplasts 20 hours after transfection with purified enhanced green fluorescent protein messenger RNA (EGFP-mRNA) and stained with Hoechst 33342.
Figure 11B:
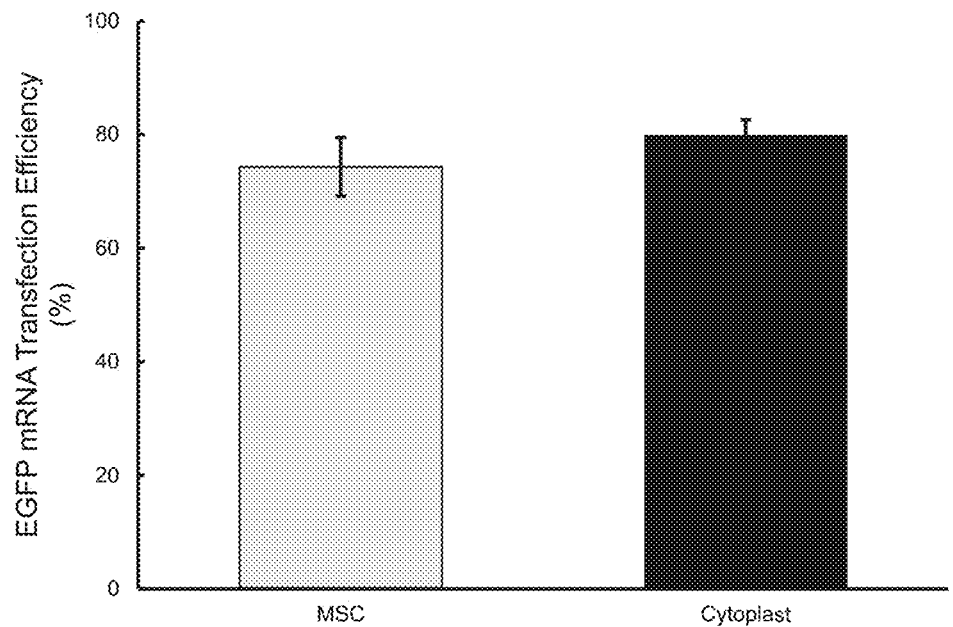
FIG. 11B is a representative bar graph showing the EGFP mRNA transfection efficiency (percentage of transfected cells out of total cells) of MSCs or MSC-derived cytoplasts treated as in FIG. 11A. Mean±SEM; n=3.
Figure 11C:
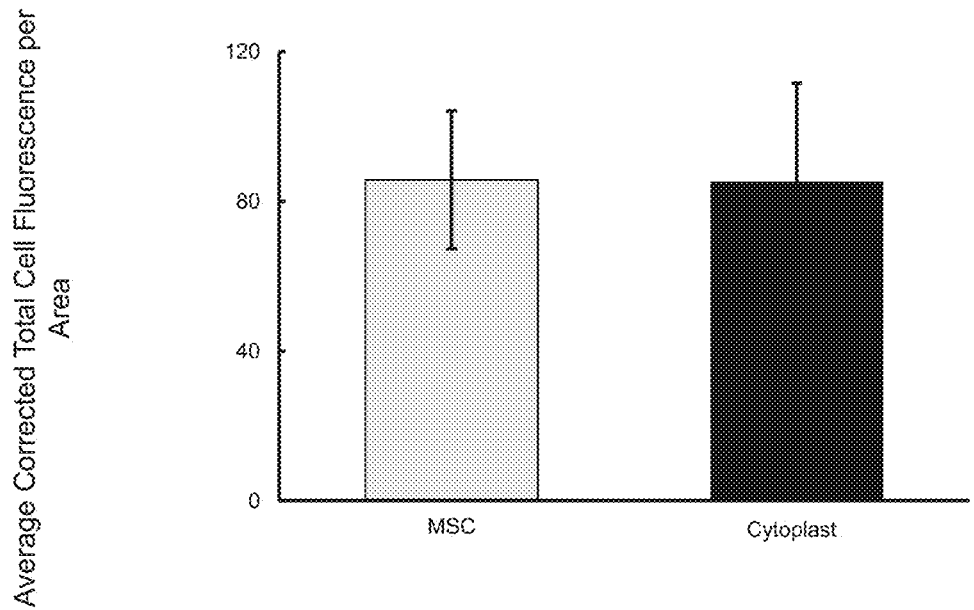
FIG. 11C is a representative bar graph showing the relative EGFP fluorescence intensity between cells and cytoplasts, accounting for difference in size. Mean±SEM; MSC group, n=27; MSC-derived cytoplast group, n=23. Corrected Total Cell Fluorescence=Integrated Density— (Area of selected cell*Mean fluorescence of background readings). All data are representative of at least two independent experiments.
Figure 12A:
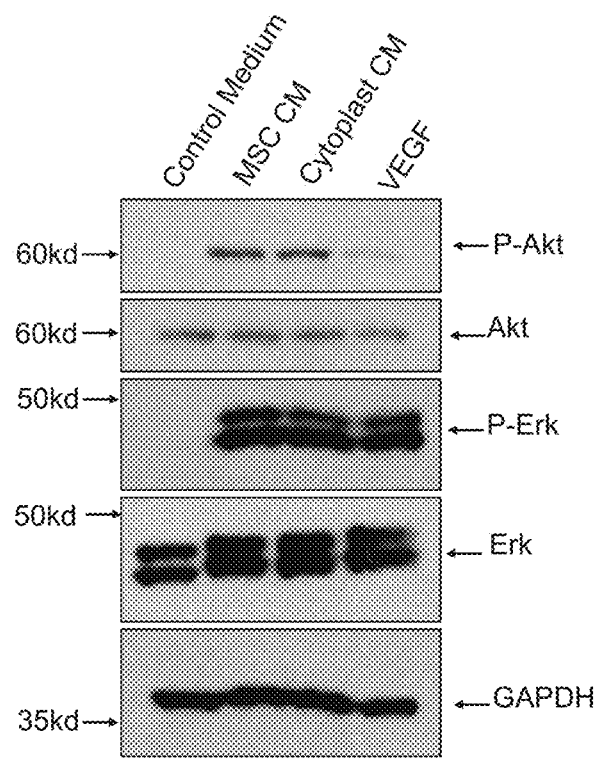
FIG. 12A is a representative Western blot of cells treated for 10 minutes with either control medium, MSC-conditioned medium (MSC CM), MSC-derived cytoplast-conditioned medium (Cytoplast CM), or 50 ng/mL of vascular endothelial growth factor (VEGF). Immunoblotting was performed for protein kinase B (Akt), phosphorylated Akt (p-Akt), extracellular signal-regulated kinase (Erk), phosphorylated Erk (p-Erk). Glyceraldehyde-3-phosphate dehydrogenase (GAPDH) was a loading control.
Figure 12B:
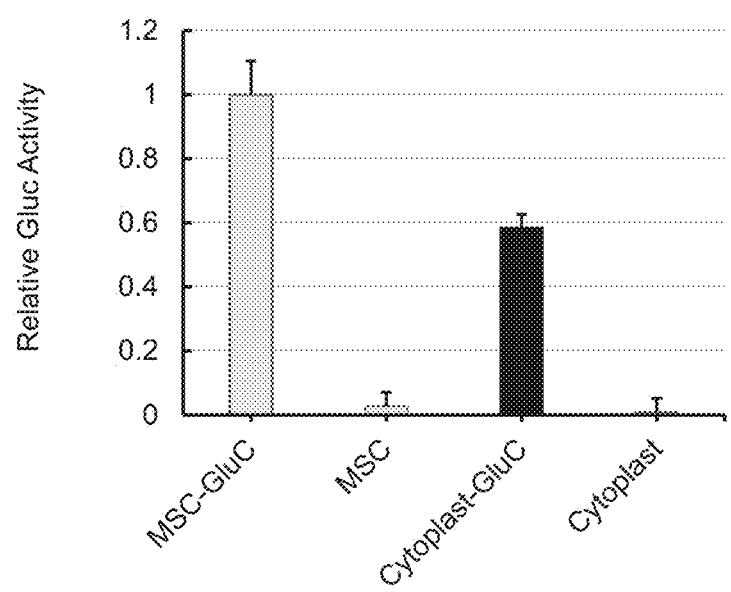
FIG. 12B is a representative bar graph showing the relative Gaussia luciferase (Gluc) activity in media 48 hours after plating MSCs transfected with Gluc mRNA (MSC-Gluc), non-transfected MSC control cell (MSC), MSC-derived cytoplasts transfected with Gluc mRNA (Cytoplast-Gluc), and non-transfected MSC-derived cytoplasts (Cytoplast).
Figure 12C:
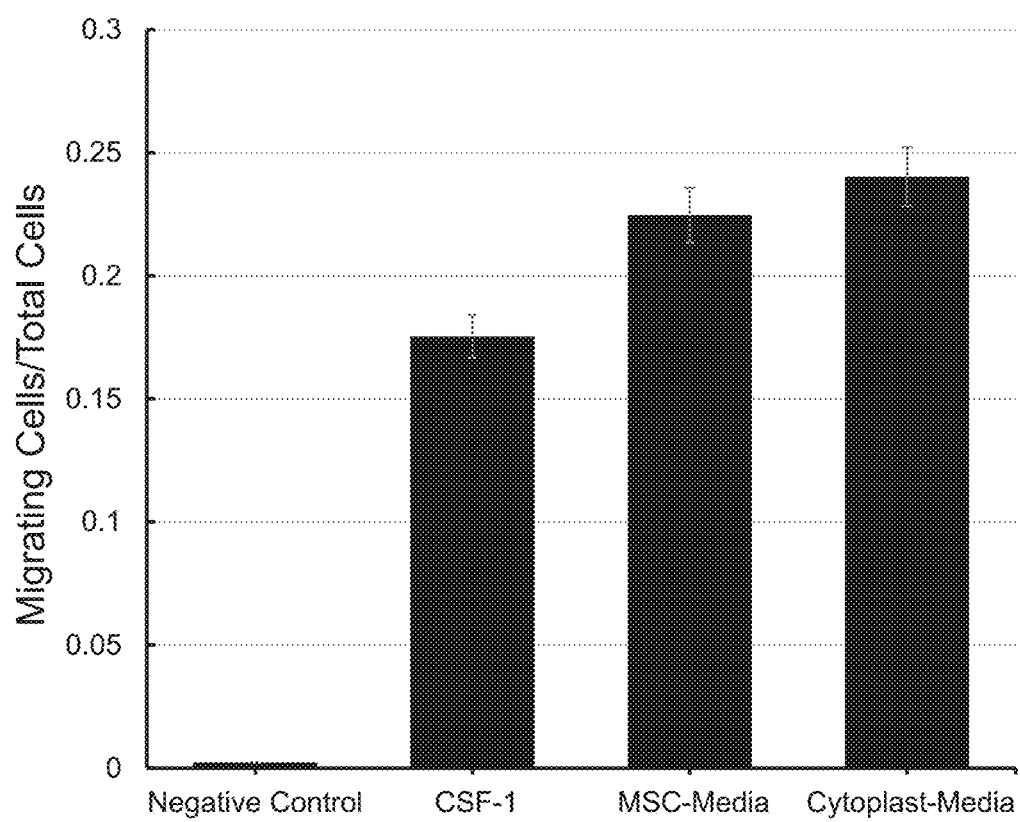
FIG. 12C is a representative bar graph showing the ratio of RAW 264.7 macrophages migrating towards a gradient of the indicated conditioned media for 4 hours in a Boyden chamber assay. Migratory cells on the lower membrane surface were stained with Crystal Violet and the number of cells counted per field and normalized to the loading control (cells directly attached to fibronectin-coated plates). Colony stimulating factor 1 (CSF-1), 40 ng/mL of mouse CSF-1 as a positive control; MSC-media, conditioned media from MSCs; Cytoplast media, conditioned media from MSC-derived cytoplasts. Mean±SEM; n=10.

Cytoplasts transfected exogenously with purified mRNA encoding known secreted proteins produce functional extracellular proteins in conditioned culture media, indicating that the ER/Golgi and secretory pathways operate normally in cytoplasts in the absence of a nucleus (FIG. 11). In addition, treatment of macrophages and endothelial cells with cytoplast-conditioned media containing secreted proteins activated key signal transduction responses in these cells (FIG. 12). This provided a proof of concept that cytoplasts could be used as novel vehicles to produce and deliver secreted proteins and biomolecules with therapeutic value. Cytoplasts can be loaded with various cargo including, but not limited to, siRNA, shRNA, mRNA, DNA plasmids, peptides, and chemotherapeutic agents (see, e.g., FIGS. 9 and 10).

Example 3—Engineered Cytoplasts can Function Both In Vitro and In Vivo

Figure 13A:
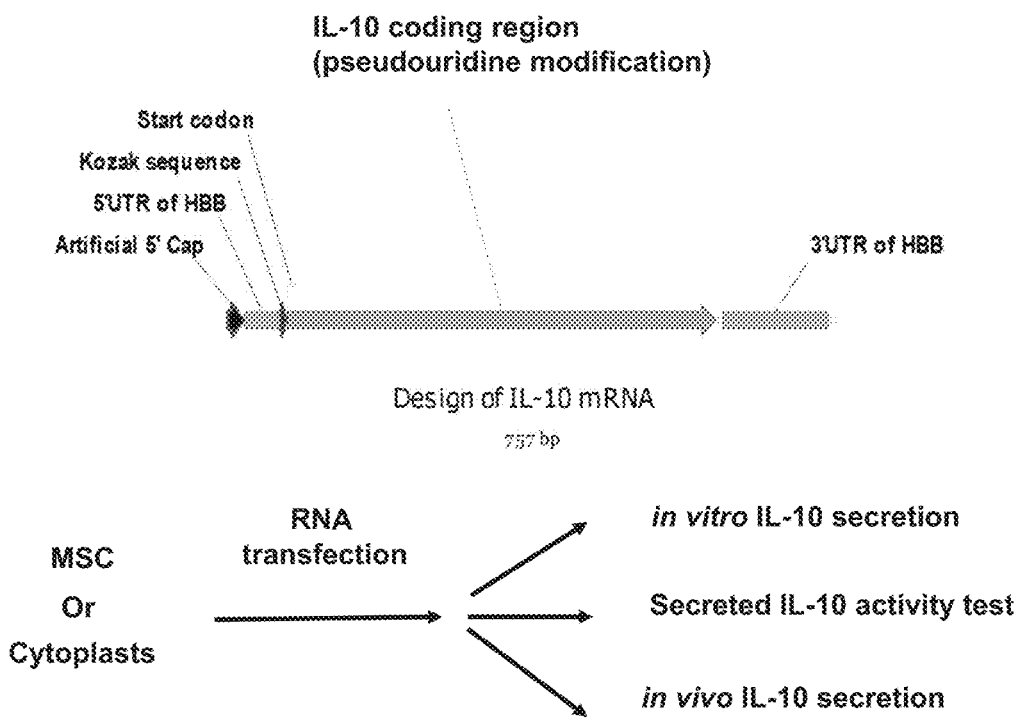
FIG. 13A is a schematic representation of an interleukin 10 (IL-10) mRNA transfected into MSC and cytoplasts. Kozak sequence was added in front of the start codon of the IL-10 mRNA coding region (CDS). 5'UTR and 3'UTR of human beta globin (HBB) mRNA were added respectively to the 5' and 3' end of IL-10 CDS. An artificial 5'Cap was added to the 5' end of the IL-10 mRNA and the pseudouridine modification was engineered to increase mRNA stability.
Figure 13B:
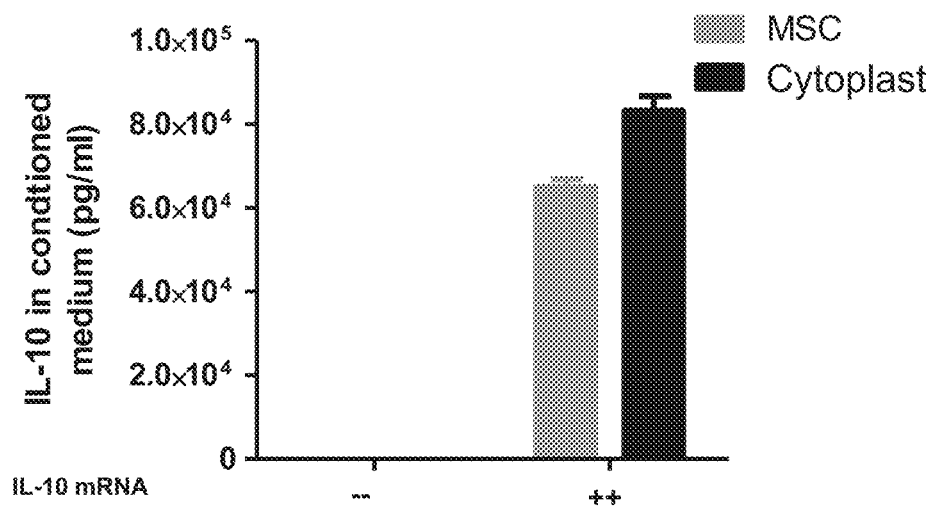
FIG. 13B is a bar graph showing IL-10 concentration in the culture medium of transfected (++) or non-transfected (--) MSC or MSC-derived cytoplasts. MSC-derived cytoplasts were transfected with IL-10 mRNA, then seeded in a 24 well plate at $2.5 \times 10^4$ cells/well. Conditioned medium (CM) was collected 24 hours after transfection and the IL-10 concentration determined by ELISA.
Figure 13C:
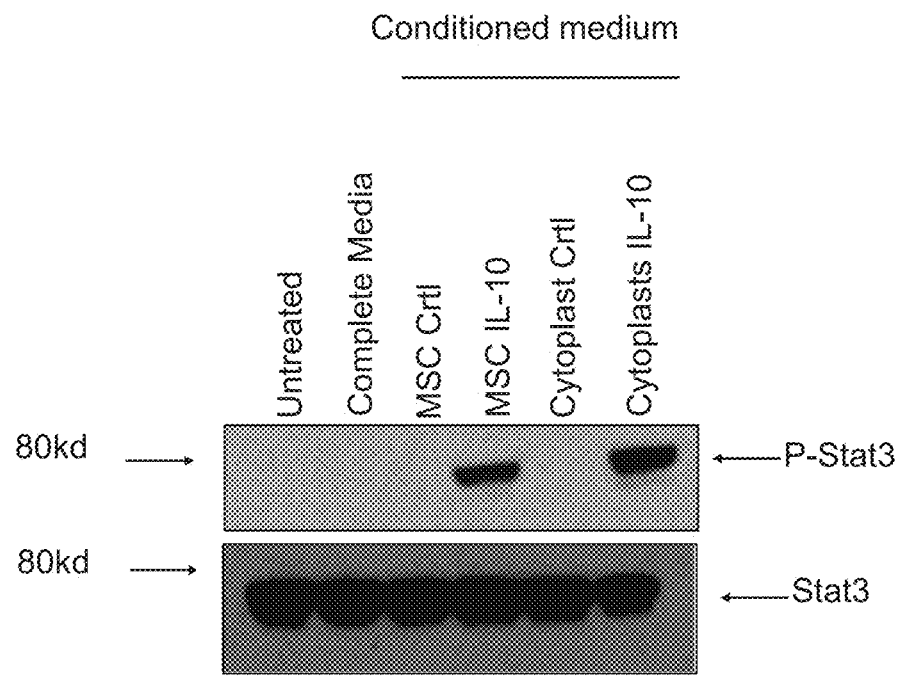
FIG. 13C is an immunoblot showing protein expression of Stat3 and phosphorylated Stat3 (P-Stat3, a marker of IL-10 activation) in serum-starved RAW macrophage cells treated with the indicated conditioned media (CM) from MSCs or cytoplasts treated as in FIG. 13B for 1 hour. Untreated=no CM treated control. Complete medium=RAW cells treated with MSC complete culture medium. MSC Ctrl=RAW cells treated with CM from non-transfected MSCs. MSC IL-10=RAW cells treated with CM from IL-10 mRNA transfected MSCs. Cytoplast Ctrl=RAW cells treated with CM from non-transfected cytoplasts. Cytoplasts IL-10=RAW cells treated with CM from IL-10 mRNA transfected cytoplasts.
Figure 13D:
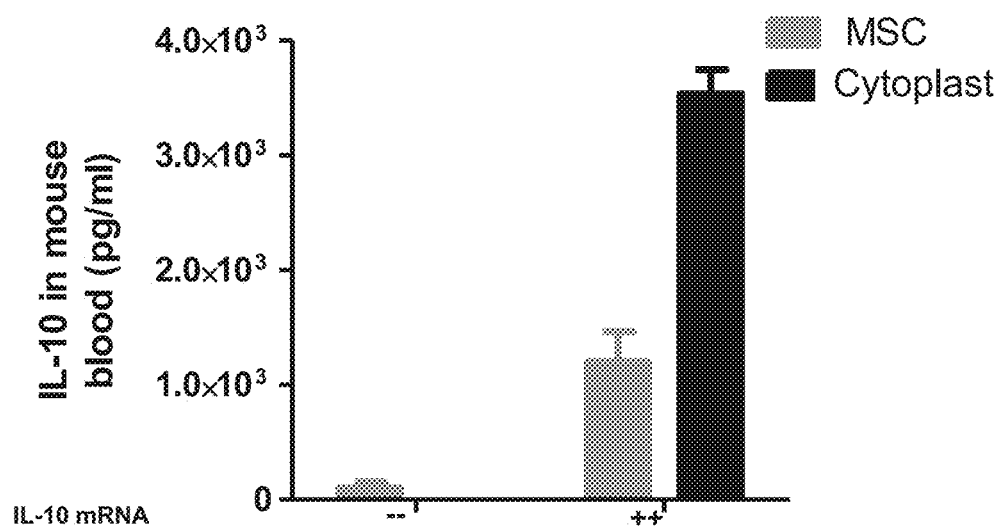
FIG. 13D is a bar graph showing the concentration of secreted IL-10 cytokine in the mouse blood as determined by ELISA. MSC or MSC-derived cytoplasts were treated as in FIG. 13B and retro-orbitally injected into the vasculature of C57BL/6 mice. Two hours after injection, animals were euthanized, and blood samples were collected by cardiac puncture. Mean±SEM; n=3.

Without wishing to be bound by theory, the examples show that cytoplasts that have been engineered to express a "cargo", e.g., an exogenous mRNA molecule, can be produced. FIGS. 13B and 13C show that MSC-derived cytoplasts can be engineered to produce and secrete therapeutic levels of a functional anti-inflammatory cytokine interleukin 10 (IL-10) in vitro and in a preclinical mouse model following intravenous injection. FIG. 13B shows that cytoplasts transfected with IL-10 mRNA can secrete high levels of IL-10. To determine whether the secreted IL-10 is active, serum-starved macrophages were incubated with conditioned medium (CM) from untreated MSCs, MSCs expressing IL-10, untreated cytoplasts, and cytoplasts expressing IL-10. Phosphorylated STAT3 was detected in macrophages following incubation with CM from MSCs expressing IL-10 and following incubation with CM from cytoplasts expressing IL-10, whereas no STAT3 activity was detected in macrophages following incubation with CM from untreated MSCs and untreated cytoplasts (FIG. 13C). To determine whether cytoplast-secreted IL-10 can be detected in vivo, C57Bl/6 mice were injected retro-orbitally with MSC or MSC-derived cytoplasts expressing IL-10. Two hours post-injection, blood was collected and the levels of IL-10 were determined. Little to no IL-10 was detected in the blood of mice that were injected with untreated MSC (FIG. 13D). As shown in FIG. 13D, higher levels of IL-10 were detected in mice injected with MSC-derived cytoplasts expressing IL-10 as compared to the level in mice injected with untreated MSC.

These data illustrate the potential of genetically engineered cytoplast-based cell therapies to produce and secrete clinically-relevant therapeutic cytokines to treat normal and diseased tissues.

Figure 14A:
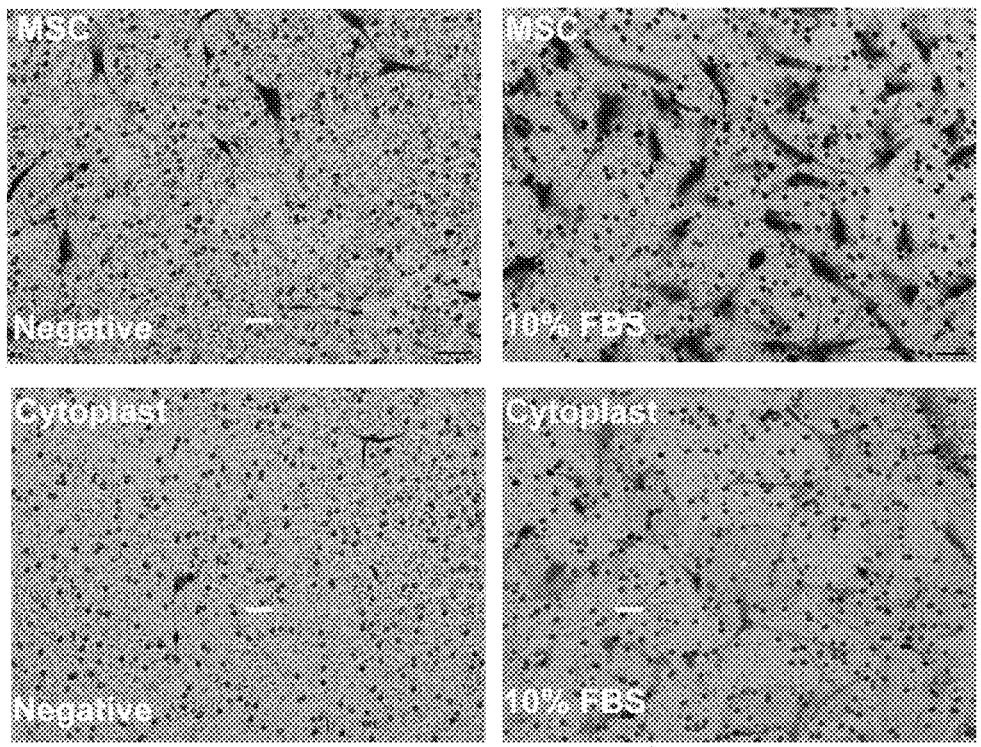
FIG. 14A are representative bright field microscopy images of Crystal Violet-stained MSCs or MSC-derived cytoplasts in a Boyden chamber assay that invaded to the undersurface of 8.0 μm porous filters coated with Basement Membrane Extract (BME) towards 10% FBS as a chemoattractant for 24 hours. Negative=no FBS (negative control). Scale Bar=50 μm.
Figure 14B:
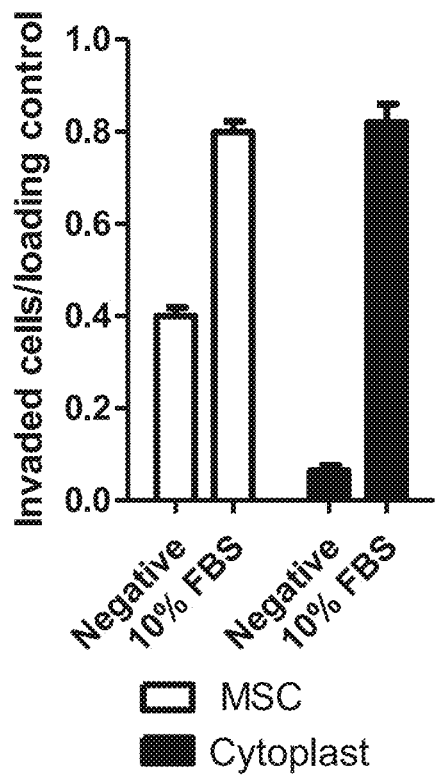
FIG. 14B is a representative bar graph showing the ratio of MSC or MSC-derived cytoplasts treated as in FIG. 14A that invaded to the undersurface of the membrane compared to the loading control. Mean±SEM; n=18.

To determine whether MSC-derived cytoplasts can invade through the basement membrane, MSC or MSC-derived cytoplasts were allowed to invade through the basement membrane towards 10% FBS for 24 hours. As shown in FIGS. 14A and 14B, MSC-derived cytoplasts were just was efficient at invading the basement membrane as untreated MSCs in the presence of 10% FBS. Noteworthy, while untreated MSCs were able to invade the basement membrane in the absence of a chemoattractant, MSC-treated cytoplasts were far less able to invade the basement membrane in the absence of a chemoattractant. These data illustrate that MSC-derived cytoplasts can digest and invade through the basement membrane. These data illustrate the innate potential of cytoplast-based cell therapies to penetrate and migrate through complex extracellular matrix barriers to deliver their cargo(s) within tissues.

Figure 15A:
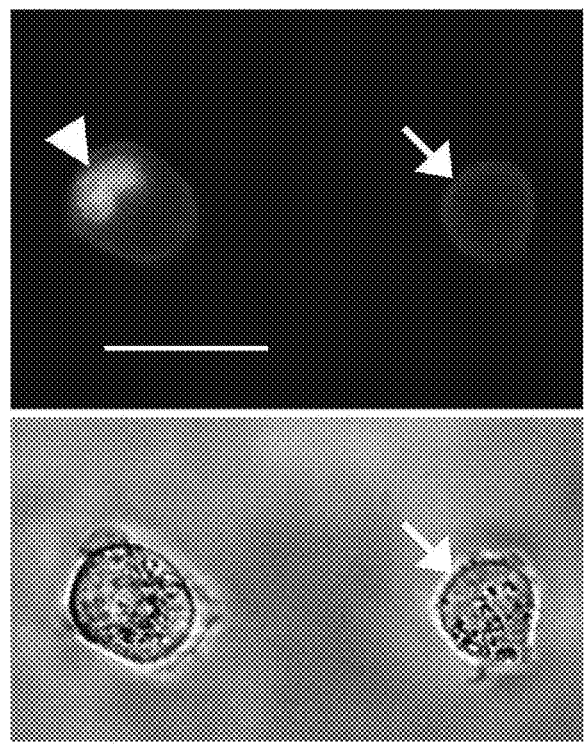
FIG. 15A is representative epifluorescence microscopy images (upper panel) and phase contrast microscopy images (lower panel) of MSCs and cytoplasts in suspension media. Actin cortex was stained with Lifeact RFP, while the cell nucleus was stained with Vybrant® Dyecycle™ Green. Arrows point to cytoplasts and arrowhead points to MSC nucleus. Scale bar=20 µm.
Figure 15B:
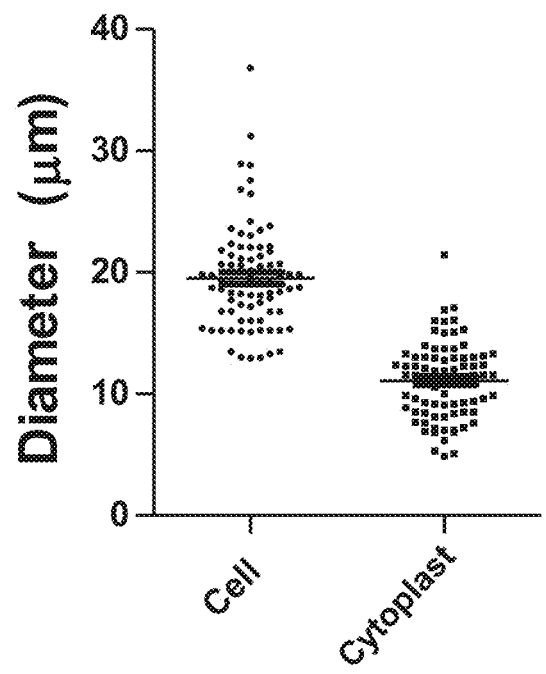
FIG. 15B is a representative scatter plot showing the size distribution of MSCs and cytoplasts as measured with Nikon Element software. Mean±SEM; n=80.
Figure 15D:
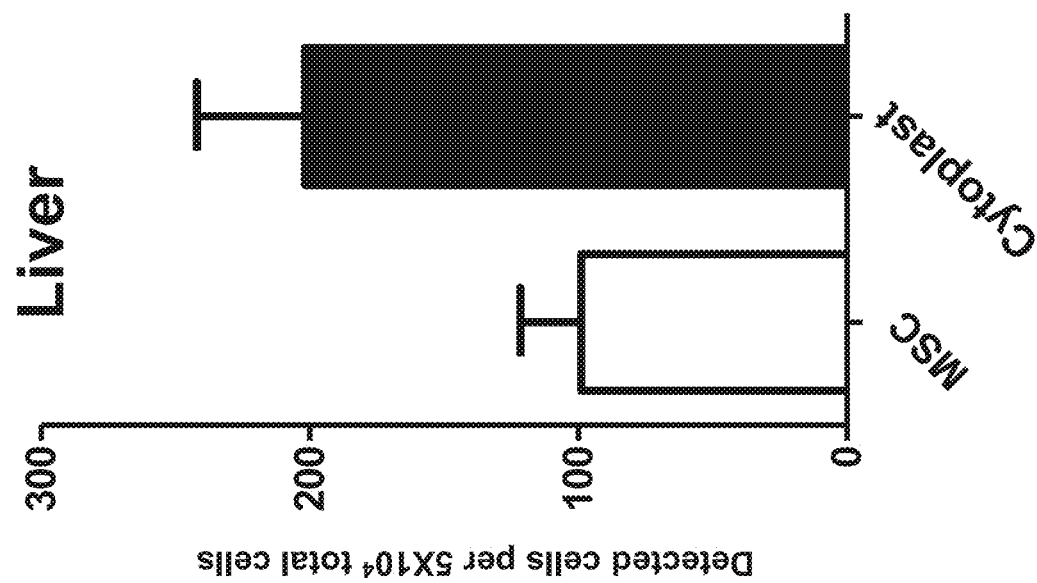
FIG. 15D is a representative bar graph showing the detected Vybrant® DiD labeled MSCs or cytoplasts present in liver. Mean±SEM; n=3. MSCs or cytoplasts were labeled with DiD dye and retro-orbitally injected into the vasculature of C57BL/6 mice. Tissues were harvested after 24 hours and cell suspensions analyzed by flow cytometry.
Figure 15C:
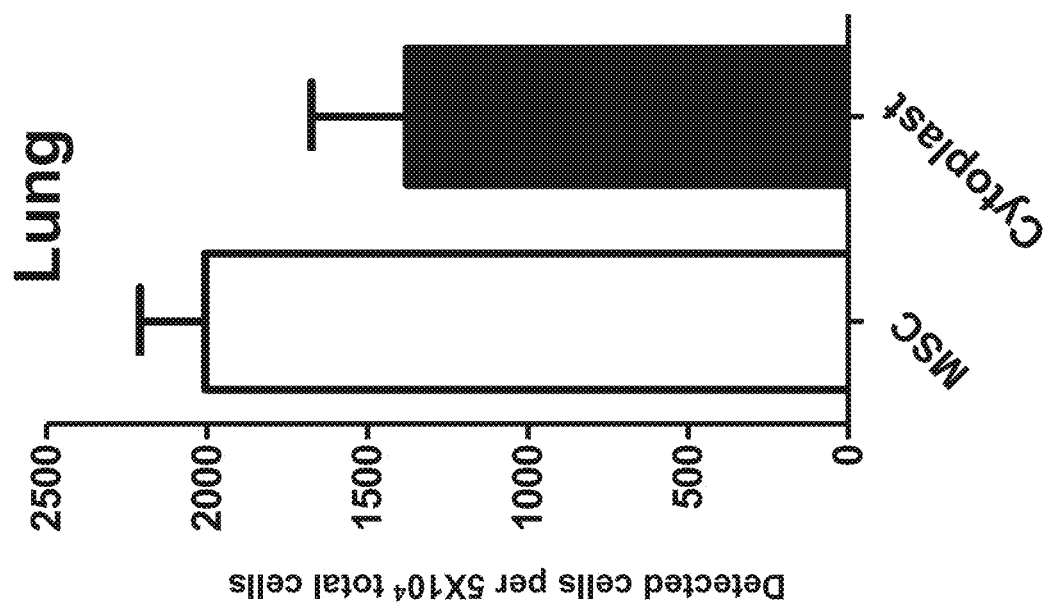
FIG. 15C is a representative bar graph showing the detected Vybrant® DiD-labeled MSCs or cytoplasts present in lung. MSCs or cytoplasts were labeled with DiD dye and retro-orbitally injected into the vasculature of C57BL/6 mice. Tissues were harvested after 24 hours and cell suspensions analyzed by flow cytometry. Mean±SEM; n=3.

As shown in FIGS. 15A and 15B, MSC-derived cytoplasts have an average diameter of 12 μm, while MSC have an average diameter of 20 μm. To determine the biodistribution of MSC-derived cytoplasts, mice were retro-orbitally injected with MSC or MSC-derived cytoplasts. As shown in FIGS. 15C and 15D, more MSC-derived cytoplasts were detected in the liver than the number of MSC detected in the liver. These data illustrate the potential of cytoplast-based cell therapies to be delivered directly to the circulation to treat a wide range of diseases.

Example 4—Engineered Cytoplasts can Express Functional Cell Surface Proteins

Figure 16A:
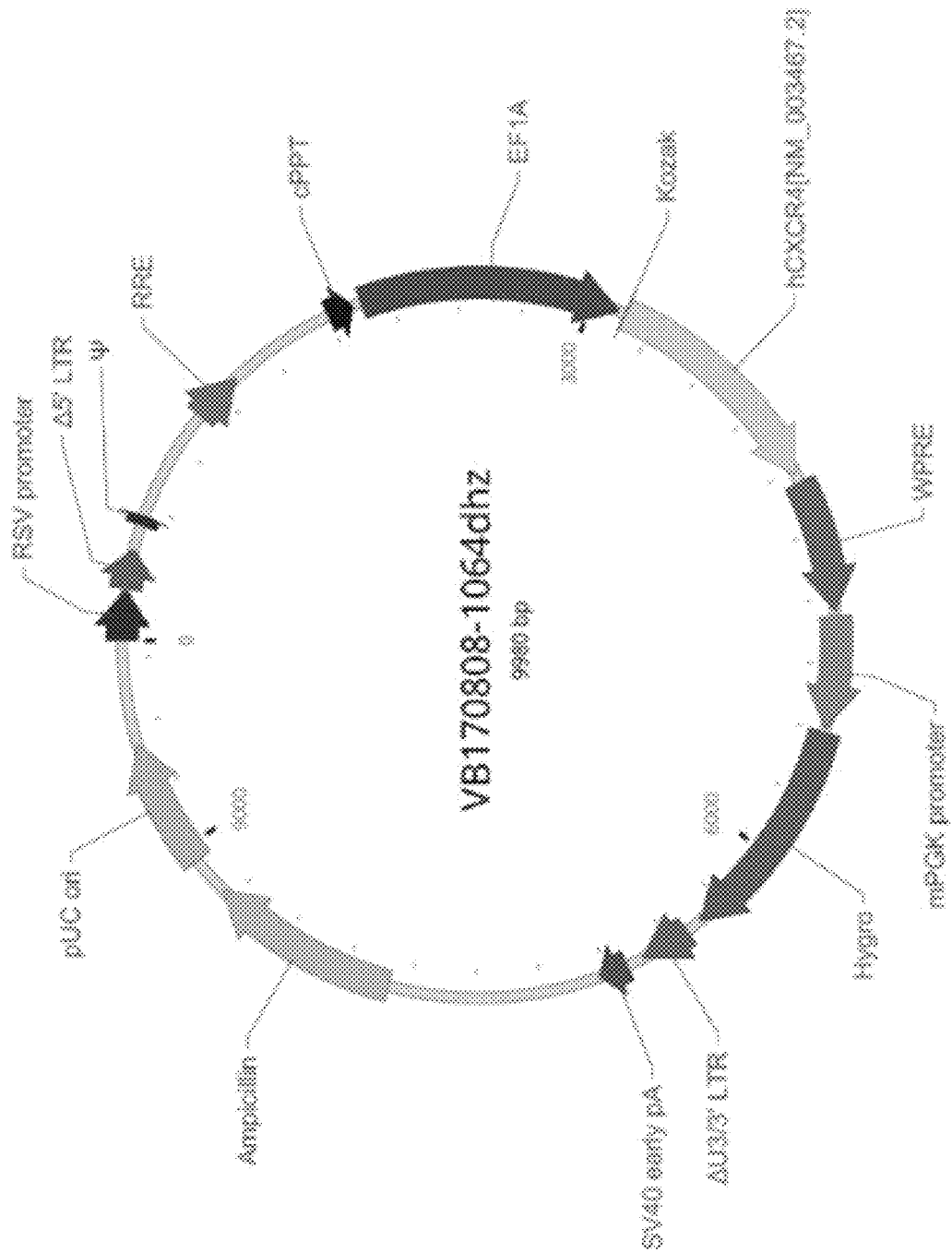
FIG. 16A is a schematic of a representative lentivirus vector engineered to express CXCR4 on MSCs and cytoplasts (SEQ ID NOs. 1-15).
Figure 16B:
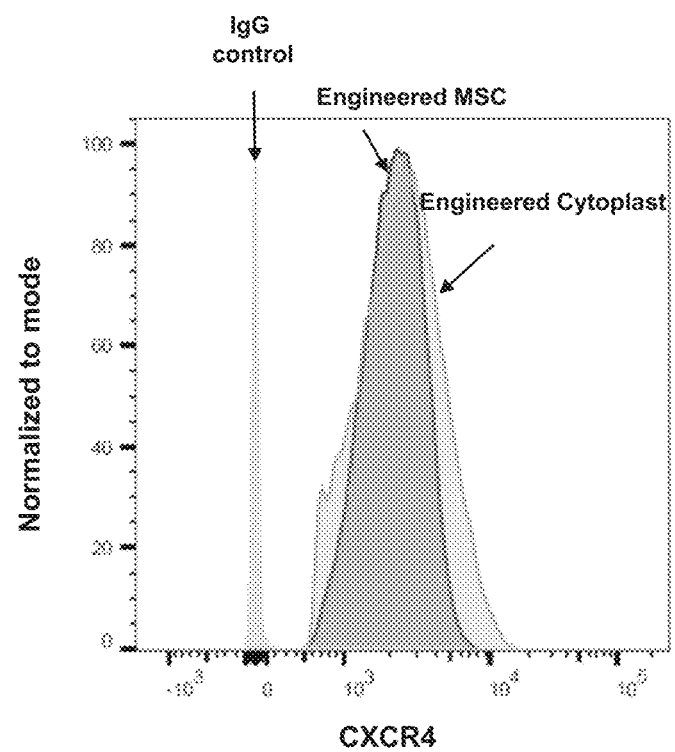
FIG. 16B is a representative flow cytometry graphs showing the number of events counted over the signal strength of the cell surface CXCR4 expression by fluorescent antibody on engineered cytoplasts and engineered parental MSCs as analyzed by FlowJo.
Figure 16C:
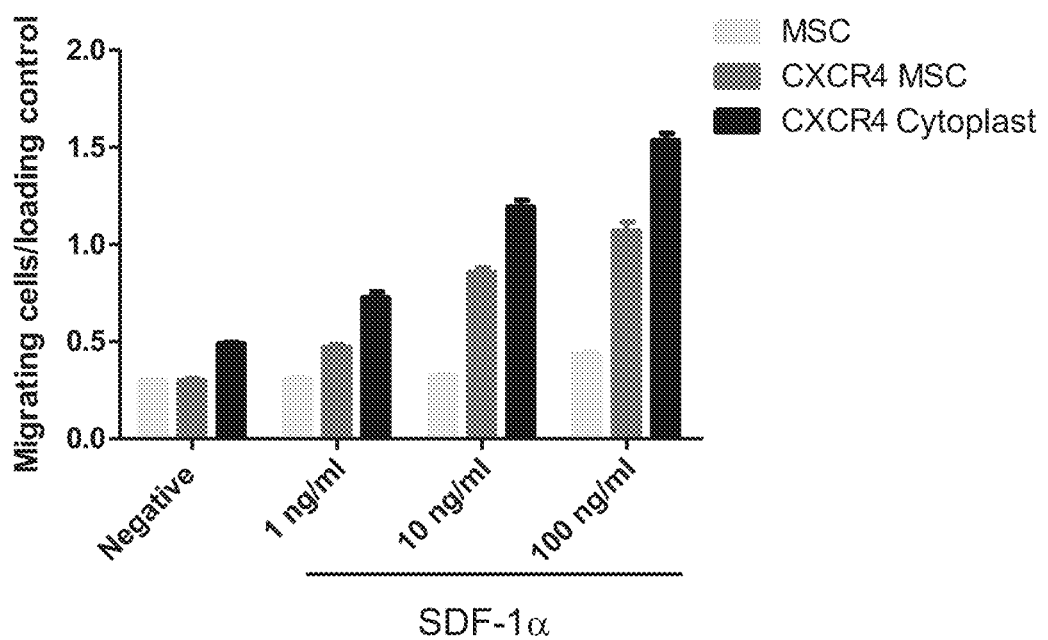
FIG. 16C is a representative bar graph showing the ratio of migrating cells or cytoplasts that migrated to the undersurface of the Boyden chamber membrane compared to the loading control. Mean±SEM; n=10. MSCs and MSC-derived cytoplasts with and without engineered CXCR4 receptors as in FIG. 16A were allowed to migrate towards the indicated concentrations of SDF-1α for 2 hours in a Boyden chamber assay.

As shown in FIG. 16B, engineered MSCs expressing CXCR4 and engineered MSC-derived cytoplasts expressing CXCR4 express comparable levels of CXCR4, as determined by flow cytometry. To determine whether engineered cytoplasts can express functional cell surface proteins, MSCs and MSC-derived cytoplasts expressing CXCR4 receptors were allowed to migrate towards various concentrations of SDF-1α. As shown in FIG. 16C, MSC-derived cytoplasts engineered to express functional CXCR4 can migrate towards SDF-1α, and cell migration increases with increasing concentrations of SDF-1α. Furthermore, the number of migrating MSC-derived cytoplasts was greater than the number of migrating MSCs expressing CXCR4 (FIG. 16C).

Figure 17A:
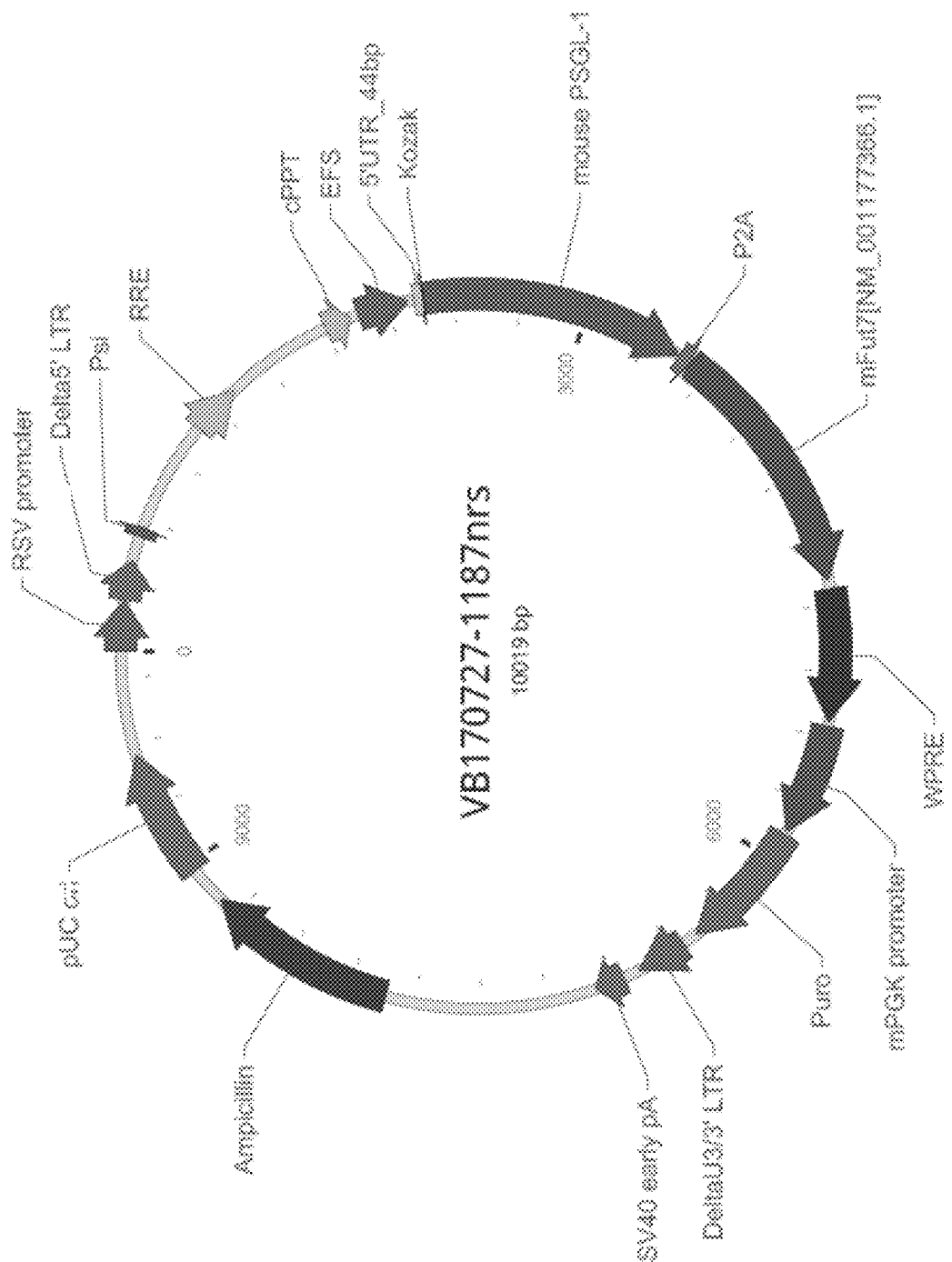
FIG. 17A is a schematic of the lentivirus vector engineered to express PSGL1 (P-Selectin Glycoprotein Ligand 1) and Fut7 (Fucosyltransferase, glycosylates/activates PSGL1) on MSCs and cytoplasts. The coding sequences of PSGL1 (SEQ ID NO: 16) and Fut7 (SEQ ID NO: 17) were linked by 2A sequence (SEQ ID NO: 18).
Figure 17B:
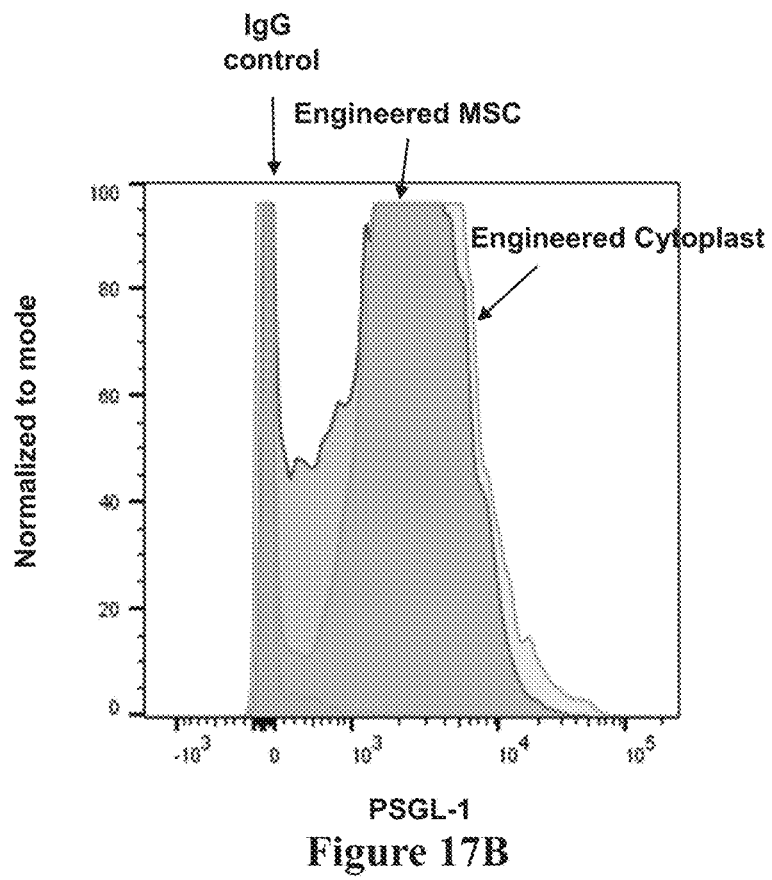
FIG. 17B is a representative flow cytometry graph showing the number of events counted over the signal strength of the cell surface PSGL1 expression by fluorescent antibody on engineered cytoplasts and engineered parental MSCs as analyzed by FlowJo.
Figure 17C:
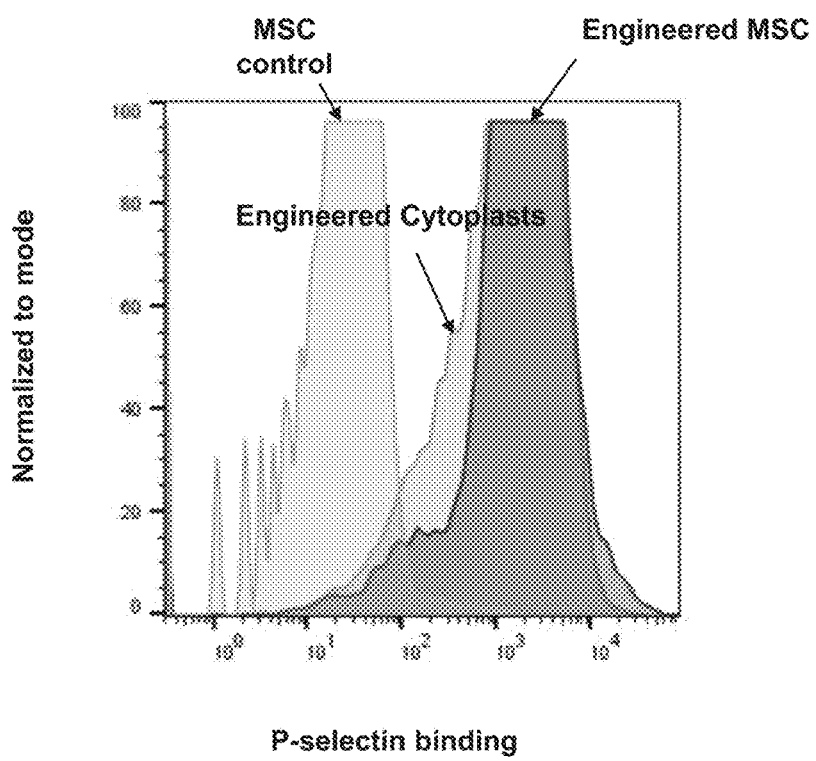
FIG. 17C is a representative graph showing cell surface binding of P-Selectin with engineered MSCs and MSC-derived cytoplasts as determined by flow cytometry. MSC control=parental MSCs. Engineered MSC=PSGL1/Fut7 engineered MSC. Engineered cytoplast=PSGL1/Fut7 engineered MSC-derived cytoplasts.
Figure 18A:
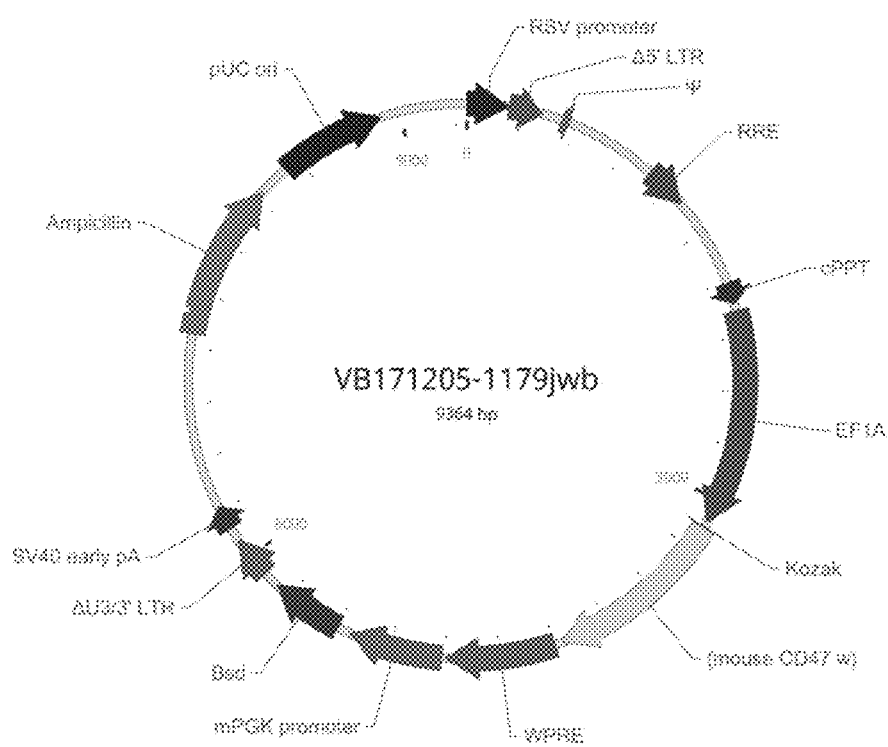
FIG. 18A is a schematic of a lentivirus vector engineered to express mCD47 (SEQ ID NO: 19) on MSCs and cytoplasts.
Figure 18B:
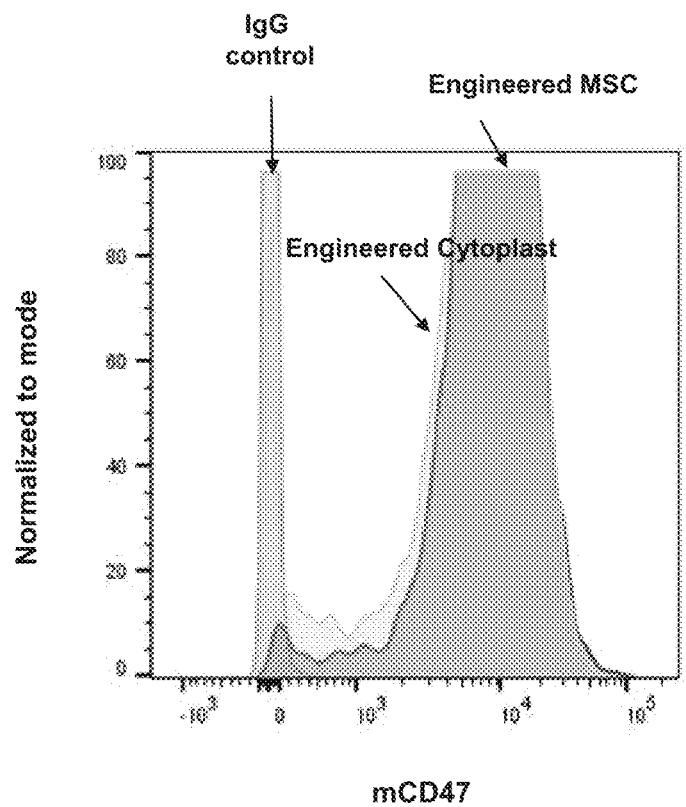
FIG. 18B is a representative flow cytometry graph showing the number of events counted over the signal strength of the cell surface of mCD47 expression on engineered cytoplasts and MSCs as analyzed by FlowJo.
Figure 18C:
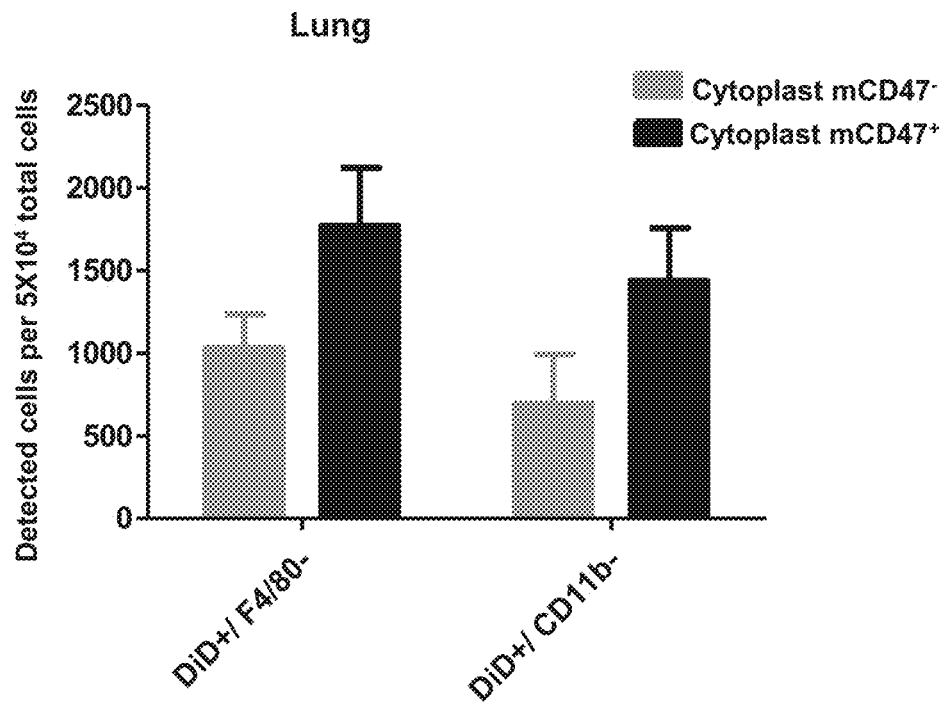
FIG. 18C is a representative bar graph showing the number of live cytoplasts (DiD+) that were not phagocytosed by macrophages (F4/80− and CD11b−), indicating that cytoplasts escaped macrophage phagocytosis in the lung. Mean±SEM; n=3. DiD dye-labeled Control cytoplasts or engineered cytoplasts (mCD47 Cytoplasts) were retro-orbitally injected into the vasculature of mice. After 24 hours, tissues were harvested and stained with two different pan-macrophage markers (F4/80 and CD11b).
Figure 18D:
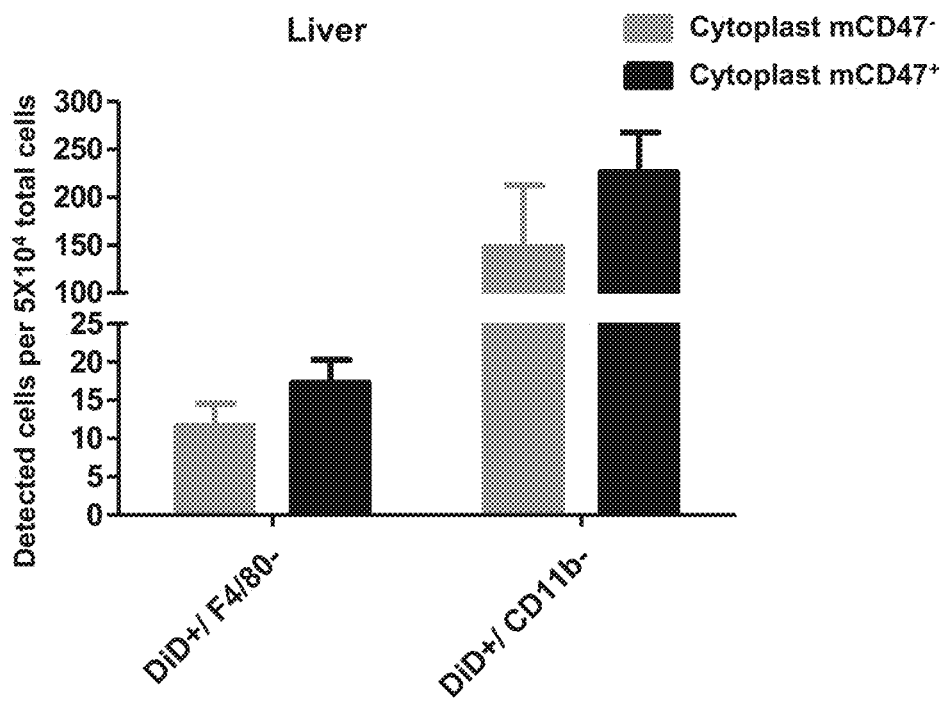
FIG. 18D is a representative bar graph showing live cytoplasts (DiD+) that were not phagocytosed by macrophages (F4/80− and CD11b−), indicating that cytoplasts escaped macrophage phagocytosis in the liver. Mean±SEM; n=3. DiD dye-labeled Control cytoplasts or engineered cytoplasts (mCD47 Cytoplasts) were retro-orbitally injected into the vasculature of mice. After 24 hours, tissues were harvested and stained with two different pan-macrophage markers (F4/80 and CD11b).

FIGS. 17A-C show that MSC-derived cytoplasts can be engineered to express functional cell adhesion proteins known to mediate cell adhesion to the inflamed vasculature. FIGS. 18A-D show that MSC-derived cytoplasts can be engineered to express cell proteins known to modulate macrophage interactions and phagocytosis of therapeutic cells.

Figure 19A:
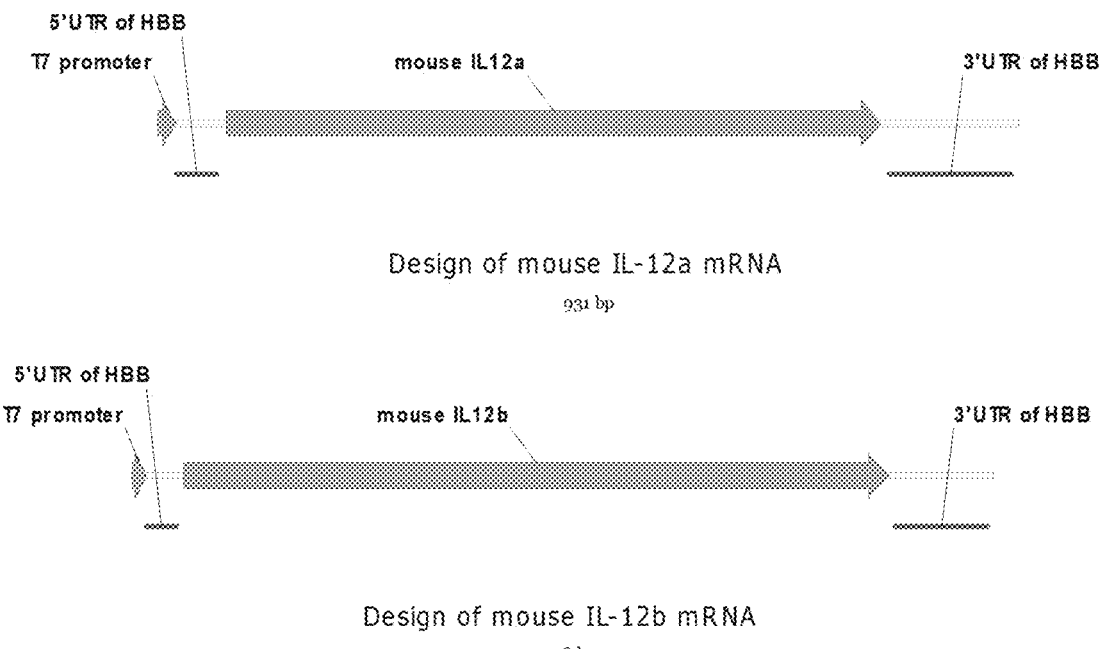
FIG. 19A is schematics of IL-12 mRNA design. Kozak sequence was added in front of the start codon of IL-12 mRNA coding region (CDS). 5'UTR and 3'UTR of human beta globin (HBB) mRNA were added respectively to the 5' and 3' end of IL-12 CDS. Artificial 5'Cap was added to the 5' end of the IL-12 mRNA and the pseudouridine modification was implemented to increase mRNA stability.
Figure 19B:
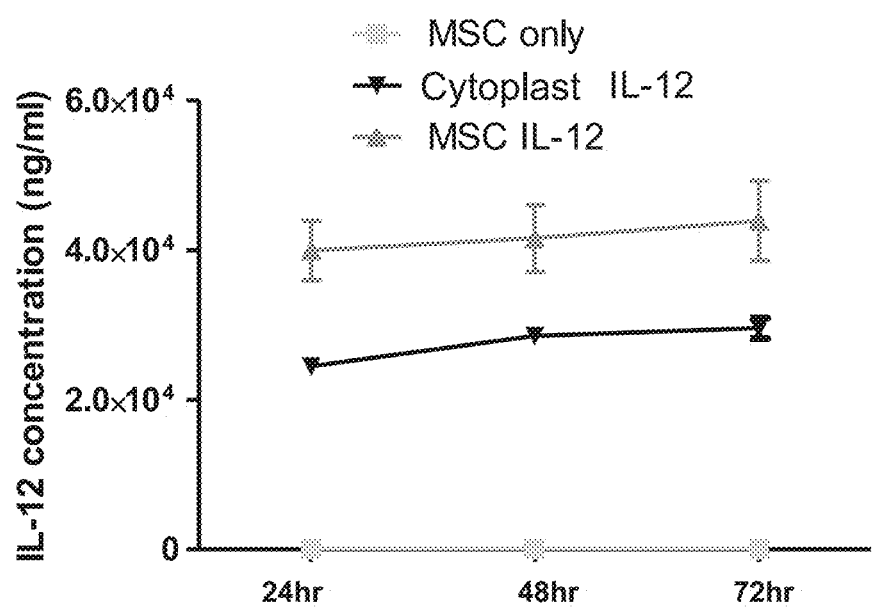
FIG. 19B is a representative line graph showing the secreted IL-12 concentration over time in conditioned media of MSCs or MSC-derived cytoplasts transfected with IL-12 mRNA and then plated at $2.5 \times 10^4$ cells/well of 24-well plate. CM was collected at the indicated time points and the secreted IL-12 concentration determined by ELISA. MSC only=CM from non-transfected control. MSC IL-12=CM from MSC transfected with IL-12 mRNA. Cytoplast IL-12=Cytoplasts transfected with IL-12 mRNA.
Figure 19C:
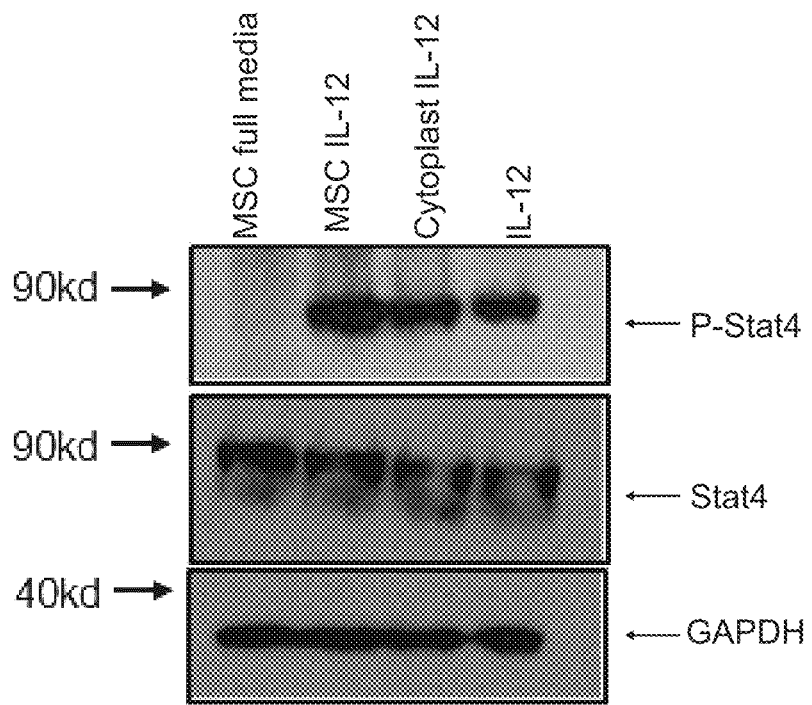
FIG. 19C is an immunoblot showing the activation of the phosphorylated/activated form of Stat4 (P-Stat4). Mouse splenocyte cells were treated with full media, purified IL-12 protein standard or the indicated CM collected from MSCs or cytoplasts engineered as in FIG. 19B for 30 minutes. MSC full medium=mouse splenocytes treated with MSC complete culture medium. MSC IL-12=treated with CM from IL-12 mRNA transfected MSCs. Cytoplast IL-12=treated with CM from IL-12 mRNA-transfected cytoplasts.

Example 5. Cytoplasts can be Engineered to Secrete Functional IL-12, and can Induce the Expression of Inflammatory Genes and Suppress Tumor Growth in a Syngeneic Mouse Model of Breast Cancer MSCs and MSC-derived cytoplasts were transfected with IL-12 mRNA. Conditioned medium (CM) was collected 24 hours, 48 hours and 72 hours post-transfection. As shown in FIG. 19B, MSC-derived cytoplasts secrete IL-12. To determine whether MSC-derived cytoplasts can secrete functional IL-12, mouse splenocytes were treated with full media, CM from MSC expressing IL-12, CM from MSC-derived cytoplasts expressing IL-12, and purified IL-12. MSC-derived cytoplasts expressing IL-12 and MSC expressing IL-12 secrete functional IL-12 that can cause phosphorylation of STAT4 in mouse splenocytes (FIG. 19C).

As shown in Example 3, administration of cytoplasts retro-orbitally was well tolerated in mice. To determine whether intratumoral administration of cytoplasts was tolerated, mice were injected either by retro-orbital or intratumoral administration. The number of deaths was recorded and classified according to injection method and cause of death (Table 3). As shown in Table below, intratumoral administration of cytoplasts was well-tolerated with an excellent safety profile.

TABLE 3

In vivo safety of cytoplast administration in mice

|  | Injection Method | Number of Animals | Number of Deaths | Cause of Death |
|---|---|---|---|---|
| Cytoplast | Retro-orbital | 36 | 0 |  |
|  | Intratumoral | 113 | 1 | Anesthesia-related |

Figure 19D:
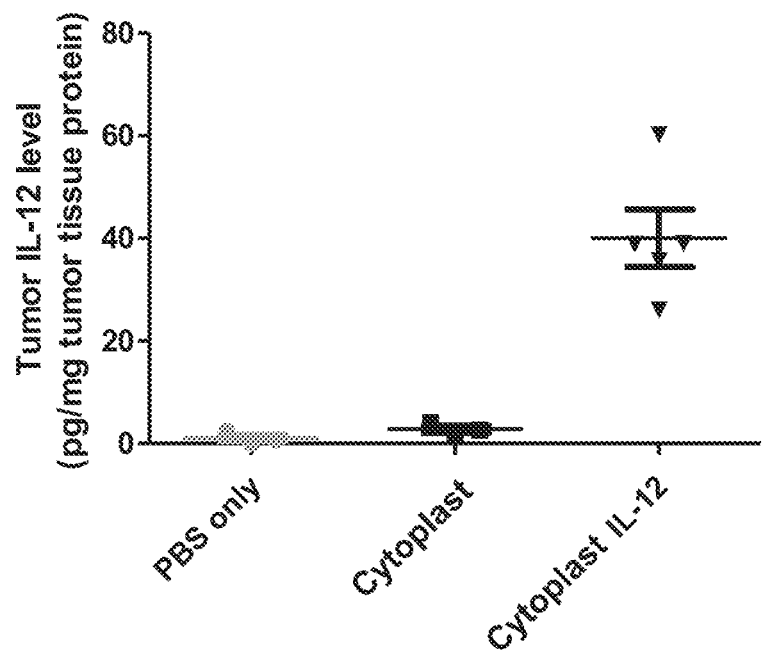
FIG. 19D is a representative scatter plot showing the concentration of secreted IL-12 cytokine per mg of tumor protein. IL-12 engineered or control cytoplasts treated as in FIG. 19B were injected into established E0771 (mouse medullary breast carcinoma) tumors growing in syngeneic C57BL/6 mice. Forty-eight hours after tumor injection, animals were euthanized and tumor samples were collected, lysed and analyzed by ELISA. PBS=samples from mice injected with PBS. Cytoplasts=samples from mice injected with non-engineered cytoplasts. Cytoplasts IL-12=samples from mice injected with cytoplasts engineered to express IL-12 cytokine.

Next, MSC-derived cytoplasts expressing IL-12 and empty MSC-derived cytoplasts were injected into established E0771 subcutaneous tumors. Forty-eight hours after injection, all mice were euthanized, and tumor samples were collected. As shown in FIG. 19D, tumor IL-12 was detected in tumors isolated from mice that were injected with MSC-derived cytoplasts expressing IL-12, whereas little to no tumor IL-12 was detected in tumors isolated from mice that were injected with empty MSC-derived cytoplasts. Taken together, these results indicate that MSC-derived cytoplasts can produce, secrete and deliver clinically relevant levels of therapeutic cytokines to a diseased tissue in a preclinical mouse model.

Figure 20A:
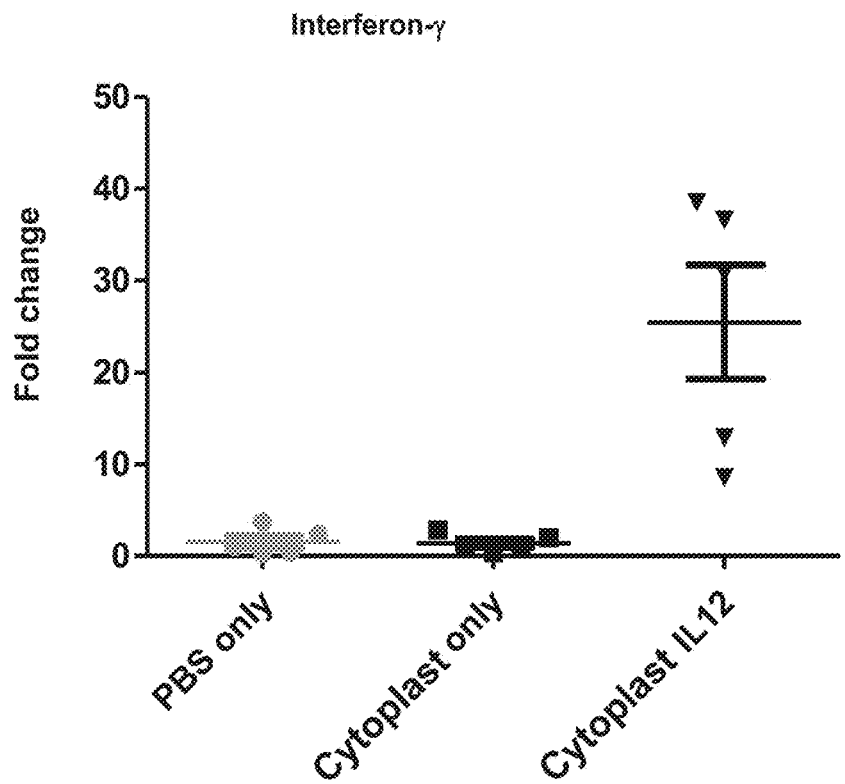
FIG. 20A is a scatter plot showing the fold change of expression for interferon-γ mRNAs. MSC-derived cytoplasts engineered to express IL-12 or control cytoplasts without IL-12 were injected into established E0771 tumors growing in syngeneic C57BL/6 mice. Forty-eight hours after injection, animals were euthanized and tumor samples were collected, lysed and analyzed by Real-time RT-PCR. PBS=samples from mice injected with PBS. Cytoplasts=samples from mice injected with non-engineered cytoplasts. Cytoplasts IL-12=tumor samples from mice injected with cytoplasts engineered to express IL-12 cytokine. Each dot represents a mouse tumor sample. Mean±SEM; n=5.
Figure 20B:
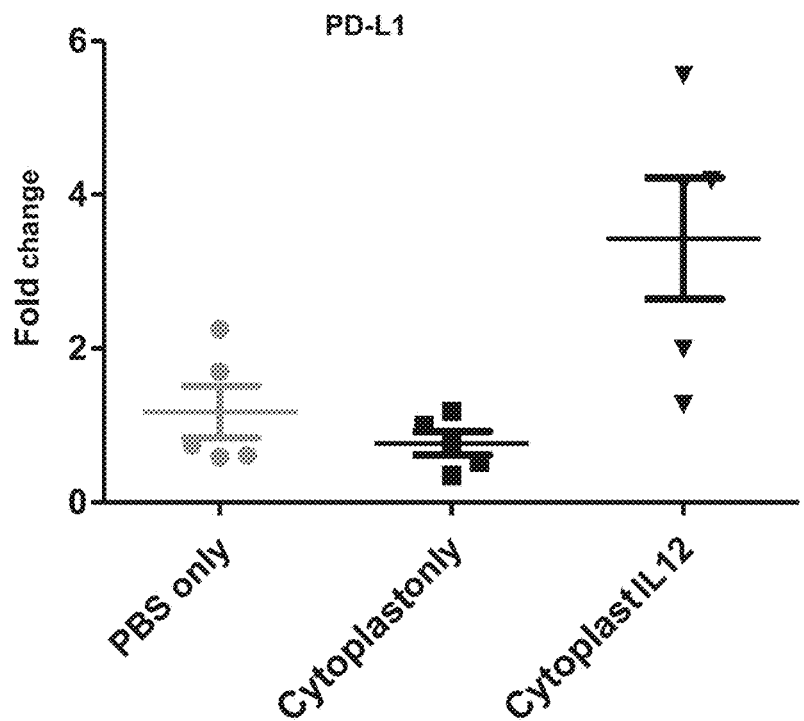
FIG. 20B is a scatter plot showing the fold change of expression for PD-L1 mRNAs. MSC-derived cytoplasts engineered to express IL-12 or control cytoplasts without IL-12 were injected into established E0771 tumors growing in syngeneic C57BL/6 mice. Forty-eight hours after injection, animals were euthanized and tumor samples were collected, lysed and analyzed by Real-time RT-PCR. PBS=samples from mice injected with PBS. Cytoplasts=samples from mice injected with non-engineered cytoplasts. Cytoplasts IL-12=tumor samples from mice injected with cytoplasts engineered to express IL-12 cytokine. Each dot represents a mouse tumor sample. Mean±SEM; n=5.
Figure 20C:
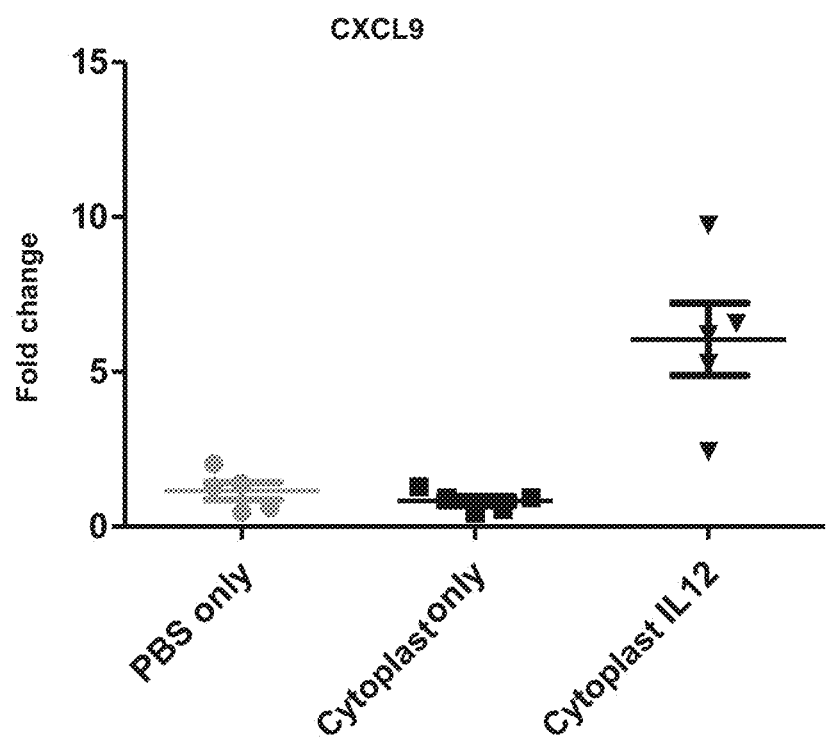
FIG. 20C is a scatter plot showing the fold change of expression for CXCL9 mRNAs. MSC-derived cytoplasts engineered to express IL-12 or control cytoplasts without IL-12 were injected into established E0771 tumors growing in syngeneic C57BL/6 mice. Forty-eight hours after injection, animals were euthanized and tumor samples were collected, lysed and analyzed by Real-time RT-PCR. PBS=samples from mice injected with PBS. Cytoplasts=samples from mice injected with non-engineered cytoplasts. Cytoplasts IL-12=tumor samples from mice injected with cytoplasts engineered to express IL-12 cytokine. Each dot represents a mouse tumor sample. Mean±SEM; n=5.
Figure 20D:
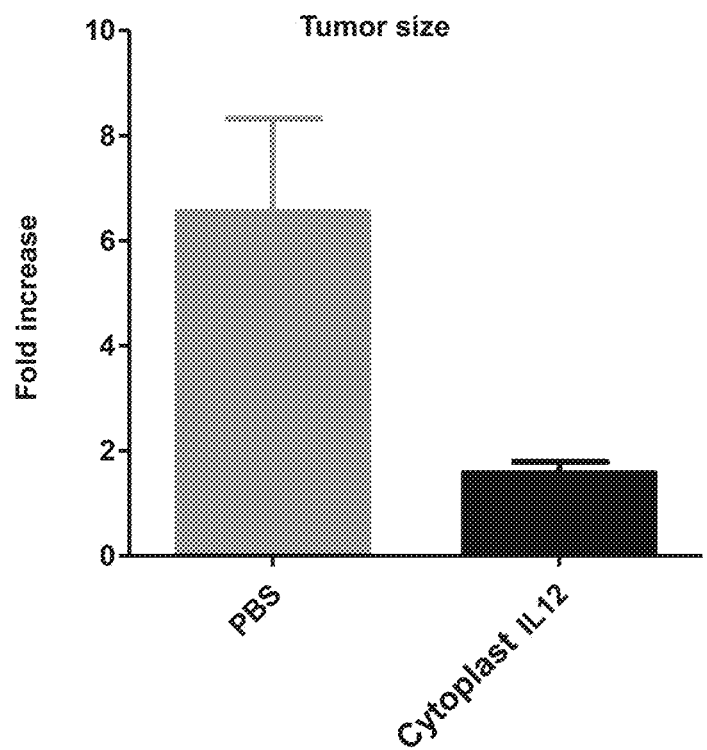
FIG. 20D is a bar graph showing the fold change of E0771 subcutaneous tumor sizein C57Bl/6 mice that were injected intratumorally with $3\times10^6$ IL-12 engineered cytoplasts (Cytoplasts IL12 group) or PBS (PBS group) on day 11, day 14, and day 18 after tumor cell inoculation. The fold change of tumor size=Tumor volume of day 20/Tumor volume of day 11. Mean±SEM; n=5.

FIGS. 20A-C show that samples taken from mice injected with cytoplasts engineered to express IL-12 cytokine express interferon gamma (IFNγ), PD-L1 and CXCL9, whereas samples taken from mice that received only PBS or empty cytoplasts expressed low levels of IFNγ, PD-L1 and CXCL9. These data indicate that MSC-derived cytoplasts engineered to express IL-12 induced an inflammatory response within the injected tumor. FIG. 20D shows a decrease in tumor size following injection of MSC-derived cytoplasts engineered to express IL-12.

Figure 21A:
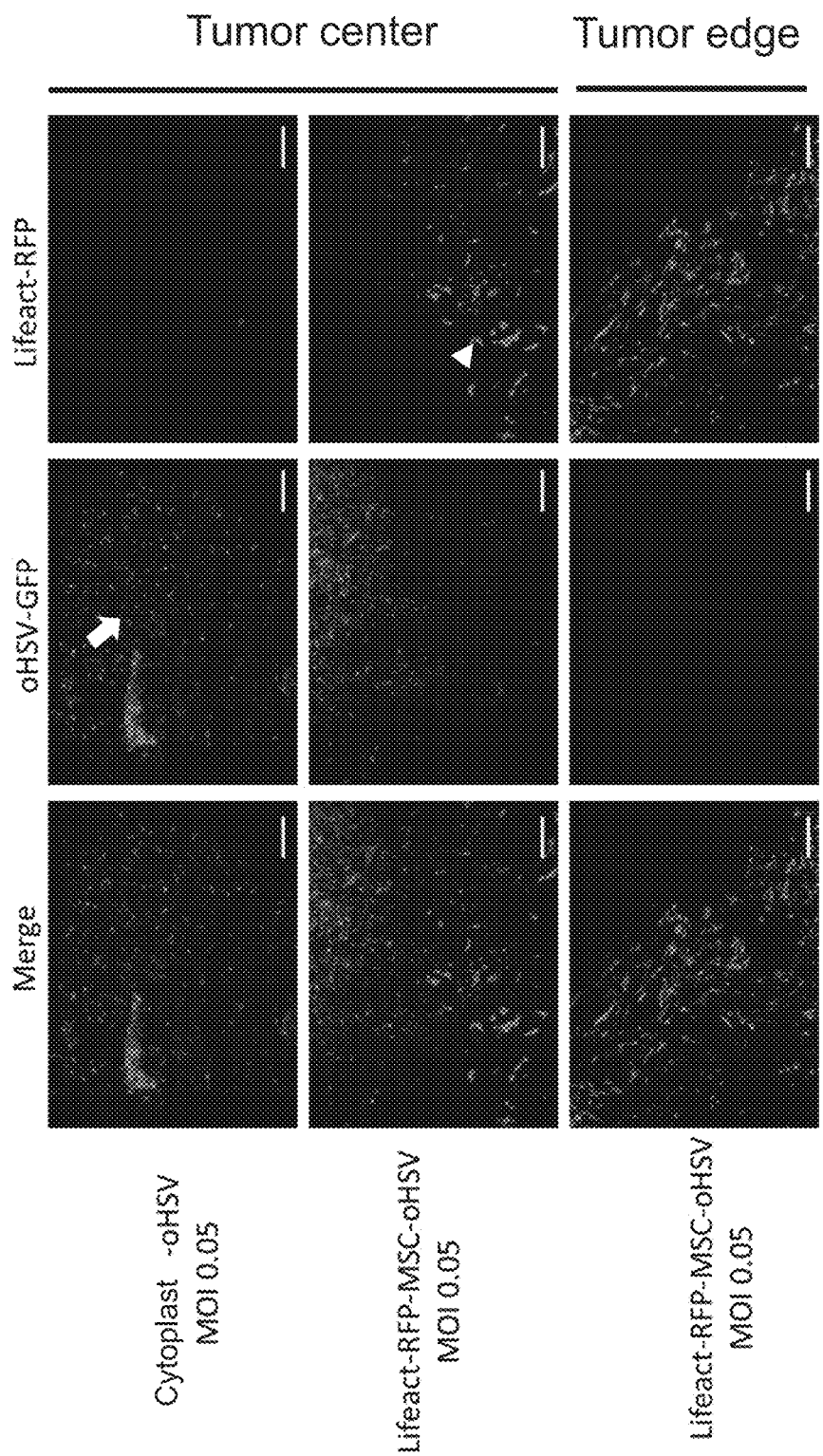
FIG. 21A are epifluorescence microscopy images taken 7 days after Lifeact-RFP expressing MSCs or cytoplasts infected with 0.05 MOI of the oncolytic herpes simplex virus encoding GFP (oHSV-GFP) were injected into subcutaneous U87 glioblastoma tumors in nude mice. Arrowhead represents RFP-positive cells (indicating MSC survival and proliferation inside the tumor). Arrow represents GFP-positive tumor cells (successful transfer of oHSV-GFP from MSC or cytoplast to tumor cell). Scale bar=100 µm.
Figure 21B:
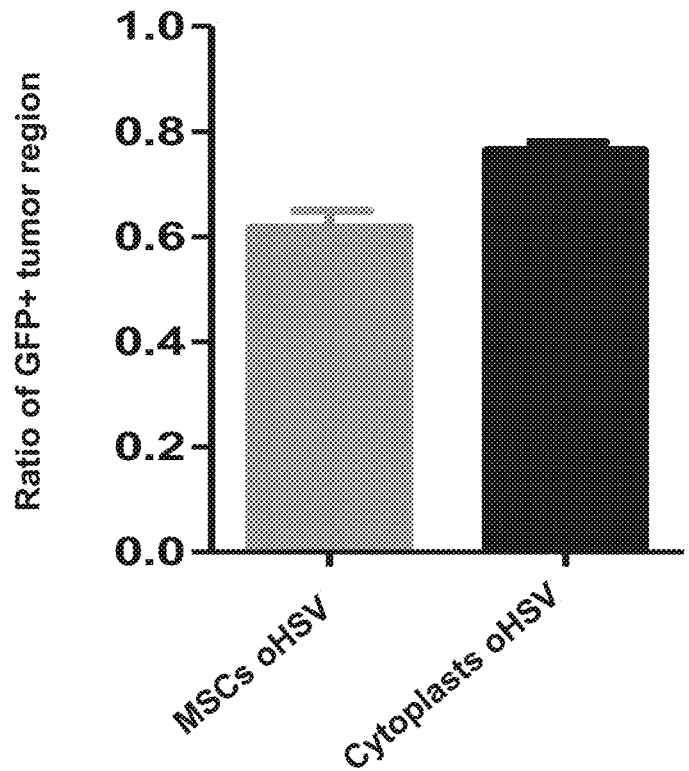
FIG. 21B is a bar graph showing percentage of GFP-positive tumor area for tumors treated as in FIG. 21A, which represents the portion of tumor cells infected by MSCs or cytoplasts carrying the oHSV-GFP virus.
Figure 21C:
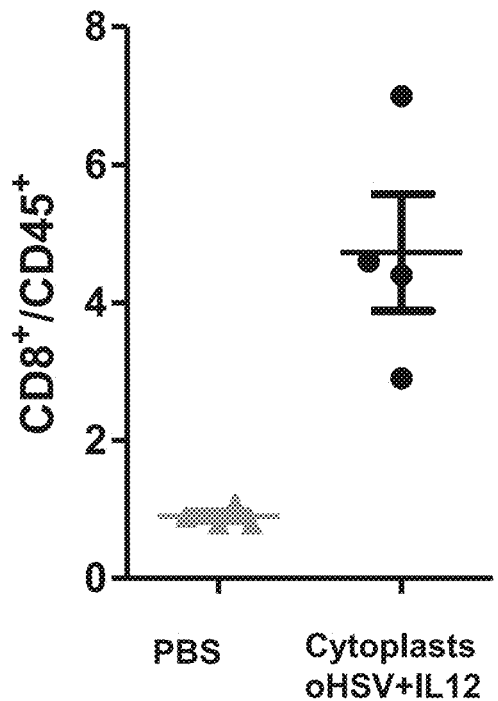
FIG. 21C is a scatter plot showing the ratio of $CD8^+$ effector T lymphocyte cells out of total CD45+(immune cells) present in tumors injected with engineered cytoplasts, as analyzed by flow cytometry. Established subcutaneous E0771 tumors in C57Bl/6 mice were injected intratumorally with oHSV-transfected and IL-12 engineered cytoplasts or PBS only injection (negative control).

FIGS. 21A-C show that MSC-derived cytoplasts can be loaded with oncolytic viruses and can deliver such viruses to tumors growing in immunocompromised and immunocompetent mice, which in combination with IL-12 secretion promotes infiltration of cytotoxic CD8+ T cells into the tumor. Regarding FIG. 21A, it is notable that very few cytoplasts can be detected in the tumor after 7 days, whereas a large number of MSCs are present in the center (injection site) and at the outer edge of the growing tumor.

Figure 22A:
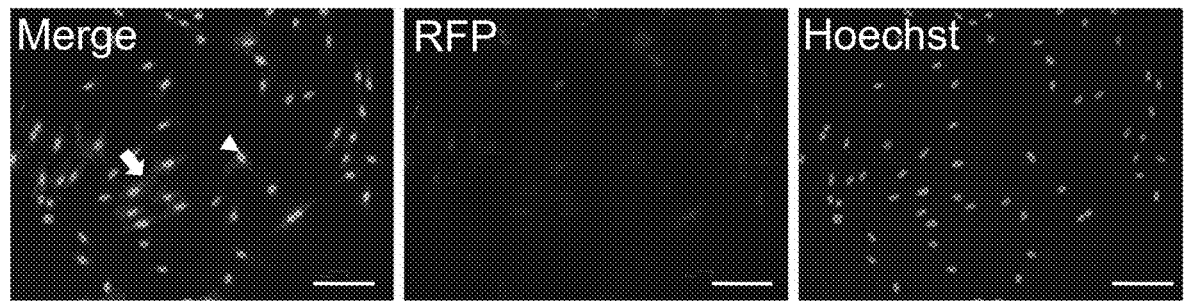
FIG. 22A are representative epifluorescence microscopy images showing RFP expression in nucleated MSC cells successfully fused with Cre-engineered cytoplasts. MSC-derived cytoplasts were genetically engineered to express Cre recombinase, then electrofused at a ratio of 3:1 (under 500 V for 100 µs for 3 pulses) with hTERT-MSCs engineered to express Loxp-GFP-stop-Loxp-RFP. Fluorescence images were taken after sorting for RFP and staining with Hoechst. Arrowhead indicates Hoechst-stained nucleus, arrow indicates positive RFP fluorescence indicating successful Cre-induced expression of RFP. Scale bar=100
Figure 22B:
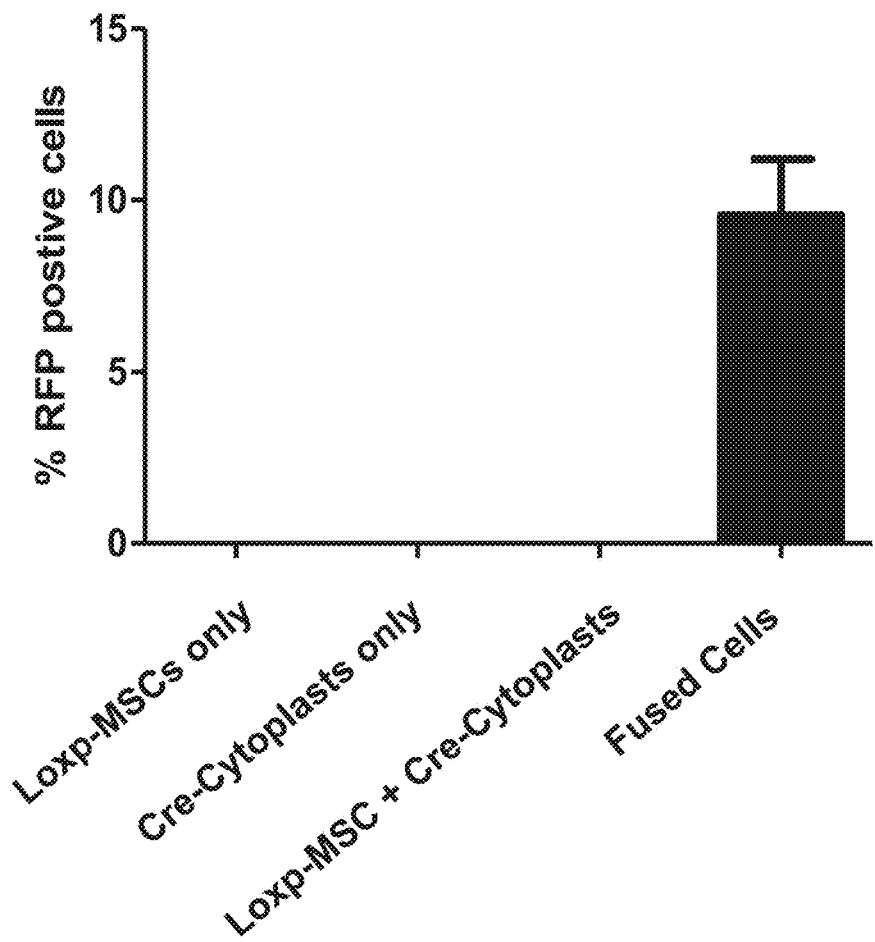
FIG. 22B is a bar graph showing the percentage of RFP+(fused) cells out of total cells. Loxp MSC only=single culture of Loxp-GFP-stop-Loxp-RFP—hTERT-MSCs. Cre Cytoplasts only=single culture of cytoplasts engineered to express Cre recombinase. Co-culture=Co-culturing of Loxp MSCs and Cre cytoplasts for 48 hours. Fusion=Electrofusion of Loxp MSC and Cre cytoplasts. Mean±SEM; n=4.
Figure 23:
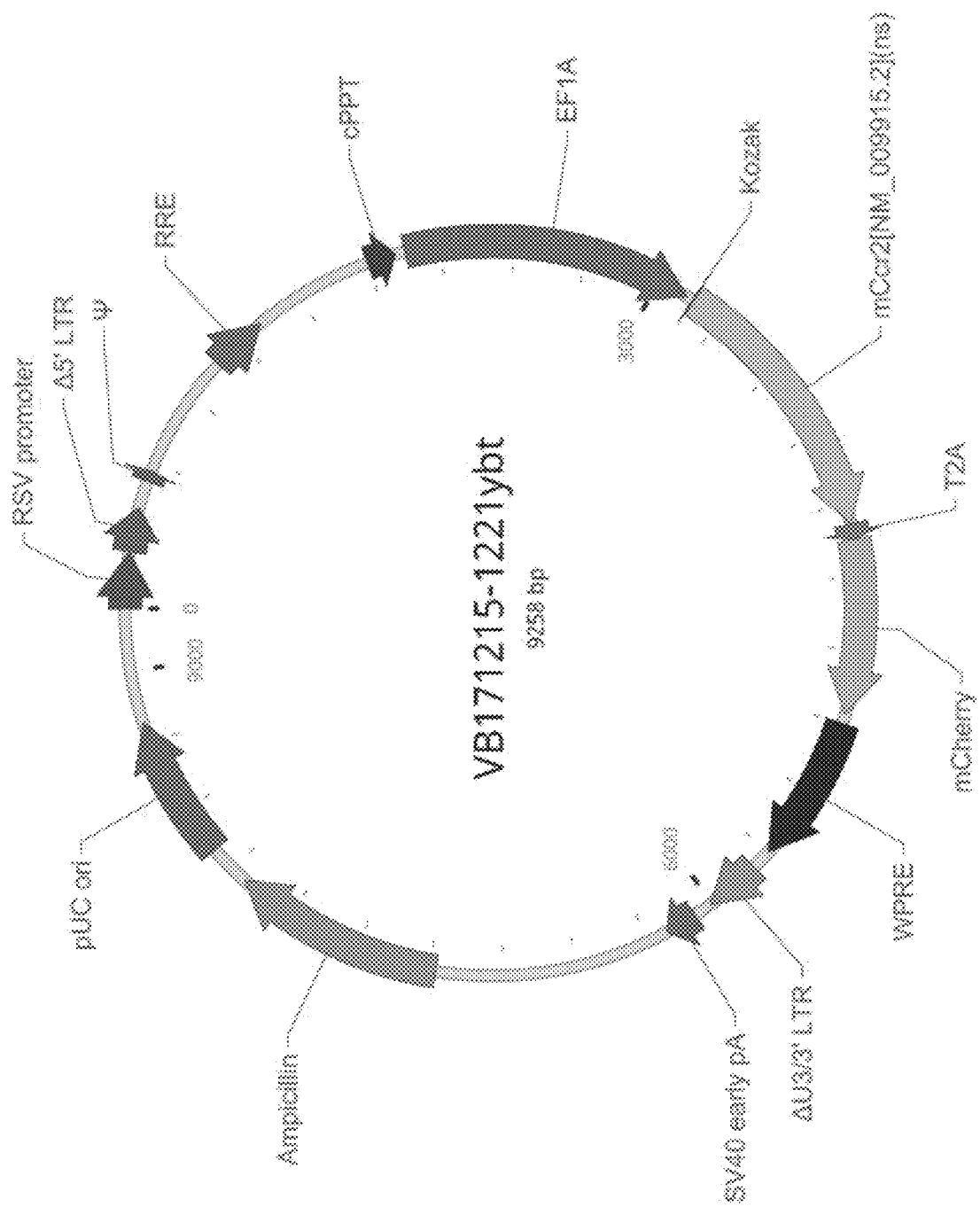
FIG. 23 is a schematic of the lentivirus vector engineered to express mCCR2 (SEQ ID NO: 20) on MSCs and cytoplasts.

FIGS. 22A-B show that genetically engineered MSC-derived cytoplasts can deliver gene editing proteins to regulate gene function in host cells following cytoplast-host cell fusion. These data illustrate the potential of cytoplast-based cell therapies to deliver gene editing components to modify normal or mutant genes in cells.

Enucleation of Mesenchymal Stem Cells (MSC)

This protocol was modified from Methods in Cell Biology Volume 14, 1976, Pages 87-93 Chapter 7 Enucleation of Mammalian Cells in Suspension (Michael H. Wigler, Alfred I. Neugut, I. Bernard Weinstein).

Preparation of 50% Ficoll solution: In a glass beaker shielded from light, grams of Ficoll (PM400, GE Healthcare 17-0300-500) were dissolved in an equivalent number of milliliters ultrapure water (Invitrogen 10977-015) by continual magnetic stirring for 24 hours at room temperature. The mixture was then autoclaved for 30 minutes. Once the mixture was cooled, it was stirred again to ensure uniform consistency. The refractive index was measured on a refractometer (Reichert 13940000), and was in the range of 1.4230-1.4290. Aliquots were stored at −20 degrees Celsius.

Preparation of 2×MEM: For each 50 ml quantity, 10 mL 10×MEM (Gibco, 11430-030), 2.94 mL exactly Sodium Bicarbonate (7.5%, Gibco, 25080-094), 1 mL 100× Pen-Strep (Gibco 15140-122) and 36 mL ultrapure water (Invitrogen 10977-015) was used. The solution was then filtered through 0.22 um membrane flask (Olympus 25-227) and stored at 4 degrees Celsius.

On the day before enucleation, MSCs were seeded at 2.5 M per 15 cm plate (Olympus 25-203) in 20 mL MSC medium [MEM 1× (Gibco 12561-056); 16.5% premium FBS (Atlanta Biologics S1150); 1% HEPES 1M (Gibco 15630-80); 1% Anti-Anti 100× (Gibco 15240-062); 1% Glutamax 100× (Gibco 35050-061)]. Next, Cytochalasin B (Sigma Aldrich C6762) was added to the 2×MEM (2 μM/mL final concentration).

Preparation of Ficoll gradients: 2× CytoB was added to 50% Ficoll aliquots at 1:1 dilution to make 25% Ficoll stock concentration. Next, 17%, 16%, 15% and 12.5% Ficoll were made by diluting 25% Ficoll with the appropriate volume of 1×MEM buffer (2×MEM containing Cytochalasin B added to ultrapure water at 1:1 dilution). The dilutions were equilibrated in a CO2 incubator for at least 1 hour covered with loose cap. The Ficoll gradients were then poured into 13.2 mL ultra-clear tubes (Beckman, 344059), and incubated overnight (6-18 hours) in the CO2 incubator.

On the day of enucleation, 12-25M MSC (ideally 20M) were collected into each tube for enucleation. Media was aspirated, and the cells washed once with phosphate buffered saline (PBS) (GIBCO 14190-144). Five mL of TrypLE-Select (Gibco, 12563011) was added to each plate, and incubated up to 5 minutes. When 90% of the cells were detached, 5 mL full MSC media was added, and the cells were collected into 50 ml tubes (3-4 plates/tube). The tubes were then centrifuged at 1, 200 rpm for 5 minutes. The pellet was resuspended in 10 mL PBS. Cells were counted, pelleted, and re-suspended with 12.5% Ficoll. Next, the cell-Ficoll mixture was dropwise passed through a 40 um cell strainer (Falcon 352340) into a new 50 mL tube. Using a syringe, 3.2 mL of cell suspension was slowly loaded onto the pre-made gradients. One mL of 1×MEM buffer was added at the final (top) layer with syringe. The tubes were then loaded into rotor buckets, balanced, and run in the ultracentrifuge (Beckman, L8M) for 60 minutes, 26,000 rpm, 31° C., Accel 7, Deccel 7. At the end of the centrifugation, there were three layers: one near the top of the 12.5% (cytoplasts and debris), one near the 12.5/15% interface (cytoplasts), and a pellet at the bottom of the 25% (karyoplasts). The layers above 15% Ficoll solution were collected into 15 ml conical tubes. The collected layers are then diluted with more than 4 volumes warm serum-free MSC medium (i.e. 3 mL of Ficoll and filled with up to 15 mL media). After gently mixing, the mixture was pelleted for 10 minutes at 1,200 rpm. Following three washes with warm serum-free MSC medium, the cells were resuspended in media according to the experimental protocol, e.g., transfection media vs. migration media vs. serum free media vs. full media. Efficiency of enucleation was determined in a 12-well plate by adding full MSC media with 1:2000 dilution Vybrant® Dyecycle™ Green (Molecular Probes V35004) or 1:5000 dilution Hoechst 33342. A small volume of each layer was added to each well and allowed to attach/stain for 10 minutes in the incubator. The percentage of negative cytoplasts per population was determined by epifluorescent microscopy.

Cytoplast mRNA Transfection

1 M cytoplasts were suspended with warm 1 ml amino acid-free α-MEM full medium (ThermoFisher 12561056; 16.5% Premium fetal bovine serum (FBS), 1% Glutamax (Gibco 35050061), 1% HEPES (Gibco 15630080)). 1 µg mRNA was diluted with warm opti-MEM and mixed with pipet at least 20 times. 4 µl lipofectamine-3000 (ThermoFisher L300015) was added to 46 µl warm opti-MEM (ThermoFisher 31985062) and mixed with pipet for at least 20 times. The ratio of mRNA and lipofectamine-3000 was 1:4 (w/v). The mRNA and lipofectamine-3000 dilutions were mixed with pipet for at least 20 times and incubated at room temperature for 15 minutes. The mRNA and lipofectamine-3000 mixture was added to the cytoplast suspension, mixed well and incubated at 37° C. for 30 minutes. The suspension was shaken every 5 minutes to prevent cell clumping. After incubation, the cells were centrifuged, and re-suspended in normal α-MEM full medium (16.5% Premium FBS, 1% Antibiotic-Antimycotic, 1% Glutamax, 1% HEPES) or PBS.

Cytoplast siRNA Transfection

1 M cytoplasts were suspended with warm 1 ml A/A free α-MEM full medium (16.5% Premium FBS, 1% Glutamax, 1% HEPES). Two µl siRNA was diluted with warm opti-MEM and mixed with pipet at least 20 times. Eight µl lipofectamine-3000 was diluted with 92 µl warm opti-MEM and mixed with pipet at least 20 times. The ratio of siRNA and lipofectamine-3000 was 1:4 (v/v). The siRNA and lipofectamine-3000 dilutions were mixed with pipet at least 20 times and incubated at room temperature for 15 minutes. The siRNA and lipofectamine-3000 mixture was added to the cytoplast suspension, mixed well and incubated at 37° C. for 20 minutes. The suspension was shaken every 5 minutes to prevent cell clumping. After a 20 minute incubation, the cells were centrifuged, and re-suspended with normal α-MEM full medium (16.5% Premium FBS, 1% Antibiotic-Antimycotic, 1% Glutamax, 1% HEPES).

Generation of Oncolytic Virus Infected Cytoplasts

One day before enucleation (usually 18 hrs before enucleation), $2.5*10^6$ hTERT-MSCs were seeded on a 15-cm dish. Roughly two hours after seeding, the cells were washed once with PBS. Cells were then infected with oHSV-GFP (Imams OV3001) at different MOIs (0.05 or 0.5 for example) with 8 mL serum free opti-MEM. Next, cells were incubated at 37° C. for 2 hours with occasionally shaking. The virus inoculum was then discarded. 20 mL pre-warmed full culture medium (α-MEM, 16.5% Premium FBS, 1% Antibiotic-Antimycotic, 1% Glutamax, 1% HEPES) was added to each well. The cells were incubated at 37° C. until enucleation.

Lentivirus Overexpressing Functional Proteins in Cytoplasts

Target cells were plated in one well of 6-well plate at density of $1-2\times10^5$ cells/well, or 10 cm plate with 0.5-1 M MSCs. The next day, the concentrated recombinant lentivirus was thawed in a 37° C. water bath and removed from the bath immediately once thawed. The cells were then washed with PBS 3 times. 200 µL serum free medium or 2 mL serum free medium (1:1250 SureENTRY) was added. The target cells were infected in a 6-well plate with MOI 10:1. The next day, the viral supernatant was removed and the appropriate complete growth medium was added to the cells. After 72 hours incubation, the cells were subcultured into 2×100 mm dishes. The appropriate amount of selection drug (i.e. puromycin) was added for stable cell-line generation. 10-15 days after selection, clones were picked for expansion and were screened for positive ones. The selected positive clones were expanded for enucleation. Engineered cytoplasts were prepared as outlined above. The target protein expression on cytoplasts was determined by ordinary biochemical methods or functional assays, e.g., fluorescent activated cell sorting (FACS), western blot, or Boyden chamber assay.

Peptide Loading into Cytoplasts $1\times10^5$/ml per well were plated onto a 4-chamber glass slide (LabTek II 4-chamber glass slide, 155383) in full MSC media [MEM 1× (Gibco 12561-056); 16.5% premium FBS (Atlanta Biologics S1150); 1% HEPES 1M (Gibco 15630-80); 1% Anti-Anti 100× (Gibco 15240-062); 1% Glutamax 100× (Gibco 35050-061)]. Cells were allowed to attach for at least 1 hour or overnight. Cells were then rinsed with PBS (Gibco 14190-144). Arg9(FAM) (10 mM, Anaspec, AS-61207) was diluted in full media to a total concentration of 1:100 (100 uM). Cytoplasts were then incubated for 1 to 2 hours, and rinsed 3 times with PBS. Hoechst 33342 (Invitrogen) was added at a 1:5000 dilution in full media for at least 10 minutes. Cells were then washed with PBS and imaged by epifluorescent microscopy.

Generation of Pre-Clinical Syngeneic Tumor Model in Immune Competent Mice

A small patch of fur on each side of the mouse's flank (from the level of the elbow to above the thigh and just onto the abdomen to halfway across the back) was shaved. Excess fur was wiped away with an alcohol wipe. Using 1 mL tuberculin syringe with 27G ½" needle, 1M/100 µL E0771 cells were injected into each side of the mouse. Mice were monitored until tumors reached 0.7-1.0 cm diameter, roughly 10-20 days later.

Intratumoral Delivery of Therapeutic Cytoplasts

Engineered cytoplasts (i.e. loaded with IL-12 mRNA) were resuspended in PBS at desired concentration, e.g., 3M/50 uL. On the day of injection, animal weight and tumor dimensions were measured. Engineered cytoplasts were injected into the center of the tumor. Mice were monitored; tumors and body weight were measured every 2-3 days.

Intravenous Delivery of Therapeutic Cytoplasts

Engineered cytoplasts (i.e. loaded with IL-12 mRNA) were resuspended in PBS at desired concentration, e.g., 3M/50 µL. The maximum recommended injection volume was 100 µL. Injections were performed with a 1 mL tuberculin syringe and 27G ½" or 28G ½" needle. Institutional Animal Care and Use Committee (IACUC) protocols were followed for intravenous (IV) injection. Retro-orbital injections were performed under anesthesia with ketamine/xylazine intraperitoneal (IP) injection or isofluorane inhalation. Tail vein injections were performed using a restraint device.

Example 6. 3D-Cultured MSC can be Enucleated and 3D-Derived Cytoplasts Show Better Biodistribution In Vivo MSCs were cultured in 3D-hanging drops (3D MSCs) then enucleated to generate 3D cytoplasts. The 3D culture protocol of MSC by hanging drops is modified from Curr Protoc Stem Cell Biol. 2014 Feb. 6; 28: Unit-2B.6. (Thomas J. Bartoshl and Joni H. Ylostalo).

Healthy MSCs were harvested from 2D-cultured plates by Trypsin and resuspended in fresh α-MEM (ThermoFisher 12561056) full medium (16.5% Premium FBS, 1% Antibiotic-Antimycotic, 1% Glutamax, 1% HEPES) at 1.43 million cells/ml. The lid of a 15 cm plate was opened completely and 20 ml PBS was added to the plate. A multichannel pipette was used to make droplets on the lid of the plate at 35 μl per droplet (approx. 50,000 cells/droplet). About 100-120 droplets were placed on each lid. The lid was closed and the plate was placed back into the incubator. Droplets were cultured for 2 days, then harvested by cell lifter and collected into 15 ml tubes (approx. 300 droplets per tube). The tubes were centrifuged for 5 minutes at 1,200 rpm. The supernatant was removed and the tubes were washed twice with PBS. All PBS was then removed and 7.5 ml of freshly thawed 0.25% Trypsin-EDTA (ThermoFisher 25200114) was added to each tube. The tubes were incubated in a water bath for 4 minutes. The droplets were gently pipetted with 1 ml pipettes with low-retention tips about 10-20 times and incubated in the water bath for another 4 minutes. The droplets were again gently pipetted with 1 ml pipettes with low-retention tips about 10-20 times until most of the droplets were dissociated. 7.5 ml of full serum medium (GlutaMAX Supplement (Gibco 35050061); Fetal Bovine Serum—Premium Select (Atlanta Biologicals S11550); HEPES (1 M) (Gibco 15630080); antibiotic-Antimycotic (100×) (Gibco 15240062)) was added to each tube and the tubes were centrifuged for 10 minutes at 1,200 rpm. The dissociated cells were washed with 10 ml of full serum medium and the cells were resuspended with 5 ml full serum medium. The cells were passed through a 70 μm cell filter and then the filter was washed with 5 ml full serum medium. The cells were counted and resuspended with pre-treated 12.5% Ficoll at more than 10M/ml. 30-40M cells were used for each enucleation tube. Subsequently, the protocol for enucleation described above was followed.

Figure 24A:
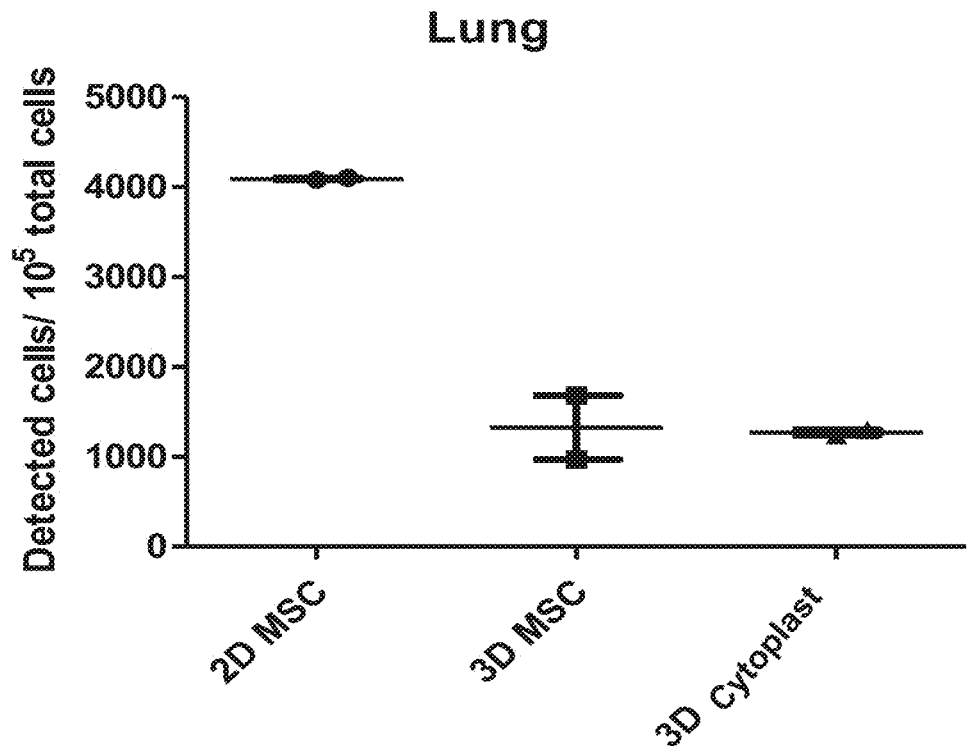
FIG. 24A is a representative scatter plot showing the number of DiD-labeled MSCs or cytoplasts detected in the lung. MSCs were cultured under standard adherent conditions (2D) or in suspension by the handing drop method (3D) to generate 3D cytoplasts. MSCs and cytoplasts were labeled with Vybrant® DiD dye and retro-orbitally injected into the vasculature of C57BL/6 mice. Tissues were harvested after 24 hours and cell suspensions analyzed by flow cytometry. Mean±SEM; n=2.
Figure 24B:
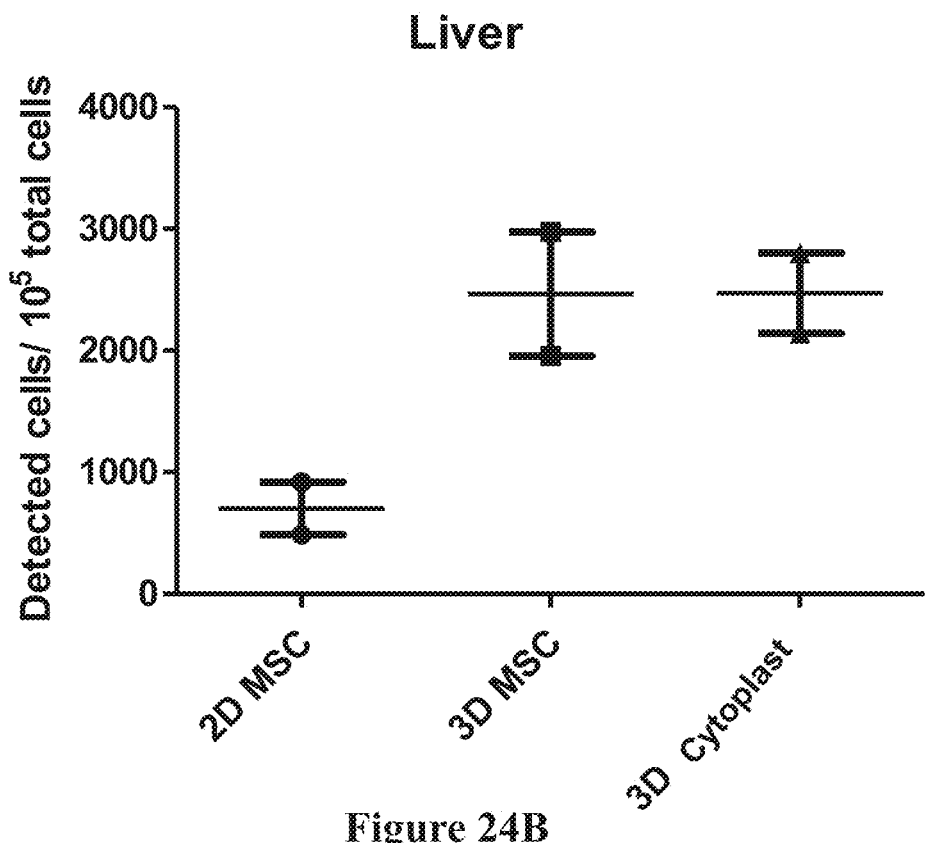
FIG. 24B is a representative scatter plot showing the number of DiD-labeled MSCs or cytoplasts detected in the liver. MSCs were cultured under standard adherent conditions (2D) or in suspension by the handing drop method (3D) to generate 3D cytoplasts. MSCs and cytoplasts were labeled with Vybrant® DiD dye and retro-orbitally injected into the vasculature of C57BL/6 mice. Tissues were harvested after 24 hours and cell suspensions analyzed by flow cytometry. Mean±SEM; n=2.
Figure 24C:
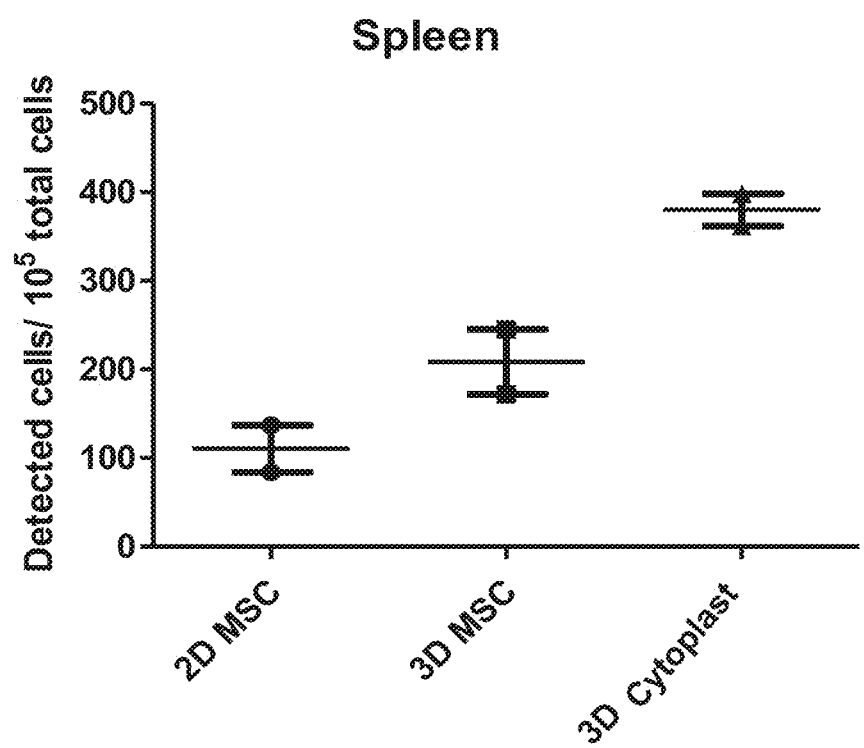
FIG. 24C is a representative scatter plot showing the number of Vybrant® DiD-labeled MSCs or cytoplasts detected in the spleen. MSCs were cultured under standard adherent conditions (2D) or in suspension by the handing drop method (3D) to generate 3D cytoplasts. MSCs and cytoplasts were labeled with DiD dye and retro-orbitally injected into the vasculature of C57BL/6 mice. Tissues were harvested after 24 hours and cell suspensions analyzed by flow cytometry. Mean±SEM; n=2.
Figure 25A:
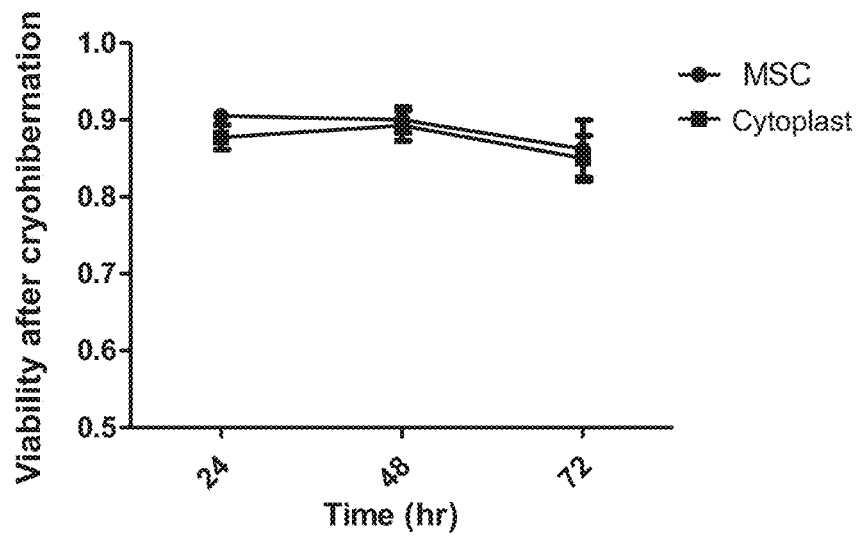
FIG. 25A is a representative line graph showing the viability of MSC and MSC-derived cytoplasts immediately after recovery from cryohibernation at 4 degrees Celcius for the indicated amounts of time. Viability was assessed in an automated cell count (Cell Countess) using Trypan blue dye exclusion and displayed as a ratio to the number of input cells.
Figure 25B:
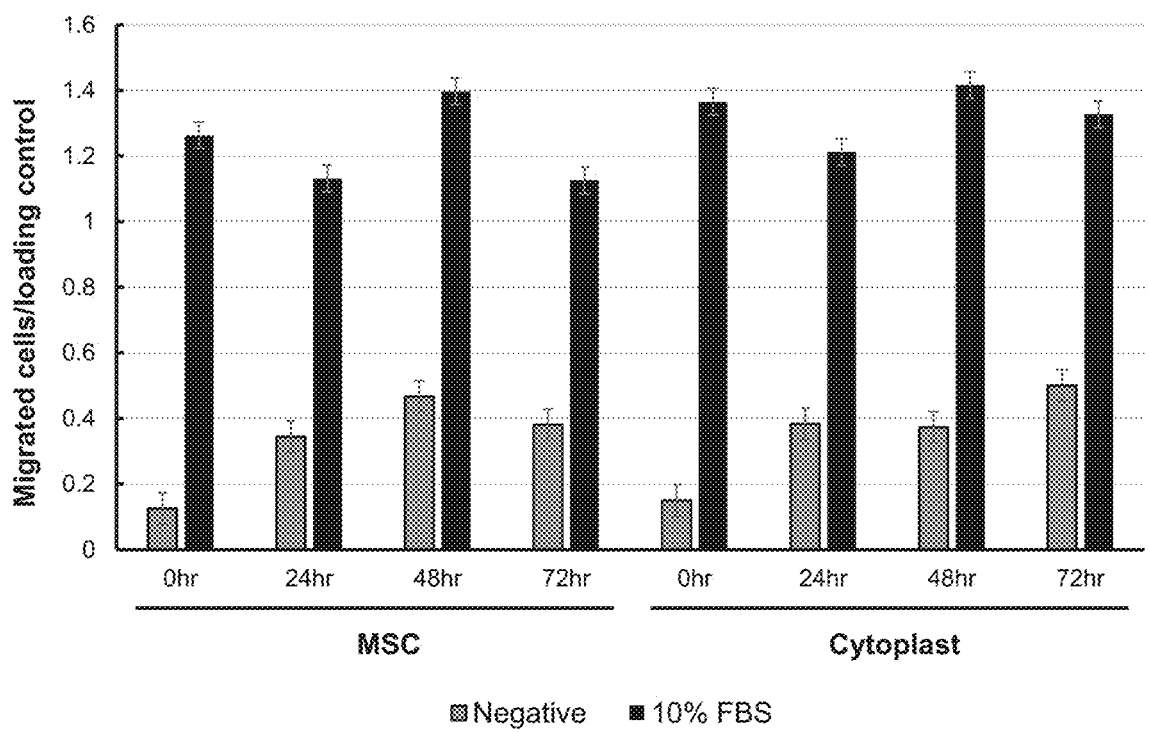
FIG. 25B is a representative bar graph comparing the migrated MSC and MSC-derived cytoplasts in a Boyden chamber assay immediately after recovery from cryohibernation at 4 degrees Celcius for the indicated amounts of time. Cells and cytoplasts were allowed to migrate for 3 hours with either no serum (negative control) or 10% premium FBS (P-FBS) as a chemoattractant in the bottom chamber, and counts were normalized to loading controls.

DiD labeled normal 2D-cultured MSCs (2D MSC), 3D MSCs or 3D cytoplasts were retro-orbitally injected into BalB/C mice respectively. Indicated tissues were harvested 24 hours after injection and DiD labeled cells analyzed by FACS. FIG. 24 shows the successful generation of 3D-derived cytoplasts from 3D-cultured MSCs and also shows the 3D-derived cytoplasts have less lung trapping and better biodistribution to peripheral organs than 2D-cultured cells after injection into the circulation. This is expected to greatly improve their therapeutic ability to locate and deliver cargo to tissues.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A cell fusion partner, comprising:
an enucleated cell, wherein the enucleated cell is a cell without a nucleus that comprises:
(a) an exogenous targeting moiety specific to a microenvironment;
(b) a therapeutic agent to treat cancer or a neoplasm associated with the microenvironment, wherein the therapeutic agent comprises an oncolytic virus; and
(c) one or more intracellular organelles sufficient for in vivo release of the oncolytic virus in absence of the nucleus.

2. The cell fusion partner of claim 1, wherein the enucleated cell further comprises an exogenous mRNA molecule encoding a second therapeutic agent expressed by an intracellular organelle of the one or more intracellular organelles in the absence of the nucleus.

3. The cell fusion partner of claim 2, wherein the second therapeutic agent comprises a chimeric antigen receptor (CAR).

4. The cell fusion partner of claim 1, wherein the enucleated cell has a diameter comprising less than or equal to about 100 micrometers.

5. A pharmaceutical formulation comprising:
(a) the cell fusion partner of claim 1; and
(b) a pharmaceutically acceptable: excipient, diluent, or carrier.

6. The pharmaceutical formulation of claim 5, formulated for human administration for the treatment of the cancer, wherein the cancer comprises non-Hodgkin lymphoma (NHL), chronic lymphocytic leukemia (CLL), acute lymphoblastic leukemia (ALL), multiple myeloma (MM), or a combination thereof.

7. The cell fusion partner of claim 1, wherein the targeting moiety comprises CXCR4, CCR2, CCR1, CCR5, CXCR7, CXCR2, CXCR1, SDF1α, CCL2, CCL3, CCL5, CCL8, CCL1, CXCL9, CXCL10, CCL11, CXCL12, or a combination thereof.

8. A cell fusion product, comprising:
(a) an enucleated cell, wherein the enucleated cell is a cell without a nucleus that comprises:
(i) an exogenous targeting moiety specific to a microenvironment;
(ii) a therapeutic agent to treat cancer or a neoplasm associated with the microenvironment, wherein the therapeutic agent comprises an oncolytic virus; and
(iii) one or more intracellular organelles sufficient for in vivo release of the oncolytic virus in absence of the nucleus; and
(b) a target cell that is bound to the exogenous targeting moiety of the enucleated cell.

9. The cell fusion product of claim 8, wherein the target cell is a cancer cell.

10. The cell fusion product of claim 9, wherein the cancer cell is a cell from a non-Hodgkin lymphoma (NHL), a chronic lymphocytic leukemia (CLL), an acute lymphoblastic leukemia (ALL), a multiple myeloma (MM), or a combination thereof.

11. The cell fusion product of claim 8, wherein the enucleated cell further comprises an exogenous mRNA molecule encoding a second therapeutic agent expressed by an intracellular organelle of the one or more intracellular organelles in the absence of the nucleus.

12. The cell fusion product of claim 11, wherein the second therapeutic agent comprises a chimeric antigen receptor (CAR).

13. The cell fusion product of claim 8, wherein the cell fusion product has an in vivo lifespan comprising fewer than or equal to about five days.

14. The cell fusion product of claim 8, wherein the enucleated cell has a diameter comprising less than or equal to about 100 micrometers.

15. The cell fusion product of claim 8, wherein the targeting moiety comprises CXCR4, CCR2, CCR1, CCR5, CXCR7, CXCR2, CXCR1, SDF1α, CCL2, CCL3, CCL5, CCL8, CCL1, CXCL9, CXCL10, CCL11, CXCL12, or a combination thereof.

* * * * *

SEQUENCE LISTING

```
<160> NUMBER OF SEQ ID NOS: 20

<210> SEQ ID NO 1
<211> LENGTH: 229
<212> TYPE: DNA
<213> ORGANISM: Artificial
<220> FEATURE:
<223> OTHER INFORMATION: RSV promoter

<400> SEQUENCE: 1
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaac                 229

<210> SEQ ID NO 2
<211> LENGTH: 181
<212> TYPE: DNA
<213> ORGANISM: Artificial
<220> FEATURE:
<223> OTHER INFORMATION: Truncated HIV-1 5' long terminal repeat

<400> SEQUENCE: 2
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
```

```
tgtgactctg gtaactagag atccctcaga ccctttagt cagtgtggaa aatctctagc    180
a                                                                   181

<210> SEQ ID NO 3
<211> LENGTH: 45
<212> TYPE: DNA
<213> ORGANISM: Artificial
<220> FEATURE:
<223> OTHER INFORMATION: HIV-1 packaging signal

<400> SEQUENCE: 3
tgagtacgcc aaaaattttg actagcggag gctagaagga gagag                   45

<210> SEQ ID NO 4
<211> LENGTH: 234
<212> TYPE: DNA
<213> ORGANISM: Artificial
<220> FEATURE:
<223> OTHER INFORMATION: HIV-1 Rev response element

<400> SEQUENCE: 4
aggagctttg ttccttgggt tcttgggagc agcaggaagc actatgggcg cagcgtcaat   60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcct         234

<210> SEQ ID NO 5
<211> LENGTH: 118
<212> TYPE: DNA
<213> ORGANISM: Artificial
<220> FEATURE:
<223> OTHER INFORMATION: Central polypurine tract

<400> SEQUENCE: 5
ttttaaaaga aaaggggga ttgggggta cagtgcaggg gaaagaatag tagacataat     60
agcaacagac atacaaacta agaattaca aaaacaaatt acaaaaattc aaaatttt      118

<210> SEQ ID NO 6
<211> LENGTH: 1178
<212> TYPE: DNA
<213> ORGANISM: Artificial
<220> FEATURE:
<223> OTHER INFORMATION: Human eukaryotic translation elongation factor
      1 alpha promoter

<400> SEQUENCE: 6
gctccggtgc ccgtcagtgg gcagagcgca catcgcccac agtccccgag aagttggggg   60
gaggggtcgg caattgaacc ggtgcctaga gaaggtggcg cggggtaaac tgggaaagtg   120
atgtcgtgta ctggctccgc ctttttcccg agggtggggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
cttccacctg gctgcagtac gtgattcttg atcccgagct tcgggttgga agtgggtggg   360
agagttcgag gccttgcgct taaggagccc cttcgcctcg tgcttgagtt gaggcctggc   420
ctgggcgctg gggccgccgc gtgcgaatct ggtggcacct tcgcgcctgt ctcgctgctt   480
tcgataagtc tctagccatt taaaattttt gatgacctgc tgcgacgctt ttttctggc   540 aagatagtct tgtaaatgcg ggccaagatc tgcacactgg tatttcggtt tttggggccg   600
```

| | |
|---|---|
| cgggcggcga cggggcccgt gcgtcccagc gcacatgttc ggcgaggcgg ggcctgcgag | 660 |
| cgcggccacc gagaatcgga cgggggtagt ctcaagctgg ccggcctgct ctggtgcctg | 720 |
| gtctcgcgcc gccgtgtatc gccccgccct gggcggcaag gctggcccgg tcggcaccag | 780 |
| ttgcgtgagc ggaaagatgg ccgcttcccg gccctgctgc agggagctca aaatggagga | 840 |
| cgcggcgctc gggagagcgg gcgggtgagt cacccacaca aaggaaaagg ccttttccgt | 900 |
| cctcagccgt cgcttcatgt gactccacgg agtaccgggc gccgtccagg cacctcgatt | 960 |
| agttctcgag cttttggagt acgtcgtctt taggttgggg ggaggggttt tatgcgatgg | 1020 |
| agtttcccca cactgagtgg gtggagactg aagttaggcc agcttggcac ttgatgtaat | 1080 |
| tctccttgga atttgccctt tttgagtttg gatcttggtt cattctcaag cctcagacag | 1140 |
| tggttcaaag ttttttttctt ccatttcagg tgtcgtga | 1178 |

<210> SEQ ID NO 7
<211> LENGTH: 6
<212> TYPE: DNA
<213> ORGANISM: Artificial
<220> FEATURE:
<223> OTHER INFORMATION: Kozak translation initiation sequence

<400> SEQUENCE: 7

| | |
|---|---|
| gccacc | 6 |

<210> SEQ ID NO 8
<211> LENGTH: 1059
<212> TYPE: DNA
<213> ORGANISM: Homo sapiens

<400> SEQUENCE: 8

| | |
|---|---|
| atggagggga tcagtatata cacttcagat aactacaccg aggaaatggg ctcaggggac | 60 |
| tatgactcca tgaaggaacc ctgttccgt gaagaaaatg ctaatttcaa taaaatcttc | 120 |
| ctgcccacca tctactccat catcttctta actggcattg tgggcaatgg attggtcatc | 180 |
| ctggtcatgg gttaccagaa gaaactgaga agcatgacgg acaagtacag gctgcacctg | 240 |
| tcagtggccg acctcctctt tgtcatcacg cttcccttct gggcagttga tgccgtggca | 300 |
| aactggtact ttgggaactt cctatgcaag gcagtccatg tcatctacac agtcaacctc | 360 |
| tacagcagtg tcctcatcct ggccttcatc agtctggacc gctacctggc catcgtccac | 420 |
| gccaccaaca gtcagaggcc aaggaagctg ttggctgaaa aggtggtcta tgttggcgtc | 480 |
| tggatccctg ccctcctgct gactattccc gacttcatct ttgccaacgt cagtgaggca | 540 |
| gatgacagat atatctgtga ccgcttctac cccaatgact tgtgggtggt tgtgttccag | 600 |
| tttcagcaca tcatggttgg ccttatcctg cctggtattg tcatcctgtc ctgctattgc | 660 |
| attatcatct ccaagctgtc acactccaag ggccaccaga agcgcaaggc cctcaagacc | 720 |
| acagtcatcc tcatcctggc tttcttcgcc tgttggctgc cttactacat tgggatcagc | 780 |
| atcgactcct tcatcctcct ggaaatcatc aagcaagggt gtgagtttga aacactgtg | 840 |
| cacaagtgga tttccatcac cgaggcccta gctttcttcc actgttgtct gaaccccatc | 900 |
| ctctatgctt tccttggagc caaatttaaa acctctgccc agcacgcact cacctctgtg | 960 |
| agcagagggt ccagcctcaa gatcctctcc aaaggaaagc gaggtggaca ttcatctgtt | 1020 |
| tccactgagt ctgagtcttc aagttttcac tccagctaa | 1059 |

<210> SEQ ID NO 9
<211> LENGTH: 598

```
<212> TYPE: DNA
<213> ORGANISM: Artificial
<220> FEATURE:
<223> OTHER INFORMATION: Woodchuck hepatitis virus posttranscriptional
      regulatory element

<400> SEQUENCE: 9
cgataatcaa cctctggatt acaaaatttg tgaaagattg actggtattc ttaactatgt    60
tgctcctttt acgctatgtg gatacgctgc tttaatgcct ttgtatcatg ctattgcttc   120
ccgtatggct ttcattttct cctccttgta taaatcctgg ttgctgtctc tttatgagga   180
gttgtggccc gttgtcaggc aacgtggcgt ggtgtgcact gtgtttgctg acgcaacccc   240
cactggttgg ggcattgcca ccacctgtca gctccttccc gggactttcg ctttcccccct   300 ccctattgcc acggcggaac tcatcgccgc ctgccttgcc cgctgctgga caggggctcg   360
gctgttgggc actgacaatt ccgtggtgtt gtcggggaag ctgacgtcct ttccatggct   420
gctcgcctgt gttgccacct ggattctgcg cgggacgtcc ttctgctacg tcccttcggc   480
cctcaatcca gcggaccttc cttcccgcgg cctgctgccg gctctgcggc ctcttccgcg   540
tcttcgcctt cgccctcaga cgagtcggat ctccctttgg gccgcctccc cgcatcgg    598

<210> SEQ ID NO 10
<211> LENGTH: 511
<212> TYPE: DNA
<213> ORGANISM: Artificial
<220> FEATURE:
<223> OTHER INFORMATION: Mouse phosphoglycerate kinase 1 promoter

<400> SEQUENCE: 10
ttctaccggg tagggaggc gcttttccca aggcagtctg gagcatgcgc tttagcagcc    60
ccgctgggca cttggcgcta cacaagtggc ctctggcctc gcacacattc cacatccacc   120
ggtaggcgcc aaccggctcc gttctttggt ggcccccttcg cgccaccttc tactcctccc   180
ctagtcagga agttcccccc cgccccgcag ctcgcgtcgt gcaggacgtg acaaatggaa   240
gtagcacgtc tcactagtct cgtgcagatg gacagcaccg ctgagcaatg gaagcgggta   300
ggcctttggg gcagcggcca atagcagctt tgctccttcg ctttctgggc tcagaggctg   360 ggaagggggtg gtccgggggg cgggctcagg ggcgggctca ggggcggggc gggcgcccga   420
aggtcctccg gaggcccggc attctgcacg cttcaaaagc gcacgtctgc cgcgctgttc   480
tcctcttcct catctccggg cctttcgacc t                                  511

<210> SEQ ID NO 11
<211> LENGTH: 1029
<212> TYPE: DNA
<213> ORGANISM: Artificial
<220> FEATURE:
<223> OTHER INFORMATION: Hygromycin resistance gene

<400> SEQUENCE: 11
accatgaaaa agcctgaact caccgcgacg tctgtcgaga agtttctgat cgaaaagttc    60
gacagcgtct ccgacctgat gcagctctcg gagggcgaag aatctcgtgc tttcagcttc   120
gatgtaggag ggcgtggata tgtcctgcgg gtaaatagct gcgccgatgg tttctacaaa   180
gatcgttatg tttatcggca ctttgcatcg gccgcgctcc cgattccgga agtgcttgac   240
attggggaat ttagcgagag cctgacctat tgcatctccc gccgtgcaca gggtgtcacg   300
ttgcaagacc tgcctgaaac cgaactgccc gctgttctgc agccggtcgc ggaggccatg   360
gatgcgatcg ctgcggccga tcttagccag acgagcgggt tcggcccatt cggaccgcaa   420
```

```
ggaatcggtc aatacactac atggcgtgat tcatatgcg cgattgctga tccccatgtg    480
tatcactggc aaactgtgat ggacgacacc gtcagtgcgt ccgtcgcgca ggctctcgat    540
gagctgatgc tttgggccga ggactgcccc gaagtccggc acctcgtgca cgcggatttc    600
ggctccaaca atgtcctgac ggacaatggc cgcataacag cggtcattga ctggagcgag    660
gcgatgttcg gggattccca atacgaggtc gccaacatct tcttctggag gccgtggttg    720
gcttgtatgg agcagcagac gcgctacttc gagcggaggc atccggagct tgcaggatcg    780
ccgcggctcc gggcgtatat gctccgcatt ggtcttgacc aactctatca gagcttggtt    840
gacggcaatt tcgatgatgc agcttgggcg cagggtcgat gcgacgcaat cgtccgatcc    900
ggagccggga ctgtcgggcg tacacaaatc gcccgcagaa gcgcggccgt ctggaccgat    960
ggctgtgtag aagtactcgc cgatagtgga accgacgcc ccagcactcg tccgagggca   1020
aaggaatag                                                            1029
```

```
<210> SEQ ID NO 12
<211> LENGTH: 235
<212> TYPE: DNA
<213> ORGANISM: Artificial
<220> FEATURE:
<223> OTHER INFORMATION: Truncated HIV-1 3' long terminal repeat

<400> SEQUENCE: 12
ctggaagggc taattcactc ccaacgaaga caagatctgc ttttgcttg tactgggtct      60 ctctggttag accagatctg agcctgggag ctctctggct aactagggaa cccactgctt   120
aagcctcaat aaagcttgcc ttgagtgctt caagtagtgt gtgcccgtct gttgtgtgac   180
tctggtaact agagatccct cagacccttt tagtcagtgt ggaaaatctc tagca        235
```

```
<210> SEQ ID NO 13
<211> LENGTH: 135
<212> TYPE: DNA
<213> ORGANISM: Artificial
<220> FEATURE:
<223> OTHER INFORMATION: Simian virus 40 early polyadenylation signal

<400> SEQUENCE: 13
acttgtttat tgcagcttat aatggttaca aataaagcaa tagcatcaca aatttcacaa     60
ataaagcatt ttttcactg cattctagtt gtggtttgtc caaactcatc aatgtatctt   120
atcatgtctg gctct                                                    135
```

```
<210> SEQ ID NO 14
<211> LENGTH: 861
<212> TYPE: DNA
<213> ORGANISM: Artificial
<220> FEATURE:
<223> OTHER INFORMATION: Ampicillin resistance gene

<400> SEQUENCE: 14
atgagtattc aacatttccg tgtcgccctt attcccttt ttgcggcatt ttgccttcct     60
gtttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
cgtattgacg ccgggcaaga gcaactcggt cgccgcatac actattctca gaatgacttg   300
gttgagtact caccagtcac agaaaagcat cttacggatg gcatgacagt aagagaatta   360
```

```
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatgatgaa cgaaatagac agatcgctga gataggtgcc    840
tcactgatta agcattggta a                                              861

<210> SEQ ID NO 15
<211> LENGTH: 589
<212> TYPE: DNA
<213> ORGANISM: Artificial
<220> FEATURE:
<223> OTHER INFORMATION: pUC origin of replication

<400> SEQUENCE: 15
ttgagatcct ttttttctgc gcgtaatctg ctgcttgcaa acaaaaaaac caccgctacc     60
agcggtggtt tgtttgccgg atcaagagct accaactctt tttccgaagg taactggctt    120
cagcagagcg cagataccaa atactgttct ctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaaga    420
gagaaaggcg acaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga ttttgtgat gctcgtcagg ggggcggagc ctatggaaa                 589

<210> SEQ ID NO 16
<211> LENGTH: 1191
<212> TYPE: DNA
<213> ORGANISM: Mus musculus

<400> SEQUENCE: 16
atgtccccaa gcttccttgt gctgctgacc atcttgggcc ctggcaacag ccttcagctg     60
caggacccct gggggcatga aaccaaggaa gccccgggtc ctgtgcatct ccgggaacgg    120
aggcaggtgg ttggggatga cgattttgag gaccctgact atacgtataa cacagacccc    180
ccagaattgc tgaaaaatgt caccaacacc gtggctgctc accctgagct gccaaccacc    240
gtggtcatgc tagagagaga ttccacgagc gctggaacct cgagagagc cactgagaag    300 attgccacca ctgaccctac tgccccaggt acaggaggga cagctgttgg gatgctgagc    360
acagactctg ccacacagtg gagtctaacc tcagtagaga ccgtccaacc agcatccaca    420
gaggtagaga cctcgcagcc agcacccatg gaggcagaga cctcgcagcc agcacccatg    480
gaggcagaga cctcgcagcc agcacccatg gaggcagaca cctcaaagcc agcacccacg    540
gaggcagaga cctcaaagcc agcacccacg gaggcagaga cctctcagcc agcacccaac    600
gaggcagaga cctcaaaacc agcacccacg gaggcagaga cctcaaaacc agcacccacg    660
gaggcagaga ccacccagct tcccaggatt caggctgtaa aaactctgtt tacaacgtct    720
```

```
gcagccaccg aagtcccttc cacagaacct accaccatgg agacggcgtc cacagagtct    780
aacgagtcta ccatcttcct tgggccatcc gtgactcact acctgacag cggcctgaag     840 aaagggctga ttgtgacccc tgggaattca cctgccccaa ccctgccagg gagttcagat    900
ctcatcccgg tgaagcaatg tctgctgatt atcctcatct tggcttctct ggccaccatc    960
ttcctcgtgt gcacagtggt gctggcggtc cgtctgtccc gtaagaccca catgtaccca   1020
gtgcggaact actcccccac ggagatgatc tgcatctcgt ccctgctacc tgagggggga   1080 gacgggccc ctgtcacagc caatgggggc ctgcccaagg tccaggacct gaagacagag    1140
cccagtgggg accgggatgg ggacgacctc accctgcaca gcttcctccc t           1191
```

<210> SEQ ID NO 17
<211> LENGTH: 1170
<212> TYPE: DNA
<213> ORGANISM: Mus musculus

<400> SEQUENCE: 17

```
atgccaaccc cctgcccacc agcctgcctg tccacgccag ggacacacag actccttccc    60
tttccagact ggaaagcccc ctcctgggag agcaggaagg aagcaacctg caactcttcc   120
agccctggac cttgggctga acctacagtt caagggtacc accccaccag gaggctgcgg   180
gcctggggcg gcctagctgg aggagcaaca ttcatggtaa tttggttttt ctggctgtgg   240
ggatcagctc ctggaagtgc ccctgtgcct cagtccacac tcaccatcct tatctggcac   300
tggcctttca ccaaccggcc gccagagcta cctggtgaca cctgcactcg ctatggcatg   360 ccagctgcc gtctgagtgc taaccggagc ctgctagcca gtgctgatgc tgtggtcttc    420
caccaccgtg agctgcaaac ccggcaatct ctcctacccc tggaccagag gccacacgga   480
cagccttggg tctgggcctc catggaatcg cccagtaata cccatggtct ccatcgcttc   540
cggggcatct tcaactgggt gctgagctat cggcgtgatt cagatatctt tgtaccctac   600
ggtcgcttgg agcctctctc tgggcccaca tccccactac cggccaaaag caggatggct   660
gcctgggtga tcagcaattt ccaggagcgg cagcagcgtg caaagctgta ccggcagctg   720
gcccctcatc tgcaggtgga tgtgttcggt cgcgccagcg gacggcccct atgcgctaat   780
tgtctgctgc ccactttggc ccggtaccgc ttctacctgg cctttgagaa ctcacagcat   840
cgggactaca tcactgagaa gttctggcgc aatgccctgg cggctggtgc tgtacccgtg   900
gcgctgggac ctcctcgggc cacctacgag gcttttgtgc caccagatgc ctttgtacac   960
gtggacgact tcagctctgc ccgtgaactg gctgtcttcc tcgtcagcat gaatgagagt   1020
cgttatcgtg gcttctttgc ttggcgagac cggctccgtg tgcggctcct gggtgactgg   1080
agggagcgct tctgcaccat ctgtgcccgc tacccttact tgccccgcag ccaggtctat   1140
gaagaccttg aaagctggtt ccaggcttga                                    1170
```

<210> SEQ ID NO 18
<211> LENGTH: 66
<212> TYPE: DNA
<213> ORGANISM: Artificial
<220> FEATURE:
<223> OTHER INFORMATION: Self-cleaving 2A peptide from porcine
      teschovirus-1

<400> SEQUENCE: 18

```
ggaagcggag ccacgaactt ctctctgtta aagcaagcag gagatgttga agaaaacccc    60
gggcct                                                               66
```

<210> SEQ ID NO 19
<211> LENGTH: 996
<212> TYPE: DNA
<213> ORGANISM: Mus musculus

<400> SEQUENCE: 19

| | | | | | |
|---|---|---|---|---|---|
| atgtggccct | tggcggcggc | gctgttgctg | ggctcctgct | gctgcggttc | agctcaacta | 60 |
| ctgtttagta | acgtcaactc | catagagttc | acttcatgca | atgaaactgt | ggtcatccct | 120 |
| tgcatcgtcc | gtaatgtgga | ggcgcaaagc | accgaagaaa | tgtttgtgaa | gtggaagttg | 180 |
| aacaaatcgt | atattttcat | ctatgatgga | aataaaaata | gcactactac | agatcaaaac | 240 |
| tttaccagtg | caaaaatctc | agtctcagac | ttaatcaatg | gcattgcctc | tttgaaaatg | 300 |
| gataagcgcg | atgccatggt | gggaaactac | acttgcgaag | tgacagagtt | atccagagaa | 360 |
| ggcaaaacag | ttatagagct | gaaaaaccgc | acggccttca | acactgacca | aggatcagcc | 420 |
| tgttcttacg | aggaggagaa | aggaggttgc | aaattagttt | cgtggttttc | tccaaatgaa | 480 |
| aagatcctca | ttgttatttt | cccaattttg | gctatactcc | tgttctgggg | aaagtttggt | 540 |
| attttaacac | tcaaatataa | atccagccat | acgaataaga | gaatcattct | gctgctcgtt | 600 |
| gccgggctgg | tgctcacagt | catcgtggtt | gttggagcca | tccttctcat | cccaggagaa | 660 |
| aagcccgtga | agaatgcttc | tggacttggc | ctcattgtaa | tctctacggg | gatattaata | 720 |
| ctacttcagt | acaatgtgtt | tatgacagct | tttggaatga | cctcttttcac | cattgccata | 780 |
| ttgatcactc | aagtgctggg | ctacgtcctt | gctttggtcg | ggctgtgtct | ctgcatcatg | 840 |
| gcatgtgagc | cagtgcacgg | ccccctttg | atttcaggtt | tggggatcat | agctctagca | 900 |
| gaactacttg | gattagttta | tatgaagttt | gtcgcttcca | accagaggac | tatccaacct | 960 |
| cctaggaaag | ctgtagagga | accccttaac | gaatag | | | 996 |

<210> SEQ ID NO 20
<211> LENGTH: 711
<212> TYPE: DNA
<213> ORGANISM: Mus musculus

<400> SEQUENCE: 20

| | | | | | |
|---|---|---|---|---|---|
| atggtgagca | agggcgagga | ggataacatg | gccatcatca | aggagttcat | gcgcttcaag | 60 |
| gtgcacatgg | agggctccgt | gaacggccac | gagttcgaga | tcgagggcga | gggcgagggc | 120 |
| cgcccctacg | agggcaccca | gaccgccaag | ctgaaggtga | ccaagggtgg | ccccctgccc | 180 |
| ttcgcctggg | acatcctgtc | ccctcagttc | atgtacggct | ccaaggccta | cgtgaagcac | 240 |
| cccgccgaca | tccccgacta | cttgaagctg | tccttcccg | agggcttcaa | gtgggagcgc | 300 |
| gtgatgaact | tcgaggacgg | cggcgtggtg | accgtgaccc | aggactcctc | cctgcaggac | 360 |
| ggcgagttca | tctacaaggt | gaagctgcgc | ggcaccaact | tcccctccga | cggccccgta | 420 |
| atgcagaaga | agaccatggg | ctgggaggcc | tcctccgagc | ggatgtaccc | cgaggacggc | 480 |
| gccctgaagg | gcgagatcaa | gcagaggctg | aagctgaagg | acggcggcca | ctacgacgct | 540 |
| gaggtcaaga | ccacctacaa | ggccaagaag | cccgtgcagc | tgcccggcgc | ctacaacgtc | 600 |
| aacatcaagt | tggacatcac | ctcccacaac | gaggactaca | ccatcgtgga | acagtacgaa | 660 |
| cgcgccgagg | gccgccactc | caccggcggc | atggacgagc | tgtacaagta | a | 711 |